US008821877B2

(12) United States Patent
Olson et al.

(10) Patent No.: US 8,821,877 B2
(45) Date of Patent: Sep. 2, 2014

(54) METHODS FOR INHIBITING HIV-1 REPLICATION INVOLVING THE ADMINISTRATION OF AN ANTI-CCR5 RECEPTOR MONOCLONAL ANTIBODY AND SMALL MOLECULE CCR5 RECEPTOR ANTAGONIST

(75) Inventors: William C. Olson, Ossining, NY (US); Paul J. Maddon, Scarsdale, NY (US); Daniel C. Pevear, Medford, MA (US); Robert J. Israel, Suffern, NY (US); Jose D. Murga, Rosedale, NY (US)

(73) Assignee: CytoDyn Inc., Vancouver, WA (US)

(*) Notice: Subject to any disclaimer, the term of this patent is extended or adjusted under 35 U.S.C. 154(b) by 0 days.

(21) Appl. No.: 12/954,464

(22) Filed: Nov. 24, 2010

(65) Prior Publication Data
US 2011/0200592 A1 Aug. 18, 2011

Related U.S. Application Data

(62) Division of application No. 11/491,330, filed on Jul. 21, 2006, now abandoned.

(60) Provisional application No. 60/702,064, filed on Jul. 22, 2005, provisional application No. 60/701,889, filed on Jul. 23, 2005, provisional application No. 60/711,528, filed on Aug. 26, 2005, provisional application No. 60/715,619, filed on Sep. 9, 2005.

(51) Int. Cl.
*A61K 39/395* (2006.01)
*C12Q 1/70* (2006.01)
*C07K 16/00* (2006.01)
*A01N 57/36* (2006.01)
*A01N 43/42* (2006.01)
*A61K 31/497* (2006.01)

(52) U.S. Cl.
USPC ....... 424/156.1; 435/5; 530/388.75; 514/110; 514/253.01; 514/304

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,225,539 A | 7/1993 | Winter et al. |
| 5,229,275 A | 7/1993 | Goroff et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,585,089 A | 12/1996 | Queen et al. |
| 5,591,669 A | 1/1997 | Krimpenfort et al. |
| 5,693,761 A | 12/1997 | Queen et al. |
| 5,817,767 A | 10/1998 | Allaway |
| 5,939,320 A | 8/1999 | Littman |
| 6,025,154 A | 2/2000 | Li et al. |
| 6,100,087 A | 8/2000 | Rossi et al. |
| 6,107,019 A | 8/2000 | Allaway et al. |
| 6,150,584 A | 11/2000 | Kucherlapati et al. |
| 6,258,527 B1 | 7/2001 | Littman |
| 6,258,782 B1 | 7/2001 | Barney et al. |
| 6,261,763 B1 | 7/2001 | Allaway et al. |
| 6,265,184 B1 | 7/2001 | Gray |
| 6,268,477 B1 | 7/2001 | Gray et al. |
| 6,344,545 B1 | 2/2002 | Allaway et al. |
| 6,448,375 B1 | 9/2002 | Samson |
| 6,476,034 B2 | 11/2002 | Wang et al. |
| 6,528,625 B1 | 3/2003 | Wu |
| 6,548,636 B2 | 4/2003 | Dragic |
| 6,692,745 B2 | 2/2004 | Olson |
| 6,692,938 B2 | 2/2004 | Samson |
| 6,759,519 B2 | 7/2004 | Li et al. |
| 6,797,811 B1 | 9/2004 | Gray |
| 6,800,447 B2 | 10/2004 | Samson |
| 6,908,734 B2 | 6/2005 | Dragic et al. |
| 6,930,174 B2 | 8/2005 | Samson et al. |

(Continued)

FOREIGN PATENT DOCUMENTS

CA 2216990 12/1997
EP 96870021.1 3/1996

(Continued)

OTHER PUBLICATIONS

Trkola, A., et al., 2005, Delay of HIV-1 rebound after cessation of antiretroviral therapy through passive transfer of human neutralizing antibodies, Nat. Med. 11(6):615-622.*
Gait, M. J., and J. Karn, 1995, Progress in anti-HIV structure-based drug design, TIBTECH 13:430-438.*
Gustchina, E., et al., Dec. 2007, A monoclonal Fab derived from a human nonimmune phage library reveals a new epitope on gp41 and neutralizes diverse human immunodeficiency virus type 1 strains, J. Virol. 81(23):12946-12953.*
European Supplementary Partial Search Report issued Sep. 27, 2004 for European Application No. 99966466.
Pending claims in W.C. Olson et al., U.S. Appl. No. 11/316,078, filed Dec. 21, 2005.

(Continued)

*Primary Examiner* — Jeffrey Parkin
(74) *Attorney, Agent, or Firm* — Miller Nash LLP; Chandra E. Eidt

(57) ABSTRACT

This method provides a method for reducing HIV-1 viral load in an HIV-1-infected human subject which comprises administering to the subject at a predefined interval effective HIV-1 viral load-reducing doses of (a) a humanized antibody designated PRO 140, or of (b) an anti-CCR5 receptor monoclonal antibody. This invention also provides a method for inhibiting in a human subject the onset or progression of an HIV-1-associated disorder, the inhibition of which is effected by inhibiting fusion of HIV-1 to CCR5+CD4+ target cells in the subject. This invention also provides a method for treating a subject infected with HIV-1 comprising administering to the subject (a) a monoclonal antibody which (i) binds to a CCR5 receptor on the surface of the subject's CD4+ cells and (ii) inhibits fusion of HIV-1 to the subject's CCR5+CD4+ cells, and (b) a non-antibody CCR5 receptor antagonist, in amounts effective to treat the subject.

19 Claims, 17 Drawing Sheets

(56) References Cited

U.S. PATENT DOCUMENTS

| | | |
|---|---|---|
| 6,972,126 B2 | 12/2005 | Allaway et al. |
| 7,060,273 B2 | 6/2006 | Olson et al. |
| 7,118,859 B2 | 10/2006 | Litwin et al. |
| 7,122,185 B2 | 10/2006 | Olson et al. |
| 7,129,055 B2 | 10/2006 | Littman et al. |
| 7,138,119 B2 | 11/2006 | Olson et al. |
| 7,151,087 B2 | 12/2006 | Combadiere et al. |
| 7,160,546 B2 | 1/2007 | Li et al. |
| 7,175,988 B2 | 2/2007 | Roschke et al. |
| 7,223,844 B2 | 5/2007 | Dimitrov et al. |
| 7,345,153 B2 | 3/2008 | Litwin et al. |
| 7,501,123 B2 | 3/2009 | Roschke et al. |
| 2002/0045161 A1 | 4/2002 | Allaway et al. |
| 2002/0048786 A1 | 4/2002 | Rosen et al. |
| 2002/0061834 A1 | 5/2002 | Rosen et al. |
| 2002/0068813 A1 | 6/2002 | Dragic et al. |
| 2002/0146415 A1 | 10/2002 | Olson et al. |
| 2002/0155429 A1 | 10/2002 | Allaway et al. |
| 2002/0177603 A1 | 11/2002 | Johnson et al. |
| 2003/0003440 A1 | 1/2003 | Lopalco et al. |
| 2003/0092632 A1 | 5/2003 | Dragic et al. |
| 2003/0139571 A1 | 7/2003 | Dragic et al. |
| 2003/0166024 A1 | 9/2003 | Rosen et al. |
| 2003/0166870 A1 | 9/2003 | Wu et al. |
| 2003/0195348 A1 | 10/2003 | Combadiere et al. |
| 2004/0062767 A1 | 4/2004 | Olson et al. |
| 2004/0086528 A1 | 5/2004 | Allaway et al. |
| 2004/0110127 A1 | 6/2004 | Samson et al. |
| 2004/0161739 A1 | 8/2004 | Samson et al. |
| 2004/0228869 A1 | 11/2004 | Olson et al. |
| 2005/0131042 A1 | 6/2005 | Flentge |
| 2005/0136061 A1 | 6/2005 | Dillon et al. |
| 2005/0154193 A1 | 7/2005 | Roschke et al. |
| 2006/0029932 A1 | 2/2006 | Allaway et al. |
| 2006/0140977 A1 | 6/2006 | Allaway et al. |
| 2006/0154857 A1 | 7/2006 | Redfield et al. |
| 2006/0194244 A1 | 8/2006 | Allaway et al. |
| 2007/0026441 A1 | 2/2007 | Olson et al. |
| 2007/0231327 A1 | 10/2007 | Olson et al. |
| 2007/0248624 A1 | 10/2007 | Tahri et al. |
| 2007/0274986 A1 | 11/2007 | Olson et al. |

FOREIGN PATENT DOCUMENTS

| | | |
|---|---|---|
| EP | 96870102.9 | 8/1996 |
| EP | 0815137 | 12/1996 |
| EP | 1145721 A2 | 10/2001 |
| EP | 1146055 A2 | 10/2001 |
| EP | 1146122 A2 | 10/2001 |
| EP | 1148126 A2 | 10/2001 |
| EP | 1148127 A2 | 10/2001 |
| EP | 1149582 A2 | 10/2001 |
| EP | 1199360 A2 | 4/2002 |
| EP | 0883687 B1 | 10/2004 |
| EP | 1482042 A1 | 12/2004 |
| WO | WO 90/07861 | 7/1990 |
| WO | WO 94/19017 | 9/1994 |
| WO | WO 95/16789 | 6/1995 |
| WO | WO 96/41020 | 12/1996 |
| WO | WO 97/22698 | 6/1997 |
| WO | WO 97/26009 | 7/1997 |
| WO | WO 97/28258 | 8/1997 |
| WO | WO 97/32019 | 9/1997 |
| WO | WO 97/37005 | 10/1997 |
| WO | WO 97/44055 | 11/1997 |
| WO | WO 97/44462 | 11/1997 |
| WO | WO 97/47318 | 12/1997 |
| WO | WO 97/47319 | 12/1997 |
| WO | WO 98/18826 | 5/1998 |
| WO | WO 98/56421 | 12/1998 |
| WO | WO 00/35409 | 6/2000 |
| WO | WO 01/55439 | 8/2001 |
| WO | WO 01/58915 | 8/2001 |
| WO | WO 01/58916 | 8/2001 |
| WO | WO 01/62255 A1 | 8/2001 |
| WO | WO 01/64710 | 9/2001 |
| WO | WO 01/90106 A2 | 11/2001 |
| WO | WO 02/22077 | 3/2002 |
| WO | WO 02/22077 A2 | 3/2002 |
| WO | WO 02/064612 | 8/2002 |
| WO | WO 02/068608 | 9/2002 |
| WO | WO 02/083172 | 10/2002 |
| WO | WO 02/083172 A1 | 10/2002 |
| WO | WO 03/072766 | 9/2003 |
| WO | WO 03/072766 A1 | 9/2003 |
| WO | WO 03/82289 A1 | 10/2003 |
| WO | WO 2007/014114 | 2/2007 |

OTHER PUBLICATIONS

Pending claims in G.P. Allaway et al., U.S. Appl. No. 11/258,963, filed Oct. 25, 2005.

Pending claims in W.C. Olson et al., U.S. Appl. No. 11/581,944, filed Oct. 16, 2006.

Pending claims in W.C. Olson et al., U.S. Appl. No. 11/581,945, filed Oct. 16, 2006.

Pending claims in W.C. Olson et al., U.S. Appl. No. 11/520,556, filed Sep. 12, 2006.

Pending claims in V.M. Litwin et al., U.S. Appl. No. 11/544,346, filed Oct. 5, 2006.

Pending claims in G.P. Allaway et al., U.S. Appl. No. 09/460,216, filed Dec. 13, 1999.

W.C. Olson et al., U.S. Appl. No. 09/464,902, filed Dec. 16, 1999, including allowed claims.

W.C. Olson et al., U.S. Appl. No. 09/594,983, filed Jun. 15, 2000, including allowed claims.

U.S. Appl. No. 10/081,128, filed Feb. 22, 2002, W.C. Olson et al.

U.S. Appl. No. 09/212,793, filed Feb. 16, 1998, W.C. Olson et al.

U.S. Appl. No. 08/663,616, filed Jun. 14, 1996, G.P. Allaway et al.

U.S. Appl. No. 08/673,682, filed Jun. 25, 1996, G.P. Allaway et al.

U.S. Appl. No. 08/874,570, filed Jun. 13, 1997, G.P. Allaway et al.

U.S. Appl. No. 08/874,618, filed Jun. 13, 1997, G.P. Allaway et al.

U.S. Appl. No. 09/118,415, filed Jul. 17, 1998, V.M. Litwin et al.

U.S. Appl. No. 60/358,886, filed Feb. 22, 2002, W.C. Olson et al.

U.S. Appl. No. 60/017,157, filed Feb. 20, 1996, D. Littman et al.

U.S. Appl. No. 60/266,738, filed Feb. 6, 2001, W.C. Olson et al.

U.S. Appl. No. 60/282,380, filed Apr. 6, 2001, W.C. Olson et al.

U.S. Appl. No. 60/019,715, filed Jun. 14, 1996, W.C. Olson et al.

U.S. Appl. No. 60/019,941, filed Jun. 14, 1996, G.P. Allaway et al.

U.S. Appl. No. 60/112,532, filed Dec. 16, 1998, W.C. Olson et al.

U.S. Appl. No. 60/185,667, filed Feb. 29, 2000, T. Dragic.

U.S. Appl. No. 60/205,839, filed May 19, 2000, T. Dragic.

U.S. Appl. No. 60/267,231, filed Feb. 7, 2001, T. Dragic.

U.S. Appl. No. 60/272,203, filed Feb. 28, 2001, T. Dragic.

U.S. Appl. No. 60/018,508, filed May 28, 1996, C. Combadiere et al.

Feb. 15, 1996 Advisory Action in connection with U.S. Appl. No. 08/169,311.

Sep. 13, 1995 Final Office Action in connection with U.S. Appl. No. 08/169,311.

Nov. 23, 1994 Office Action in connection with U.S. Appl. No. 08/169,311.

Aug. 18, 1994 Office Action in connection with U.S. Appl. No. 08/169,311.

Jul. 16, 1998 Notice of Acceptance in connection with Australian Application No. 14387/95.

Nov. 27, 1996 Examiner's First Report in connection with Australian Application No. 14387/95.

Jul. 5, 2000 Notice of Acceptance in connection with Australian Application No. 62690/96.

Nov. 10, 1998 Examiner's First Report in connection with Australian Application No. 62690/96.

Sep. 14, 2006 Official Action in connection with Canadian Application No. 2,224,003.

Sep. 11, 2006 Communication Pursuant to Article 96(2) EPC in connection with European Application No. 96 921 473.3.

Mar. 8, 2006 Summons to Oral Proceedings Pursuant to Rule 71(1) EPC in connection with European Application No. 96 921 473.3.

(56) References Cited

OTHER PUBLICATIONS

Feb. 24, 2005 Provision of the Minutes in accordance with Rule 76(4) EPC in connection with European Application No. 96 921 473.3.
Feb. 24, 2005 Decision to Refuse a European Patent Application in connection with European Application No. 96 921 473.3.
Aug. 30, 2004 Summons to Oral Proceedings Pursuant to Rule 71(1) EPC in connection with European Application No. 96 921 473.3.
Dec. 19, 2002 Communication Pursuant to Article 96(2) EPC in connection with European Application No. 96 921 473.3.
Jul. 6, 2001 Communication Pursuant to Article 96(2) EPC in connection with European Application No. 96 921 473.3.
Dec. 20, 1999 Notice of Allowance and Allowability in connection with U.S. Appl. No. 08/973,601.
Aug. 3, 1999 Advisory Action in connection with U.S. Appl. No. 08/973,601.
Mar. 25, 1999 Office Action in connection with U.S. Appl. No. 08/973,601.
Jun. 24, 1998 Office Action in connection with U.S. Appl. No. 08/973,601.
Jan. 11, 2005 Notice of Allowance and Allowability in connection with U.S. Appl. No. 09/412,284.
Dec. 2, 2003 Final Office Action in connection with U.S. Appl. No. 09/412,284.
Feb. 3, 2003 Office Action in connection with U.S. Appl. No. 09/412,284.
Apr. 8, 2002 Advisory Action in connection with U.S. Appl. No. 09/412,284.
Sep. 11, 2001 Final Office Action in connection with U.S. Appl. No. 09/412,284.
Dec. 19, 2000 Office Action in connection with U.S. Appl. No. 09/412,284.
Apr. 18, 2007 Office Action in connection with U.S. Appl. No. 11/258,963.
Dec. 26, 2006 Office Action in connection with U.S. Appl. No. 11/258,963.
Feb. 8, 2007 Office Action in connection with U.S. Appl. No. 09/904,356.
May 2, 2006 Final Office Action in connection with U.S. Appl. No. 09/904,356.
Oct. 12, 2005 Office Action in connection with U.S. Appl. No. 09/904,356.
Jul. 29, 2005 Advisory Action in connection with U.S. Appl. No. 09/904,356.
Nov. 17, 2004 Final Office Action in connection with U.S. Appl. No. 09/904,356.
Jul. 1, 2003 Office Action in connection with U.S. Appl. No. 09/904,356.
Sep. 29, 2003 Advisory Action in connection with U.S. Appl. No. 09/118,415.
Jan. 28, 2003 Final Office Action in connection with U.S. Appl. No. 09/118,415.
Apr. 9, 2002 Office Action in connection with U.S. Appl. No. 09/118,415.
Aug. 14, 2001 Advisory Action in connection with U.S. Appl. No. 09/118,415.
Nov. 24, 2000 Final Office Action in connection with U.S. Appl. No. 09/118,415.
Feb. 11, 2000 Office Action in connection with U.S. Appl. No. 09/118,415.
Aug. 3, 2006 Notice of Allowance and Allowability in connection with U.S. Appl. No. 09/891,062.
Jul. 17, 2006 Notice of Allowability in connection with U.S. Appl. No. 09/891,062.
May 18, 2006 Notice of Allowance and Allowability in connection with U.S. Appl. No. 09/891,062.
Aug. 8, 2005 Office Action in connection with U.S. Appl. No. 09/891,062.
Mar. 21, 2005 Office Action in connection with U.S. Appl. No. 09/891,062.
May 28, 2004 Advisory Action in connection with U.S. Appl. No. 09/891,062.
Sep. 24, 2003 Final Office Action in connection with U.S. Appl. No. 09/891,062.
Dec. 18, 2002 Office Action in connection with U.S. Appl. No. 09/891,062.
Apr. 30, 2007 Notice of Allowance and Allowability in connection with U.S. Appl. No. 11/544,346.
Mar. 3, 1997 Office Action in connection with U.S. Appl. No. 08/627,684.
Jun. 23, 1997 Office Action in connection with U.S. Appl. No. 08/663,616.
Mar. 13, 1997 Office Action in connection with U.S. Appl. No. 08/673,682.
Nov. 28, 2000 Notice of Acceptance in connection with Australian Application No. 26074/97.
Jul. 13, 1999 Examiner's First Report in connection with Australian Application No. 26074/97.
Oct. 23, 2006 Official Action in connection with Canadian Application No. 2,250,829.
May 27, 2005 Official Action in connection with Canadian Application No. 2,250,829.
May 4, 2007 Summons to Attend Oral Proceedings Pursuant to Rule 71(1) EPC in connection with European Application No. 97917856.3.
Jan. 27, 2006 Communication Pursuant to Article 96(2) EPC in connection with European Application No. 97917856.3.
Oct. 21, 2005 Communication Pursuant to Article 115(2) EPC in connection with European Application No. 97917856.3.
Apr. 1, 2005 Communication Pursuant to Article 96(2) EPC in connection with European Application No. 97917856.3.
Aug. 5, 2004 Communication Pursuant to Article 96(2) EPC in connection with European Application No. 97917856.3.
Jan. 27, 2004 Communication Pursuant to Article 96(2) EPC in connection with European Application No. 97917856.3.
May 9, 2003 Communication Pursuant to Article 96(2) EPC in connection with European Application No. 97917856.3.
Mar. 6, 2002 Search Report Communication in connection with European Application No. 97917856.3.
Feb. 27, 2007 Notification of Reasons for Rejection in connection with Japanese Application. No. 535610/97 (English translation).
May 19, 2006 Examiner's First Report in connection with Australian Application No. 2004233505.
Jul. 26, 2004 Notice of Acceptance in connection with Australian Application No. 35106/01.
Jul. 5, 2004 Examiner's Second Report in connection with Australian Application No. 35106/01.
Nov. 1, 2002 Examiner's First Report in connection with Australian Application No. 35106/01.
Dec. 4, 2001 Notice of Allowance and Allowability in connection with U.S. Appl. No. 08/831,823.
Jan. 16, 2001 Notice of Allowance and Allowability in connection with U.S. Appl. No. 08/831,823.
Sep. 26, 2000 Advisory Action in connection with U.S. Appl. No. 08/831,823.
Apr. 11, 2000 Final Office Action in connection with U.S. Appl. No. 08/831,823.
Jul. 21, 1999 Final Office Action in connection with U.S. Appl. No. 08/831,823.
Dec. 21, 1998 Office Action in connection with U.S. Appl. No. 08/831,823.
Aug. 17, 1998 Office Action in connection with U.S. Appl. No. 08/831,823.
Jun. 15, 2006 Final Office Action in connection with U.S. Appl. No. 09/888,938.
Sep. 7, 2005 Office Action in connection with U.S. Appl. No. 09/888,938.
Aug. 4, 2004 Office Action in connection with U.S. Appl. No. 09/888,938.
May 5, 2004 Office Action in connection with U.S. Appl. No. 09/888,938.
Jun. 22, 1999 Notice of Allowance and Allowability in connection with U.S. Appl. No. 08/876,078.

(56) References Cited

OTHER PUBLICATIONS

Dec. 21, 1998 Final Office Action in connection with U.S. Appl. No. 08/876,078.
Mar. 23, 1998 Office Action in connection with U.S. Appl. No. 08/876,078.
Jun. 16, 2006 Communication Pursuant to Article 96(2) EPC in connection with European Application No. 98 931 261.6.
Jun. 17, 2005 Communication Pursuant to Article 96(2) EPC in connection with European Application No. 98 931 261.6.
Oct. 17, 2006 Final Office Action in connection with U.S. Appl. No. 09/460,216.
Feb. 3, 2006 Office Action in connection with U.S. Appl. No. 09/460,216.
Jul. 29, 2005 Advisory Action in connection with U.S. Appl. No. 09/460,216.
Feb. 9, 2005 Final Office Action in connection with U.S. Appl. No. 09/460,216.
Sep. 26, 2003 Advisory Action in connection with U.S. Appl. No. 09/460,216.
Feb. 27, 2003 Final Office Action in connection with U.S. Appl. No. 09/460,216.
Oct. 2, 2001 Office Action in connection with U.S. Appl. No. 09/460,216.
Sep. 9, 2002 Notice of Acceptance in connection with Australian Application No. 81426/98.
Feb. 27, 2002 Examiner's Second Report in connection with Australian Application No. 81426/98.
Feb. 21, 2001 Examiner's First Report in connection with Australian Application No. 81426/98.
Feb. 4, 1997 Office Action in connection with U.S. Appl. No. 08/665,090.
Aug. 29, 2000 Notice of Allowance and Allowability in connection with U.S. Appl. No. 08/874,618.
Nov. 19, 1999 Office Action in connection with U.S. Appl. No. 08/874,618.
May 24, 1999 Final Office Action in connection with U.S. Appl. No. 08/874,618.
Sep. 2, 1998 Office Action in connection with U.S. Appl. No. 08/874,618.
Dec. 13, 2005 Final Office Action in connection with U.S. Appl. No. 09/724,105.
Mar. 23, 2005 Office Action in connection with U.S. Appl. No. 09/724,105.
Sep. 23, 2004 Office Action in connection with U.S. Appl. No. 09/724,105.
May 19, 2004 Office Action in connection with U.S. Appl. No. 09/724,105.
Dec. 19, 2006 Office Action in connection with U.S. Appl. No. 11/400,497.
Aug. 8, 2006 Office Action in connection with U.S. Appl. No. 11/400,497.
May 29, 2001 Notice of Acceptance in connection with Australian Application No. 34026/97.
Sep. 28, 1999 Examiner's First Report in connection with Australian Application No. 34026/97.
Nov. 10, 2006 Official Action in connection with Canadian Application No. 2,257,991.
May 23, 2005 Communications Pursuant to Article 96(2) EPC in connection with European Application No. 97 930 120.7.
Nov. 17, 2004 Communication of partial European search report under Rule 45 EPC in connection with European Application No. 97 930 120.7.
Sep. 9, 2004 Communication of partial European search report under Rule 46(1) EPC in connection with European Application No. 97 930 120.7.
Oct. 17, 2006 Notification of Reasons for Rejection in connection with Japanese Application No. 501895/98 (English translation).
Apr. 5, 2004 Notice of Acceptance in connection with Australian Application No. 21996/00.

Feb. 5, 2003 Examiner's First Report in connection with Australian Application No. 21996/00.
Mar. 29, 2006 Examiner's First Report in connection with Australian Application No. 20004205164.
Mar. 29, 2006 Examiner's First Report in connection with Australian Application No. 20004205165.
Mar. 1, 2006 Communication under Rule 51(4) EPC in connection with European Application No. 99 966 466.7.
Jan. 10, 2005 Communication Pursuant to Article 96(2) EPC in connection with European Application No. 99 966 466.7.
Oct. 14, 2004 Communication Pursuant to Article 96(1) and Rule 51(1) EPC in connection with European Application No. 99 966 466.7.
Jan. 18, 2007 Office communication in connection with Mexican Application No. 1006097.
Oct. 13, 2005 Office communication in connection with Mexican Application No. 1006097.
Feb. 6, 2007 Notice of Allowability in connection with U.S. Appl. No. 09/464,902.
Jan. 8, 2007 Notice of Allowance and Allowability in connection with U.S. Appl. No. 09/464,902.
Apr. 19, 2006 Office Action in connection with U.S. Appl. No. 09/464,902.
Oct. 21, 2005 Office Action in connection with U.S. Appl. No. 09/464,902.
Jun. 15, 2005 Advisory Action in connection with U.S. Appl. No. 09/464,902.
Jan. 13, 2005 Final Office Action in connection with U.S. Appl. No. 09/464,902.
Apr. 2, 2004 Office Action in connection with U.S. Appl. No. 09/464,902.
Oct. 21, 2003 Office Action in connection with U.S. Appl. No. 09/464,902.
Sep. 25, 2001 Office Action in connection with U.S. Appl. No. 09/464,902.
Aug. 7, 2006 Office Action in connection with U.S. Appl. No. 09/594,983.
Mar. 24, 2006 Notice of Allowance and Allowability in connection with U.S. Appl. No. 09/594,983.
Jul. 11, 2005 Final Office Action in connection with U.S. Appl. No. 09/594,983.
Aug. 25, 2004 Office Action in connection with U.S. Appl. No. 09/594,983.
Sep. 23, 2003 Notice of Allowability in connection with U.S. Appl. No. 09/594,983.
Dec. 3, 2002 Final Office Action in connection with U.S. Appl. No. 09/594,983.
Mar. 13, 2002 Office Action in connection with U.S. Appl. No. 09/594,983.
Sep. 28, 2001 Office Action in connection with U.S. Appl. No. 09/594,983.
Dec. 19, 2006 Notice of Allowance and Allowability in connection with U.S. Appl. No. 10/763,545.
Jul. 26, 2006 Office Action in connection with U.S. Appl. No. 10/763,545.
Jun. 13, 2006 Office Action in connection with U.S. Appl. No. 10/763,545.
Feb. 16, 2006 Office Action in connection with U.S. Appl. No. 10/763,545.
May 16, 2006 Notice of Allowance and Allowability in connection with U.S. Appl. No. 10/371,483.
Oct. 24, 2006 Office Action in connection with U.S. Appl. No. 10/371,483.
Jan. 29, 2007 Examiner's First Report in connection Australian Application No. 2003217674.
Feb. 22, 2007 Communication Pursuant to Article 96(2) EPC in connection with European Application No. 03 713 632.2.
Apr. 21, 2006 Supplementary European search report under Article 15(2)(a) in connection with European Application No. 03 713 632.2.
Oct. 12, 2004 Communication Pursuant to Rules 109 and 110 EPC in connection with European Application No. 03 713 632.2.
Mar. 14, 2006 Examination Report in connection with New Zealand Application No. 534947.

(56) References Cited

OTHER PUBLICATIONS

Feb. 21, 2003 Official Action in connection with Russian Federation Application No. 2004128252/13(030609) (English Translation).
Sep. 29, 2006 Grant of Patent in connection with Singaporean Application No. 200404610-8.
Aug. 7, 2002 Office Action in connection with U.S. Appl. No. 09/663,219.
Jan. 5, 2006 Notice of Allowance and Allowability in connection with U.S. Appl. No. 09/912,824.
Jan. 26, 2005 Final Office Action in connection with U.S. Appl. No. 09/912,824.
Apr. 20, 2004 Office Action in connection with U.S. Appl. No. 09/912,824.
Jul. 2, 2003 Office Action in connection with U.S. Appl. No. 09/912,824.
Jul. 3, 2006 Notice of Acceptance in connection with Australian Application No. 2001290925.
Jun. 28, 2005 Examiner's First Report in connection with Australian Application No. 2001290925.
May 24, 2006 Supplementary European search report under Article 157(2) (a) EPC in connection with European Application No. 01970984.9.
Feb. 28, 2005 Formalities Examination in connection with European Application No. 01970984.9.
May 2, 2003 Communication Pursuant to Rules 109 and 110 EPC in connection with European Application No. 01970984.9.
Oct. 25, 2005 Notice of Allowance and Allowability in connection with U.S. Appl. No. 09/828,615.
Sep. 13, 2005 Office Action in connection with U.S. Appl. No. 09/828,615.
Mar. 2, 2005 Office Action in connection with U.S. Appl. No. 09/828,615.
Sep. 17, 2004 Final Office Action in connection with U.S. Appl. No. 09/828,615.
Feb. 23, 2004 Office Action in connection with U.S. Appl. No. 09/828,615.
Sep. 9, 2003 Advisory Action in connection with U.S. Appl. No. 09/828,615.
Feb. 21, 2003 Final Office Action in connection with U.S. Appl. No. 09/828,615.
Jun. 25, 2002 Office Action in connection with U.S. Appl. No. 09/828,615.
Jun. 9, 2005 Notice of Allowance and Allowability in connection with U.S. Appl. No. 10/116,797.
Apr. 25, 2005 Final Office Action in connection with U.S. Appl. No. 10/116,797.
Oct. 6, 2004 Office Action in connection with U.S. Appl. No. 10/116,797.
Feb. 9, 2004 Office Action in connection with U.S. Appl. No. 10/116,797.
Genbank Sequence Report, Accession Entry X91492 for *H. sapiens* Chem13, submitted Sep. 14, 1995.
Janeway and Travers (1994). Immunobiology, Current Biology Ltd., San Francisco. pp. 10:27-10:42.
Stryer (1988). Biochemistry, 3rd edition. pp. 984-988.
Dec. 17, 2003 Third Party Observations in connection with European Application No. 97904948.3.
Feb. 27, 2004 Third Party Observations in connection with European Application No. 97904948.3.
Abaza, M.S.I. and Astassi, M.Z. (1992). Effects of Amino Acid Substitutions Outside an Antigenic Site on Protein Binding to Monoclonal Antibodies of Predetermined Specificity Obtained by Peptide Immunization: Demonstration With Region 94-100 (Antigenic Site 3) of Myoglobin. J. Prot. Chem., 11(5):433-443.
Alkhatib, et al. (1996). Abstract At 3rd Conference on Retroviruses.
Alkhatib, G., et al. (1996). CC CKR5: A Rantes, MIP-1a, MIP-1β Receptor As a Fusion Cofactor for Macrophage-Tropic HIV-I. Science, 272:1955-1958.

Alkhatib, G., et al. (1997). HIV Co-Receptor Activity of CCR5 and Its Inhibition by Chemokines: Independence From G Protein Signaling and Importance of Co-Receptor Down Modulation. Virology, 234:340-348.
Allaway, G.P., et al. (1993). Synergistic Inhibition of HIV-1 Envelope-Mediated Cell Fusion by CD4-Based Molecules in Combination With Antibodies to gp120 or gp41. AIDS Res. Hum. Retroviruses, 9:581-587.
Allaway, G.P., (1995). Expression and Characterization of CD4-IgG2, A Novel Heterotetramer That Neutralizes Primary HIV Type 1 Isolates. AIDS Res. Hum. Retrovirus, 11:533-539.
Amara, A., et al. (1997). HIV Coreceptor Downregulation As Antiviral Principle: SDF-La-Dependent Internalization of the Chemokine Receptor CXCR4 Contributes to Inhibition of HIV Replication. J. Exp. Med., 186:139-146.
Arenzana-Selsdedos, F., et al. (1996). HIV Blocked by Chemokine Antagonist. Nature, 383:400.
Arthos, J., et al. (1989). Identification of the Residues in Human CD4 Critical for the Binding of HIV. Cell, 57:469-481.
Ashorn, P.A., et al. (1990). Human Immunodeficiency Virus Envelope Glycoprotein/CD4 Mediated Fusion of Nonprimate Cells With Human Cells. J. Virol., 64:2149-2156.
Attanasio, et al. (1991). Anti-Idiotypic Antibody Response to Monoclonal Anti-CD4 Preparations in Nonhuman Primate Species. J. Immunol., 146:507-514.
Baba et al. (1998). Mechanism of Inhibitory Effect of Dectran Sulfate and Heparin on Replication of Human Immunodeficiency Virus In Vitro. Proc. Natl. Acad. Sci., 85:6132-6135.
Back, D.J. (1999). Pharmacological Issues Relating to Viral Resistance. Infection, 27(Suppl.2):S42-S44.
Balzarini, et al. (1995). Suppression of the Breakthrough of HIV-1 in Cell Culture by Thiocarboxanilide Derivatives When Used Individually or in Combination With Other HIV-1-Specific Inhibitors. Proc. Natl. Acad. Sci., 92:5470-5474.
Baulerle and Huttner (1987). Tyrosine Sulfation Is a Trans-Golgi-Specific Protein Modification. Cell. Biol., 105:2655-2663.
Berger, et al. (1996). Abstract No. 002, 8 at Keystone Symposium.
Berger E.A. (1997). HIV Entry and Tropism: The Chemokine Receptor Connection. AIDS, 11 (Suppl.A):S3-S16.
Berger, et al. (1999). Chemokine Receptors As HIV-1 Coreceptors: Roles in Viral Entry, Tropism and Disease. Ann. Rev. Immunol., 17:657-700.
Bieniasz, P.D., et al. (1997). HIV-1 Induced Cell Fusion is Mediated by Multiple Regions Within Both the Viral Envelope and the CCR5 Co-Receptor. EMBO, 16:2599-2609.
Blanpain, C., et al. (1999). Multiple Charged and Aromatic Residues in CCR5 Amino-Terminal Domain Are Involved in High Affinity Binding of Both Chemokines and HIV-1 Env Protein. J. Biol. Chem., 274:34719-34727.
Bleul, C.C., et al. (1991). The Lymphocyte Chemoattractant SDF-1 is a Ligand for LESTR/Fusion and Blocks HIV-1 Entry. Nature, 382:829-832.
Brelot, A., et al. (1997). Role of the First and Third Extracellular Domains of CXCR4 in Human Immunodeficiency Virus Coreceptor Activity. J. Virol., 71:4744-4751.
Brenner, T.J., et al. (1996). Relation Between HIV-1 Syncytium Inhibition Antibodies and Clinical Outcome in Children. Lancet, 337:1001-1005.
Broder, et al. (1993). The Block to HIV-1 Envelope Glycoprotein-Mediated Membrane Fusion in Animal Cells Expressing Human CD4 Can Be Overcome by a Human Cell Component(S). Virol., 193:483-491.
Broder, et al. (1996). HIV and the 7-Transmembrane Domain Receptors. Pathobiology, 64(4):171-179.
Burkly, L., et al. (1995). Synergistic Inhibition of Human Immunodeficiency Virus Type 1 Envelope Glycoprotein-Mediated Cell Fusion and Infection by an Antibody to CD4 Domain 2 in Combination With Anti-Gp-120 Antibodies. J. Virol., 69:4267-4273.
Burton, D.R., et al. (1994). Efficient Neutralization of Primary Isolates of HIV-1 by a Recombinant Human Monoclonal Antibody. Science, 266:1024-1027.

(56) References Cited

OTHER PUBLICATIONS

Busso, et al. (1991). HIV-Induced Syncytium Formation Requires the Formation of Conjugates Between Virus-Infected and Uninfected T-Calls In Vitro. AIDS, 5:1425-1432.
Cammack, N. (1999). Human Immunodeficiency Virus Type 1 Entry and Chemokine Receptors: A New Therapeutic Target. Antiviral Chemistry and Chemotherapy, 10:53-62.
Capon, D.J., et al. (1989). Designing CD4 Immunoadhesions for AIDS Therapy. Nature, 337:525-531.
Chan, D.C., et al. (1998). Evidence That a Prominent Cavity in the Coiled Coil of HIV Type 1 Gp41 is an Attractive Drug Target. Proc. Natl. Acad. Sci., 95:15613-15617.
Chan, D.C., et al. (1998). HIV Entry and Its Inhibition. Cell, 93:681-684.
Charo, et al. (1994). Molecular Cloning and Functional Expression of Two Monocyte Chemoattractant Protein 1 Receptors Reveals Alternative Splicing of the Carboxyl-Terminal Tails. Proc. Natl. Acad. Sci., 91:2752-2756.
Chen et al. (1997). Genetically Divergent Strains of Simian Immunodeficiency Virus Use CCR5 as a Coreceptor for Entry. J. of Viral., 71(4):2705-2714.
Choe, H., et al. (1996). The Beta-Chemokine Receptors CCR3 and CCR5 Facilitate Infection by Primary HIV-1 Isolates. Cell, 85:1135-1148.
Clapham, P.R., et al. (1991). Specific Cell Surface Requirements for the Infection of CD4-Positive Cells by Human Immunodeficiency Virus Types 1 and 2 by Simian Immunodeficiency Virus. Virol., 181:703-715.
Co, et el. (1991). Humanized Antibodies for Antiviral Therapy. Proc. Natl. Acad. Sci., 88:2869-2873.
Cocchi, F. (1995). Identification of RANTES, MIP-1alpha and MIP-1beta As the Major HIV-Suppressive Factors Produced by CD8+ T-Cells. Science, 270:1811-1815.
Combadiere, et al. (1995). Cloning and Functional Expression of a Human Eosinophil CC Chemokine Receptor. J. Biol. Chem., 270, 16491-16494 (Note—Erratum In: J. Biol. Chem. Dec. 15, 1995;270 (50) :30235).
Combadiere, et al. (1996). Cloning and Functional Expression of CC CKR5, A Human Monocyte CC Chemokine Receptor Selective for MIP-1a, MIP-1β and RANTES. J. Leukos. Biol., 60:147-152.
Connor, R.I, et al., (1997). Change in Co-Receptor Use Correlates With Disease Progression in HIV-1 Infected Individuals. J. Exp. Med., 185:621-628.
Cormier, E.G., et al. (2000). Specific Interaction of CCR5 Amino-Terminal Domain Peptides Containing Sulfotyrosines With HIV-1 Envelope Glycoprotein Gp120. Proc. Natl. Acad. Sci., 97:5762-5767.
Crump, M.P., et al. (1997). Solution Structure and Basis for Functional Activity of Stromal-Cell Derived Factor-1: Disassociation of CXCR4 Activation From Binding and Inhibition of HIV-1. EMBO, 16:6996-7007.
Cruse, et al. (1995). Illustrated Dictionary of Immunology, CRC Press, Inc, Boca Raton, FL., 143:QR180.4.C78.
Cushman, M., et al. (1991). Preparation and Anti-HIV Activities of Aurintricarboxylic Acid Fractions and Analogues: Direct Correlation of Antiviral Potency With Molecular Weight. J. Med. Chem., 34:329-337.
Daar, E.S. (1990). High Concentrations of Recombinant Soluble CD4 are Required to Neutralize Primary Human Immunodeficiency Virus Type 1 Isolates. Proc. Natl. Acad. Sci., 87:6574-6578.
Dalgleish, A.G., et al. (1984). The CD4 (T4) Antigen is an Essential Component of the Receptor for the AIDS Retrovirus. Nature, 312:763-766.
Dalgleish, A.G. (1995). HIV and CD26. Nature Medicine, 1:881-882.
De Rossi, A., et al. (1995). Synthetic Peptides From the Principle Neutralizing Domain of Human Immunodeficiency Virus Type 1 (HIV-1) Enhance HIV-1 Infection Through a CD4-Dependent Mechanism. Virology, 184:187-19.

Dean, M., et al. (1996). Genetic Restriction of HIV-1 Infection and Progression to AIDS by a Deletion Allele of the CKR5 Structural Gene. Science, 273:1856-1862.
De Clerq, et al. (1992). Potent and Selective Inhibition of Human Immunodeficiency Virus (HIV)-1 and HIV-2 Replication by a Class of Bicyclams Interacting With a Virus Uncoating Event. Proc. Natl. Acad. Sci., 89:5286-5290.
De Clerq, et al. (1994). Highly Potent and Selective Inhibition of Human Immunodeficiency Virus by the Bicyclam Derivative JM3100. Antimicrobial Agents and Chemotherapy, 38:668-674.
De Clerq, et al. (1995). Antiviral Therapy for Human Immunodeficiency Virus Infections. J. Clin. Microbial. Rev., 8(2):200-239.
Deen, K.C., et al. (1988). A Soluble Form of CD4(T4) Protein Inhibits AIDS Virus Infection. Nature, 331:82-84.
Deng, H., et al. (1996). Identification of a Major Co-Receptor for Primary Isolates of HIV-1. Nature, 381:661-666.
Deng, X., et al. (1999). A Synthetic Peptide Derived From Human Immunodeficiency Virus Type 1 Gp120 Down-Regulates the Expression and Function of Chemokine Receptors CCR5 and CXCR4 in Monocytes by Activating the 7-Transmembrane G-Protein-Coupled Receptor FPRL1/LXA4R. Blood, 94(4):1165-1173.
Dettin, et al. (2003). CCR5 N-Terminus Peptides Enhance X4 HIV-1 Infection by CXCR4 Up-Regulation. Biochem. Biophys. Res. Commun., 307(3):640-646.
Dikic (1996). Regulation of HIV-1 Infection by Chemokine Receptors. Acta Med. Croatica, 50:163-168.
Ditzel, et al. (1998). The CCR5 Receptor Acts as an Alloantigen in CCR5Δ32 Homozygous Individuals: Identification of Chemokine and HIV-1 Blocking Human Antibodies. Proc. Natl. Acad. Sci., 95(9):5241-5245.
Donzella, G.A., et al. (1998). AMD3100, A Small Molecule Inhibitor of HIV-1 Entry Via the CXCR4 Co-Receptor. Nat. Med., 4:72-77.
Doranz, B.J., et al. (1996). A Dual-Tropic Primary HIV-1 Isolate That Uses Fusin and Beta-Chemokine Receptors CKR-5, CKR-3 and CKR-2b As Fusion Cofactors. Cell, 85:1149-1158.
Doranz, B.J., et al. (1997). Two Distinct CCR5 Domains Can Mediate Co-Receptor Usage by Human Immunodeficiency Virus Type 1. J. Virol., 71:6305-6314.
Doranz, B.J., et al. (1997). A Small Molecule Inhibitor Directed Against the Chemokine Receptor CXCR4 Prevents Its Use As an HIV-1 Co-Receptor. J. Ex. Med., 186:1395-1400.
Dragic, T.V., et al. (1995). Proteinase-Resistant Factors in Human Erythrocyte Membranes Mediated CD-4 Dependent Fusion With Cells Expressing Human Immunodeficiency Virus Type 1 Envelope Glycoproteins. J. Virol., 69:1013-1018.
Dragic, T.V., et al. (1996). HIV-1 Entry Into CD4+ Cells Is Mediated by the Chemokine Receptor CC-CKR-5. Nature, 381:667-673.
Dragic, T.V., et al. (1998). Amino-Terminal Substitutions in the CCR5 Coreceptor Impair Gp120 Binding and Human Immunodeficiency Virus Type 1 Entry. J. Virol., 72(1):279-285.
Dragic, et al. (2000). A Binding Pocket for a Small Molecule Inhibitor of HIV-1 Entry Within the Transmembrane Helices of CCR5. Proc. Natl. Acad. Sci., 97(10):5639-5644.
Eckert, D.M., et al. (1999). Inhibiting HIV-1 Entry: Discovery of D-Peptide Inhibitors That Target the gp41 Coiled-Coil Pocket. Cell, 99:103-115.
Eugen-Olsen, J., et al. (1997). Heterozygosity for a Deletion in the CKR-5 Gene Leads to Prolonged AIDS-Free Survival and Slower CD4 T-Cell Decline in a Cohort of HIV-Seropositive Individuals. AIDS, 11:305-310.
Fahey, J.L., et al. (1992). Status of Immune-Based Therapies in HIV Infection and AIDS. Clin. Exp. Immunol., 88:1-5.
Farzan, M., et al. (1998). A Tyrosine-Rich Region in the N-Terminus of CCR5 is Important for Human Immunodeficiency Virus Type 1 Entry and Mediates Association Between gp120 and CCR5. J. Virol., 72:1160-1164.
Farzan, M., et al. (1999). Tyrosine Sulfation of the Amino-Terminus of CCR5 Facilitates HIV-1 Entry. Cell, 96:667-676.
Farzan, M., et al. (2000). A tyrosine-sulfated peptide based on the N terminus of CCR5 interacts with a CD4-enhanced epitope of the HIV-1 gp 120 Envelope Glycoprotein and Inhibits HIV-1 Entry. J. Biol. Chem., 275:33416-33521.

(56) References Cited

OTHER PUBLICATIONS

Feng, et al. (1996). Abstract No. 116,21 at Keystone Symposium.
Feng, Y., et al. (1996). HIV-1 Entry Cofactor: Functional cDNA Cloning of a Seven-Transmembrane, g Protein-Coupled Receptor. Science, 272:872-877.
Ferrer, M., et al. (199g). Selection of gp-41 Mediated HIV-1 Cell Entry Inhibitors From Biased Combinatorial Libraries of Non-Natural Binding Elements. Nature. Struct. Biol., 6:953-959.
Flexner, C. and Hendrix, C. (1997). "Pharmacology of Antiretroviral Agents", in AIDS: Biology, Diagnosis, Treatment and Prevention, 4th Edition, De Vita V., et al. eds., Lippincott-Raven Publishers. pp. 479-493.
Fouts, T.R., et al. (1997). Neutralization of the Human Immunodeficiency Virus Type 1 Primary Isolate JR-FL by Human Monoclonal Antibodies Correlates With Antibody Binding to the Oligomeric Form of the Envelope Glycoprotein Complex. J. Virol., 71:2779-2785.
Fox, J.L. (1994). No Winners Against Aids. Bio/Technology, 12:128.
Fradd, F. and Mary, M.E. (1989). AIDS Vaccines: An Investor's Guide, Shearman Lehaman Hutton. p. 10:(Fig. 2).
Furuta, R.A., et al. (1998). Capture of an Early Fusion-Active Conformation of HIV-1 gp41. Nature Struct. Biol., 5(4):276-279.
Gait, M.J and Karn, J. (1995). Progress in anti-HIV Structure Based Drug Design. TIBTECH, 13:430-438.
Gauduin, M.C., et al. (1996). Effective Ex Vivo Neutralization of Plasma HIV-1 by Recombinant Immunoglobulin Molecules. J. Virol., 70:2586-2592.
Gauduin, M.C., et al. (1997). Passive Immunization With a Human Monoclonal Antibody Protects hu-PBL-SCID Mice Against Challenge by Primary Isolates of HIV-1. Nature Medicine, 3:1389-1393.
Ghorpade A., et al. (1998). Role of the Beta-Chemokine Receptors CCR3 and CCR5 in Human Immunodeficiency Virus Type 1 Infection of Monocytes and Microglia. J. Virol, 72:3351-3361.
Golding, H., et al. (1992). LFA-1 Adhesion Molecules Are Not Involved in the Arly Stages of HIV-1 ENV-Mediated Cell Membrane Fusion. AIDS Res. Hum. Retroviruses, 8:1593-1598.
Gong, J.H., et al. (1995). Antagonists of Monocyte Chemoattractant Protein 1 Identified by Modification of Functionally Critical NH2-Terminal Residues. J. Exp. Med., 181:631-640.
Gong, J.H., et al. (1996). RANTES and MCP-3 Antagonists Bind Multiple Chemokine Receptors. J. Biol. Chem., 371:10521-10527.
Grene, et al. (2001). Anti-CCR5 Antibodies in Sera of HIV-Positive Individuals. Human Immunol., 62(2):143-145.
Harrington, R.D. and Geballe, A.P. (1993). Cofactor Requirement for Human Immunodeficiency Virus Type 1 Entry Into a CD4-Expressing Human Cell Line. J. Virol., 67:5939-5947.
Hattori, T., et al. (1989). Involvement of Tryptase-Related Cellular Protease(S) In Human Immunodeficiency Virus Type 1 Infection. FEBS Letters, 248:48-52.
Haynes, B.F. (1996). Updates on the Issues of HIV Vaccine Development. Ann. Med., 28:39-41.
He, Jianglin, et al. (1997). CCR3 and CCR5 are Co-Receptors for HIV-1 Infection of Microglia. Nature, 385:645-649.
Heath, et al. (1997). Chemokine Receptor Usage by Human Eosinophils. The Importance of CCR3 Demonstrated Using an Antagonistic Monoclonal Antibody. J. Clin. Invest., 99:178-184.
Heidenreich, et al. (1995). Application of Antisense Technology to Therapeutics. Mol. Med. Today, 1:128-133.
Hildreth, et al. (1989). Involvement of a Leukocyte Adhesion Receptor (LFA-1) in HIV-Induced Syncytium Formation. Science, 244:1075-1078.
Hill, C.M., et al. (1998). The Amino Terminus of Human CCR5 Is Required for Its Function As a Receptor to Diverse Human and Simian Immunodeficiency Virus Envelope Glycoproteins. Virology, 248:357-371.
Hirata, Y. (1989). Characterization of IL-6 Receptor Expression by Monoclonal and Polyclonal Antibodies. J. Immun., 2900-2906.
Howard, O.M.Z., et al. (1998). Small Molecule Inhibitor of HIV-1 Cell Fusion Blocks Chemokine Receptor-Mediated Fusion. J. Leuk. Biol., 64:6-13.

Hwang, S.S., et al. (1991). Identification of the Envelope V3 Loop as the Primary Determinant of Cell Tropism in HIV-1. Science, 253:71-74.
Jacobson, J.M., et al. (1993). Passive Immunotherapy in the Treatment of Advanced Human Immunodeficiency Virus Infection. J. Infect. Dis., 168:298-305.
Jacobson, J., et al. (1999). Results of a Phase I Trial of Single-Dose PRO 542, A Novel Inhibitor of HIV Entry. Abstracts of the 39th Interscience Conference on Antimicrobial Agents and Chemotherapy 14.
Ji, H., et al. (1999). Inhibition of Human Immunodeficiency Virus Type 1 Infectivity by the gp41 Core: Role of a Conserved Hydrophobic Cavity in Membrane Fusion. J. Virol., 73:8578-8586.
Jiang, S., et al. (1993). HIV-1 Inhibition by a Peptide. Nature, 365:113.
Jones, S.A., et al. (1997). Chemokine Antagonists That Discriminate Between Interleukin-8 Receptors. J. Biol. Chem., 272:16166-16199.
Karwowska, S., et al. (1991). Passive Immunization for the Treatment and Prevention of HIV Infection. Biotech. Therap., 2:31-48.
Katinger, H. (1994). Human Monoclonal Antibodies for Passive Immunotherapy of HIV-1. Antibiot. Chemother., 46:23-37.
Kilby, J.M., et al. (1998). Potent Suppression of HIV-1 Replication in Humans by T-20, A Peptide Inhibitor of gp41-Mediated Virus Entry. Nature Med., 4:1302-1307.
Klotman, et al. (1995). Transgenic Models of HIV-1. AIDS, 9(4):313-324.
Konigs, C., et al. (2000). Monoclonal Antibody Screening of Phage-Displayed Random Peptide Library Reveals Mimotopes of Chemokine Receptor CCR5: Implications for the Tertiary Structure of the Receptor and for an N-Terminal Binding Site for HIV-1 gp120. Eur. J. Immnol., 30(4):1162-1171.
Konishi, K., et al. (2000). Synthesis of Peptides Mimicking Chemokine Receptor CCR5 and Their Inhibitory Effects Against HIV-1 Infection. Chem. Pharm. Bull., Tokyo, 48(2):308-309.
Koup, R.A., et al. (1996). Defining Antibody Protection Against HIV-1 Transmission in Hu-PBL-SCID Mice. Immunology, 8:263-268.
Kwong, P.D. et al. (1998). Structure of an HIV gp120 Envelope Glycoprotein in Complex With the CD4 Receptor and Neutralizing Human Antibody. Nature, 393:648-659.
Laal, S., et al. (1994). Synergistic Neutralization of Human Immunodeficiency Virus Type 1 by Combinations of Human Monoclonal Antibodies. J. Virol., 68:4001-4008.
LaCasse, R.A., et al. (1999). Fusion-Competent Vaccines: Broad Neutralization of Primary Isolates of HIV. Science, 283:357-362.
Lee, B., et al. (1999). Epitope Mapping of CCR5 Reveals Multiple Conformational States and Distinct But Overlapping Structures Involved in Chemokine Coreceptor Function. J. Biol. Chem., 9617-9626.
Lehner, et al. (2001). Immunogenicity of the Extracellular Domains of C—C Chemokine Receptor 5 and the In Vitro Effects on Simian Immunodeficiency or HIV Infectivity. Journal of Immunology, 166(12):7446-7455.
Levy, J.A. (1996). Controlling HIV Pathogenesis: The Role of the Non-Cytotoxic Anti-HIV Response of CD8+ Cells. Immunology Today, 17:217-224.
Li, A., et al. (1997). Synergistic Neutralization of Chimeric SIV/HIV Type 1 Virus With Combinations of Human Anti-HIV Type 1 Envelope Monoclonal Antibodies or Hyperimmune Globulins. AIDS Res. Hum. Retroviruses, 12:647-56.
Li, A.H., et al. (1998). Synergistic Neutralization of Simian-Human Immunodeficiency Virus SHIV-vpu+ by Triple and Quadruple Combination of Human Monoclonal Antibodies and High-Titer Antihuman Immonodeficiency Virus Type 1 Immunoglobulins. J. Virol., 72:3235-3240.
Litwin, V.M., et al. (1996). Human Immunodeficiency Virus Type 1 Membrane Fusion Mediated by a Laboratory-Adapted Strain and a Primary Isolate Analyzed by Resonance Energy Transfer. J. Virol., 70(9):6437-6441.
Loetscher, M., et al. (1994). Cloning of a Human Seven-Transmembrane Domain Receptor, LESTR, That Is Highly Expressed in Leukocytes. J. Biol. Chem., 269:232-237.

(56) References Cited

OTHER PUBLICATIONS

Mack, M., et al. (1998). Aminooxypentane-RANTES Induces CCR5 Internalization But Inhibits Recycling: A Novel Inhibitory Mechanisms of HIV Infectivity. J. Ex. Med., 187:1215-1224.

Mackay, C.R. (1996). Chemokine Receptors and T Cell Chemotaxis. J. Exp. Med., 84:799-802.

Maddon, P.J., et al. (1986). The T4 Gene Encodes the AIDS Virus Receptor and Is Expressed in the Immune System and the Brain. Cell, 47:333-348.

Markosyan, R.M., et al. (2002). The Mechanism of Inhibition of HIV-1 Entry Env-Mediated Cell-Cell Fusion by Recombinant Cores of gp41 Ectodomain. Virology, 302:174-184.

McKnight, A.D., et al. (1997). Inhibition of Human Immunodeficiency Virus Fusion by a Monoclonal Antibody to a Coreceptor (CXCR4) Is Both Cell Type and Virus Strain Dependent. J. Virol., 71:1692-1696.

Mellors, J.W. (1996). Closing in on Human Immunodeficiency Virus-1. Nature Medicine, 2(3):274-275.

Mohan, P., et al. (1992). Sulfonic Acid Polymers As a New Class of Human Immunodeficiency Virus Inhibitors. Antiviral Res., 18:139-150.

Moser, B., et al. (1993). Interleukin-8 Antagonists Generated by N-Terminal Modification. J. Biol. Chem., 268:7125-7128.

Mosier, D.E. (1990). Immunodeficient Mice Xenografted With Human Lymphoid Cells: New Models for In-Vivo Studies of Human Immunobiology and Infectious Diseases. J. Clin. Immuno., 10(4):185-191.

Nagasawa, et al. (1994). Molecular Cloning and Structure of a Pre-B-Cell Growth-Stimulating Factor. Proc. Natl. Acad. Sci., 91:2305-2309.

Nagashima, K.A., et al. (2001). Human Immunodeficiency Virus Type 1 Entry Inhibitors PRO 542 and T-20 are Potently Synergistic in Blocking Virus-Cell and Cell-Cell Fusion. J. Infect. Dis., 183:1121-1125.

Nakano, T., et al. (1995). Vascular smooth muscle cell-derived, Gla-containing growth-potentiating factor for Ca2+ mobilizing growth factors. J. Biol. Chem., 270(11):5702-5705.

Neote, et al. (1993). Molecular cloning, functional expression, and signaling characteristics of a C—C chemokine receptor. Cell, 72:415-425.

Oberg, B and Vrang, L. (1990). Screening for new agents. Eur. J. Clin. Microbiol. Infect. Dis., 9(7):466-471.

Oberlin, E., et al. (1996). The CXC Chemokine SDF-1 is the Ligand for LESTR/fusion and prevents infection by T-cell-line-adapted HIV-1. Nature, 382: 833-835.

Oellerich, M., (1984). Enzyme-Immunoassay: A Review. J. Clin. Chem. Clin. Biochem., 22(12):895-904.

Olson, et al., (1999). Differential Inhibition of Human Immunodeficiency Virus Type 1 Fusion, gp120 Binding and CC-chemokine Activity of Monoclonal Antibodies to CCR5. J. Virol., 73:4145-4155.

Opperman, (2004). Chemokine Receptor CCR5: Insights Into Structure, Function, and Regulation. Cell. Signal., 16:1201-1210.

Parren, et al. (2001). Antibody Protects Macaques Against Vaginal Challenge With a Pathogenic R5 Simian/Human Immunodeficiency Virus at Serum Levels Giving Complete Neutralization In Vitro. J. Virol., 75:8340-8347.

Partidos, C., et al. (1992). The Effect of Orientation of Epitopes on the Immunogenicty of Chimeric Synthetic Peptides Representing Measles Virus Protein Sequences. Molecular Immunology, 29(5):651-658.

Poignard, P., et al. (1999). Neutralizing Antibodies Have Limited Effects on the Control of Established HIV-1 Infection In-Vivo. Immunity, 10:431-438.

Posner, M.R., et al. (1993). Neutralization of HIV-1 by F105, A Human Monoclonal Antibody to the CD4 Binding Site of gp120. J. Acq. Immune Defic. Synd., 6:7-14.

Power, et al. (1995). Molecular Cloning and Functional Expression of a Novel CC Chemokine Receptor Cdna From a Human Basophilic Cell Line. J. Biol. Chem., 270:1811-1815.

Proudfoot, et al. (1996). Extension of Recombinant Human RANTES by the Retention of the Initiating Methionine Produces a Potent Antagonist. J. Biol. Chem., 271:2599-2603.

Proudfoot, et al. (1999). Chemokine Receptors: Future Therapeutic Targets for HIV. Biochem. Pharmacol., 57:451-463.

Proudfoot, et al. (2000). The Strategy of Blocking the Chemokine System to Combat Disease. Immunol. Rev., 177:246-256.

Queen, et al. (1989). A Humanized Antibody That Binds to the Interleukin 2 Receptor. Proc. Natl. Acad. Sci, 86:10029-10033.

Rabut, G.E., et al. (1991). Alanine Substitutions of Polar and Nonpolar Residues in the Amino-Terminal Domain of CCR5 Differently Impair Entry of Macrophage and Dualtropic Isolates of Human Immunodeficiency Virus Type 1. J. Virol., 72:3464-3468.

Raport, C.J., et al. (1996). Molecular Cloning and Functional Characterization of a Novel Human CC-Chemokine Receptor (CCR5) for RANTES, MIP-1β, and MIP-1a. J. Biol. Chem., 271:1761-1766.

Raport, C.J., et al. (1996). New Members of the Chemokine Receptor Gene Family. Journal of Leukocyte Biology, 59:18-23.

Raport, C.J., et al. (1996). AAC50598 submitted to NCBI on Apr. 12, 1996 (CC Chemokine Receptor 5 sequence).

Richman, D.D. (1996). Antiretroviral Drug-Resistance: Mechanisms, Pathogenesis, Clinical Significance. Antivir. Chemother., 4:383-395.

Rodriguez, G., et al. (1995). Mediation of Human Immunodeficiency Virus Type 1 Binding by Interaction of Cel Surface Heparin Sulfate Proteoglycans With V3 Region of Envelope gp120-gp41. J. Virol., 69:2233-2239.

Rucker, et al. (1996). Regions in Beta-Chemokine Receptors CCR5 and CCR2b That Determine HIV-1 Cofactor Specificity. Cell, 87:437-446.

Ruffing, et al. (1998). CCR5 Has an Expanded Ligand-Binding Repertoire and is the Primary Receptor Used by MCP-2 on Activated T-Calls. Cell. Immunol., 160:160-168.

Rudikoff, et al. (1982). Single Amino Acid Substitution Altering Antigen-Binding Specificity. Proc. Natl. Acad. Sci., 79:1979-1983.

Samson, M., et al. (1996). Molecular Cloning and Functional Expression of a New Human CC-Chemokine Receptor Gene. Biochem., 35:3362-3367.

Sandberg, J. (1995). Developmental Pharmacology and Toxicology of Anti-HIV Therapeutic Agents: Dideoxynucleosides. FASEB J., 9:1157-1163.

Sato, et al. (1992). Anti-Cd7 Reagents Inhibit HIV-1 Induced Syncytium Formation. International Conference on AIDS, 81. PA5 PoA 2017.

Sato, et al. (1994). Identification of CD7 Glycoprotein as an Accessory Molecule in HIV-1 Mediated Syncytium Formation and Cell Free Infection. J. Immunol., 152:5142-5152.

Sato, et al. (1995). A Simple and Rapid Method for Preliminary Evaluation of In Vivo Efficacy of Anti-HIV Compounds in Mice. Antivir. Res., 27:151-163.

Scarlatti, et al. (1997). In Vivo Evolution of HIV-1 Co-Receptor Usage and Sensitivity to Chemokine-Mediated Suppression. Nature Medicine, 3(11):1259-1265.

Schanberg, et al. (1995). Characterization of Human CD7 Transgenic Mice. J. of Immunol., 155:2407-2418.

Schols, D., et al. (1990). Dextran sulfate and other olyanionic anti-HIV compounds specifically interact with the viral gp120 Glycoprotein Expressed by T-Cells Persistently Infected With HIV-1. Virology, 175:556-561.

Schols, D., et al. (1991). Selective Inhibitory Activity of Polyhydroxycarboxylates Derived From Phenolic Compounds Against Human Immunodeficiency Virus Replication. J. Acq. Immune Defic. Synd., 4:677-685.

Schols, D., et al. (1999). CD26-Processed RANTES(3-68), But Not Intact RANTES, Has Potent Anti-HIV-1 Activity. Antiviral Res., 30:175-187.

Simmons, G., et al. (1997). Potent Inhibition of HIV-1 Infectivity in Macropages and Lymphocytes by a Novel CCR5 Antagonist. Science, 276:276-279.

Sommerfelt, M.A., et al. (1995). Intercellular Adhesion Molecule 3, A Candidate Human Immunodeficiency Virus Type 1 Co-Receptor on Lymphoid and Monocytoid Cells. J. Gen. Virol., 76:1345-1352.

(56) References Cited

OTHER PUBLICATIONS

Steinberger, P., et al. (2000). Generation and Characterization of a Recombinant Human CCR5-Specific Antibody. J. Biol. Chem., 275:36073-36078.
Stewart, G.J. (1997). Increased Frequency of CCR-5Δ32 Heterozygotes Among Long-Term Non-Progressors With HIV-1 Infection. AIDS, 11:1833-1838.
Strizki, J.M., et al. (1997). A Monoclonal Antibody (12G5) Directed Against CXCR4 Inhibits Infection With the Dual-Tropic Human Immunodeficiency Virus Type 1 Isolates HIV-1 89.6 But Not the T-Tropic Isolate HIV-1 HxB. J. Virol., 71:5678-5683.
Su, et al. (1996). Preparation of Specific Polyclonal Antibodies to a C—C Chemokine Receptor, CCR1, and Determination of CCR1 Expression on Various Types of Leukocytes. J. Leukos. Biol., 60:658-666.
Thali, M., et al. (1992). Cooperativity of Neutralizing Antibodies Directed Against the VS and CD4 Binding Regions of the Human Immunodeficiency Virus gp120 Envelope Glycoprotein. J. Acq. Immune. Defic. Synd., 5:591-599.
Tilley, S.A., et al. (1991). Potent Neutralization of HIV-1 by Human and Chimpanzee Monoclonal Antibodies Directed Against Three Distinct Epitope Clusters of gp120. Sixieme Colloque Des Cent Gardes., 211-216.
Tremblay, et al. (2000). Strong In Vitro Synergy Observed Between the Fusion Inhibitor T-20 and a CXCR4 Blocker AMD-3100. Feb. 7, 2000 Conference on Retroviruses and Opportunistic Infections, abstract 500.
Tremblay, et al. (1999). Strong In Vitro Synergy Between the Fusion Inhibitor T-20 and the CXCR4 Blocker AMD-3100. Journal of Acquired Immune Deficiency Syndromes, 25(2):99-102.
Trkola, A., et al. (2001). Potent, Broad-Spectrum Inhibition of Human Immunodeficiency Virus Type 1 by the CCR5 Monoclonal Antibody PRO 140. J. Virol., 75:579-588.
Trkola, A., et al. (1999). Cross-Glade Neutralization of Primary Isolates of Human Immunodeficiency Virus Type 1 by Human Monoclonal Antibodies and Tetrameric CD4-IgG. J. Virol., 73(5):4145-4155.
Trkola, A., et al. (1996). CD-4 Dependent, Antibody Sensitive Interactions Between HIV-1 and Its Co-Receptor CCR-5. Nature, 384:184-187.
Trkola, A., et al. (1998). Neutralization Sensitivity of Human Immunodeficiency Virus Type 1 Primary Isolates to Antibodies and CD40 based Reagents Is Independent of Coreceptor Usage. J. Virol., 72:1876-1885.
Tulip, W.R., et al. (1992). Crystal Structures of Two Mutant Neraminidase-Antibody Complexes With Amino Acid Substitutions in the Interface. J. Mol. Biol., 227:149-159.
Valentin, et al. (1990). The Leukocyte Adhesion Glycoprotein CD18 Participates in HIV Induced Syncyia Formation in Monocytoid and T Cells. J. of Immunology, 144:934-937.
Valenzuela, A., et al. (1997). Neutralizing Antibodies Against the V3 Loop of Human Immunodeficiency Virus Type 1 Block the CD4-Dependent and Independent Binding of Virus to Cells. J. Virol., 71(11):8289-8298.
Vijh-Warrier, S., Pinter, A., Honnen, W.J., and Tilley, S.A. (1996). Synergistic Neutralization of Human Immunodeficiency Virus Type 1 by a Chimpanzee Monoclonal Antibody Against the V2 Domain of gp120 in Combination With Monoclonal Antibodies Against the V3 Loop and the CD4-Binding Site. J. Virol., 70:4466-4473.
Vila-Coro, et al. (2000). HIV-1 Infection Through the CCR5 Receptor Is Blocked by Receptor Dimerization. Proc. Natl. Acad. Sci., 97(7):3388-3393.
Vita, C., et al. (1999). Rational Engineering of a Mini-Protein That Reproduces the Core of the CD4 Site Interacting With HIV-1 Envelope Glycoprotein. Proc. Natl. Acad. Sci., 96:13091-13096.
Wang et al. (1994). Deletion of T Lymphocytes in Human CD4 Transgenic Mice Induced by HIV-gp120 and gp120-Specific Antibodies From AIDS Patients. Eur. J. Immunol., 24:1553-1557.
Wells, T.N.C., et al. (1996). Selectivity and Antagonism of Chemokine Receptors. Journal of Leukocyte Biology, 59:53-60.
Wild, C., at al. (1992). A Synthetic Peptide Inhibitor of Human Immunodeficiency Virus Replication: Correlation Between Solution Structure and Viral Inhibition. Proc. Natl. Acad. Sci., 89:10537-10541.
Wild, C., et al. (1993). A synthetic peptide from HIV-1 Gp41 Is a Potent Inhibitor of Virus Mediated Cell-Cell Fusion. AIDS Res. Humn. Retroviruses, 9:1051-1053.
Wild, C., et al. (1994). Peptides Corresponding to a Predictive Alpha-Helical Domain of Human Immunodeficiency Virus Type 1 gp41 Are Potent Inhibitors of Virus Infection. Proc. Natl. Acad. Sci., 91:9770-9774.
Wild, C., et al. (1995). The Inhibitory Activity of an HIV Type 1 Peptide Correlates With Its Ability to Interact With a Leucine Zipper Structure. AIDS Res. Hum. Retroviruses, 11:323-325.
Wu et al. (1997). CCR5 Levels and Expression Pattern Correlate With Infectability by Macrophagetropic HIV-1 In Vitro. J. Exp. Med., 185(9):1681-1691.
Wu, et al. (1997). Interaction of Chemokine Receptor CCR5 With Its Ligands: Multiple Domains for HIV-1 gp120 Binding and a Single Domain for Chemokine Binding. J. Exper. Med., 186(8):1373-1381.
Wu, L., et al. (1996). CD4-Induced Interaction of Primary HIV-1 gp120 Glycoproteins With the Chemokine Receptor CCR-5. Nature, 384:179-183.
Yamagami, et al. (1994). cDNA Cloning and Functional Expression of Human Monocyte Chemoattractant Protein 1 Receptor. Biochem. Biophys. Res. Commun., 212:1156-1162.
Yarchoan, R. and Broder, S. (1992). Correlations Between the In Vitro and the In Vivo Activity of Anti-HIV Agents: Implications for Future Drug Development. J. Enzyme Inhibit., 6:99-11.
Ylisastigui, L., et al. (1998). Synthetic Full Length and Truncated RANTES Inhibit HIV-1 Infection or Primary Macrophages. AIDS, 12:977-984.
Zhang, Y.J., et al. (1994). Structure / Activity Analysis of Human Monocyte Chemoattractant Protein-1 (MCP-1) by Mutagenesis. J. Biol. Chem., 269:15918-15924.
PCT International Search Report issued Jun. 9, 1997 for International Application Publication No. WO 97/26009.
PCT International Search Report issued Jul. 5, 1997 for International Application Publication No. WO 98/56421.
PCT International Search Report issued Sep. 3, 1997 for International Application Publication No. WO 97/47319.
PCT International Search Report issued Sep. 12, 1998 for International Application Publication No. WO 98/56421.
PCT International Search Report issued Sep. 3, 1997 for International Application Publication No. WO 97/47318.
PCT International Search Report issued Jun. 7, 2000 for International Application Publication No. WO 00/35409.
PCT International Search Report issued Aug. 13, 2003 for International Application Publication No. WO 03/072766.
PCT International Search Report issued Apr. 23, 2002 for International Application Publication No. WO 02/22077.
PCT International Search Report issued Jul. 31, 2003 for International Application Publication No. WO 02/083172.
PCT International Preliminary Examination Report issued Jan. 27, 2000 for International Application Publication No. WO 98/56421.
PCT International Preliminary Examination Report issued Jul. 10, 1998 for International Application Publication No. WO 97/37005.
PCT International Preliminary Examination Report issued Oct. 16, 1999 for International Application Publication No. WO 97/47319
PCT International Preliminary Examination Report issued Sep. 28, 2005 for International Application Publication No. WO 03/072766.
PCT International Preliminary Examination Report issued Apr. 5, 2006 for International Application Publication No. WO 03/072766.
PCT International Preliminary Examination Report issued Feb. 15, 2001 for International Application Publication No. WO 00/35409.
PCT International Preliminary Examination Report issued Dec. 24, 2003 for International Application Publication No. WO 02/083172.
PCT Written Opinion issued May 25, 2005 in connection with International Application Publication No. WO 03/072766.
European Supplementary Partial Search Report issued Sep. 27, 2004 for European Application No.
European Supplementary Partial Search Report issued Feb. 19, 2003 for European Patent Application No. 98931261.6.

(56) References Cited

OTHER PUBLICATIONS

European Supplementary Partial Search Report issued Aug. 26, 2004 for European Patent Application No. 97930120.7.
European Supplementary Partial Search Report issued Nov. 8, 2004 for European Patent Application No. 97930120.7.
European Supplementary Search Report issued Apr. 21, 2006 for European Application No. 03713632.2.
European Supplementary Search Report issued Mar. 6, 2002 for European Patent Application No. 97917856.3.
European Supplementary Search Report issued Apr. 27, 2006 for European Patent Application No. 01970984.9.
European Patent Office Communication issued Nov. 11, 2004 in connection with European Patent Application No. 97930120.7.
Max, E. "Immunoglobulins: Molecular Genetics" in Fundamental Imunology, 6th edition. W.E. Paul, ed., Lippincott-Raven Publishers, Philadelphia, 2008 pp. 192-236.
Nelson et al. "Efficacy and Safety of Maraviroc plus Optimized Background Therapy in Viremic, ART-experienced Patients Infected with CCR5-tropic HIV-1 in Europe, Australia, and North America: 24-Week results," 14th Annual Conference on Retroviruses and Opportunistic Infections. Feb. 28, 2007. Abstract #104aLB.
Schroeder et al. (2008) "Immunoglobulins: Structure and Function," Lippincott Williams & Wilkins:Maryland, Fundamental Immunology, 6th Edition, Chapter 4, pp. 125-151.
Combadiere, C. et al. (1995) Additions and Corrections to "Cloning and functional expression of a human eosinophil CC chemokine receptor," J. Biol. Chem. 270(28) 16491-16494.
Jun. 18, 2008 Communication including Partial European Search Report in connection with European Patent Application No. 07 01 4859.8.
Sep. 19, 2008 Final Office Action issued in connection with U.S. Appl. No. 09/460,216.
Jul. 9, 2008 Office Action issued in connection with U.S. Appl. No. 11/258,963.
Jul. 1, 2008 Office Action issued in connection with U.S. Appl. No. 11/581,944.
Jan. 9, 2008 Final Office Action issued in connection with U.S. Appl. No. 11/258,963.
May 29, 2008 Office Action issued in connection with U.S. Appl. No. 11/259,540.
Nov. 19, 2007 Final Office Action issued in connection with U.S. Appl. No. 09/904,356.
Apr. 9, 2008 Office Action issued in connection with U.S. Appl. No. 11/451,707.
Nov. 2, 2007 Office Action issued in connection with U.S. Appl. No. 11/805,573.
Sep. 21, 2007 Notice of Allowability issued in connection with U.S. Appl. No. 11/544,346, now U.S. Patent No. 7,345,153.
Mar. 11, 2008 Office Action issued in connection with U.S. Appl. No. 09/888,938.
May 31, 2007 Office Action issued in connection with U.S. Appl. No. 09/888,938.
Oct. 4, 2007 Office Action issued in connection with U.S. Appl. No. 11/175,815.
Nov. 16, 2007 Office Action issued in connection with U.S. Appl. No. 09/460,216.
Sep. 12, 2007 Final Office Action issued in connection with U.S. Appl. No. 11/400,497.
Apr. 3, 2008 Office Action issued in connection with U.S. Appl. No. 11/520,556.
Jan. 9, 2008 Office Action issued in connection with U.S. Appl. No. 11/259,540.
May 22, 2008 Office Action issued in connection with U.S. Appl. No. 11/491,330.
Aug. 5, 2008 Final Office Action issued in connection with U.S. Appl. No. 11/175,815.
Aug. 19, 2008 Office Action issued in connection with U.S. Appl. No. 11/804,746.
Aug. 21, 2008 Office Action issued in connection with U.S. Appl. No. 09/904,356.
Sep. 11, 2008 Office Action issued in connection with U.S. Appl. No. 11/805,573.
Apr. 9, 2008 Office Action issued in connection with U.S. Appl. No. 11/316,078.
May 14, 2008 Office Action issued in connection with U.S. Appl. No. 11/400,497.
Notification of Transmittal of the International Search Report and the Written Opinion of the International Searching Authority, or the Declaration issued Jul. 25, 2008 in connection with PCT International Application No. PCT/US06/28565.
Notification of Transmittal of the International Search Report and the Written Opinion of the International Searching Authority, or the Declaration issued Aug. 15, 2008 in connection with PCT International Application No. PCT/US08/05564.
May 15, 2008 Office Action issued in connection with U.S. Appl. No. 11/581,945.
Sep. 16, 2008 Communication including a May 29, 2008 Extended European Search report in connection with European Patent Application No. 07014859.8.
Oct. 2, 2008 Communication Pursuant to Article 94(3) EPC and Result of Consultation issued in connection with European Patent Application No. 01970984.9.
Office Action issued Nov. 10, 2008 in connection with U.S. Appl. No. 11/400,497.
Office Action issued Dec. 12, 2008 in connection with U.S. Appl. No. 11/491,330.
Final Office Action issued Dec. 31, 2008 in connection with U.S. Appl. No. 11/581,945.
Final Office Action issued Jan. 9, 2009 in connection with U.S. Appl. No. 11/451,707.
Final Office Action issued Jan. 27, 2009 in connection with U.S. Appl. No. 11/520,556.
Final Office Action issued Jan. 27, 2009 in connection with U.S. Appl. No. 11/259,540.
Simmons, G. et al. (1996) "Primary, syncytium-inducing human immunodeficiency virus type 1 isolates are dual-tropic and most can use either Lestr or CCR5 as coreceptors for virus entry," J. Virol. 70(12):8355-8360.
Valentin, A. et al. (1994) "Dual tropism for macrophages and lymphocytes is a common feature of primary human immunodeficiency virus type 1 and 2 isolates," J. Virol. 68(10):6684-6689.
Final Office Action issued Feb. 4, 2009 in connection with U.S. Appl. No. 11/316,078.
Mar. 25, 2009 Office Action issued in connection with U.S. Appl. No. 11/175,815.
Extended European Search Report, including a European Search Report and a European Search Opinion, issued Apr. 17, 2009 in connection with European Patent Application No. 08168669.3.
May 1, 2009 Final Office Action issued in connection with U.S. Appl. No. 11/258,963.
Notification of Transmittal of the International Search Report and the Written Opinion of the International Searching Authority, or the Declaration, including an International Search Report and Written Opinion, issued May 8, 2009 in connection with PCT International Application No. PCT/US08/08752.
Prado, J. et al. (2002) "Amprenavir-resistant HIV-1 exhibits lopinavir cross-resistance and reduced replication capacity," AIDS, vol. 16, pp. 1009-1017.
Hanna, G. et al. (2000) "Patterns of Resistance Mutations Selected by Treatment of Human Immunodeficiency Virus Type 1 Infection with Zidovudine, Didanosine, and Nevirapine," vol. 181, pp. 904-911.
Greenberg, M. and Cammack, N. (2004) "Resistance to enfuvirtide, the first HIV fusion inhibitor," vol. 54, pp. 333-340.
May 13, 2009 Office Action issued in connection with U.S. Appl. No. 09/904,356.
Jun. 23, 2009 Final Office Action issued in connection with U.S. Appl. No. 11/805,573.
Jun. 26, 2009 Final Office Action issued in connection with U.S. Appl. No. 11/581,944.
Jun. 23, 2009 Final Office Action issued in connection with U.S. Appl. No. 09/460,216.
Jun. 26, 2009 Office Action issued in connection with U.S. Appl. No. 11/520,556.

(56) References Cited

OTHER PUBLICATIONS

Jul. 14, 2009 Final Office Action issued in connection with U.S. Appl. No. 11/804,746.
Aug. 7, 2009 Advisory Action issued in connection with U.S. Appl. No. 11/581,945.
Notification of Transmittal of the International Search Report and the Written Opinion of the International Searching Authority, or the Declaration issued Aug. 31, 2009, including an International Search Report and Written Opinion, in connection with PCT International Application No. PCT/US09/02654.
Lu et al. (2006) "Rapid emergence of enfuvirtide resistance in HIV-1 infected patients:results of a clonal analysis," J Acquir Defic. Syndr., vol. 43(1), pp. 60-64 (abstract).
Sep. 24, 2009 Office Action issued in connection with U.S. Appl. No. 11/807,349.
Sep. 21, 2009 Final Office Action issued in connection with U.S. Appl. No. 09/888,938.
Oct. 2, 2009 Office Action issued in connection with U.S. Appl. No. 11/894,677.
Bajetto A. et al. (2001) "Chemokines and Their Receptors in the Central Nervous System," Frontiers in Neuroendocrinology, 22, 147-184.
Oct. 5, 2009 Office Action issued in connection with U.S. Appl. No. 11/491,330.
Oct. 6, 2009 Office Action issued in connection with U.S. Appl. No. 11/451,707.
Moore, J.P. (1999) "HIV-1 neutralizing antibodies: How full is the bottle?" Nat. Med. 5(2):142-144.
Montefiori, D.C. (2005) "Neutralizing antibodies take a swipe at HIV in vivo," Nat. Med. 11(6):593-594.
Trkola, A. et al. (2005) "Delay of HIV-1 rebound after cessation of antiretroviral therapy through passive transfer of human neutralizing antibodies," Nat. Med. 11(6):615-622.
Bansal, G.P. (2007) A summary of the workshop on passive immunization using monoclonal antibodies for HIV/AIDS, held at the National Institute of Allergy and Infectious Diseases, Bethesda, Mar. 2006, Biol. 35:367-371.
Oct. 7, 2009 Office Action issued in connection with U.S. Appl. No. 11/316,078.
Keller, M.A. and Stiehm, E.R. (2000) "Passive immunity in prevention and treatment of infectious diseases," Clin. Microbiol Rev., 13(4):602-14.
Notification Concerning Transmittal of International Preliminary Report on Patentability, including an International Preliminary Report on Patentability dated Nov. 3, 2009 and a Written Opinion dated Aug. 15, 2008 in connection with PCT International Application No. PCT/US08/05564.
Dec. 10, 2009 Office Action issued in connection with U.S. Appl. No. 09/904,356.
Extended Supplementary European Search Report, including a European Search Report and a European Search Opinion, issued Mar. 3, 2010 in connection with European Patent Application No. 06788240.7.
Genentech "Herceptin/Trastuzumab", 2003, published at www.cancerconsultants.com/druginserts/trastuzumab.pdf.
Maeda et al., *J. Virol.* (2004) 78(16):8654-8662.
Olson et al., *Current Drug targets—Infectious Disorders*, 3(4):283-294.
Poli, G., *IDrugs*, 4(9):1068-1071 (2001).
Metas et al., *J. Virol.*, (2003), 77(4):2762-2767.
Alkhatib, G. et al., (1996) "CC CKR5: A RANTES, MIP-1α, MIP-1β Receptor As a Fusion Cofactor for Macrophage-Tropic HIV-1", *Science* 272:1955-1958.
Allaway, G.A. et al., (1993) "Synergistic Inhibition of HIV-1 Envelope-Mediated Cell Fusion by CD4-Based Molecules in Combination With Antibodies to Gp120 or Gp41", *AIDS Res Hum Retroviruses* 9:581-587.
Allaway, G.P. et al., (1995) "Expression and Characterization of CD4-IgG$_2$, A Novel Heterotetramer That Neutralizes Primary HIV Type 1 Isolates", *AIDS Res Hum Retrovirus* 11:533-539.

Baba, M. et al., (2005) "Tak-652, A Novel Small Molecule CCR5 Antagonist With Potent Anti-HIV-1 Activity", *12th Conference on Retroviruses and Opportunistic Infections*. Boston, MA, Feb. 22-25, 2005, Abstract 541.
Baba, M. et al., (1999) "A Small-Molecule, Nonpeptide CCR5 Antagonist With Highly Potent and Selective Anti-HIV-1 Activity", *Proc. Natl. Acad. Sci* 96:5698-5703.
Balotta, C. et al., (1997) "Homozygous Delta 32 Deletion of the CCR-5 Chemokine Receptor Gene in an HIV-1-Infected Patient", *AIDS* 11:F67-F71.
Basavapathruni, A. et al., (2004) "Defining a Molecular Mechanism of Synergy Between Nucleoside and Nonnucleoside AIDS Drugs", *J. Biol. Chem.* 279:6221-6224.
Berger, E.A., (1997) "HIV Entry and Tropism: The Chemokine Receptor Connection" *AIDS* 11(Suppl A):S3-S16.
Bieniasz P.D and B.R. Cullen, (1998) "Chemokine Receptors and Human Immunodeficiency Virus Infection", *Front. Biosci.* 3:d44-d58.
Biti, R., (1997) "HIV-1 Infection in an Individual Homozygous for the CCR5 Deletion Allele", *Nature Med.* 3:252-253.
Borkow, G. et al., (1999) "The Thiocarboxanilide Nonnucleoside Inhibitor UC781 Restores Antiviral Activity of 3'-Azido-3'-Deoxythymidine (AZT) Against AZT-Resistant Human Immunodeficiency Virus Type 1", *Antimicro. Agents Chemother.* 43:259-263.
Burkly, L. et al., (1992) "Inhibition of HIV Infection by a Novel CD4 Domain 2-Specific Monoclonal Antibody. Dissecting the Basis for Its Inhibitory Effect on HIV-Induced Cell Fusion", *J. Immunol.* 149:1779-1787.
Burkly, L. et al., (1995) "Synergistic Inhibition of Human Immunodeficiency Virus Type 1 Envelope Glycoprotein-Mediated Cell Fusion and Infection by an Antibody to CD4 Domain 2 in Combination With Anti-gp120 Antibodies", *J. Virol.* 69:4267-4273.
Choe, H. et al., (1996) "The Beta-Chemokine Receptors CCR3 and CCR5 Facilitate Infection by Primary HIV-1 Isolates", *Cell* 85:1135-1148.
Chou, T.C. and P. Talalay, (1984) "Quantitative Analysis of Dose-Effect Relationships: The Combined Effects of Multiple Drugs or Enzyme Inhibitors" *Adv. Enzyme Regulations* 22:57-55.
Cocchi, F., (1995) "Identification of RANTES, MIP-1α and MIP-1β as the Major HIV-Suppressive Factors Produced by CD8+ T-Cells", *Science* 270:1811-1815.
Combadiere, C. et al., (1996) "Cloning and Functional Expression of CC CKR5, A Human Monocyte CC Chemokine Receptor Selective for MIP-1α, MIP-1β, and RANTES", *J. Leukoc. Biol.* 60:147-152.
Connor, R.I et al., (1997) "Change in Co-Receptor Use Correlates With Disease Progression in HIV-1 Infected Individuals", *J. Exp. Med.* 185:621-628.
Cormier, E.G. and T. Dragic, (2002) "The Crown and Stem of the V3 Loop Play Distinct Roles in Human Immunodeficiency Virus Type 1 Envelope Glycoprotein Interactions With the CCR5 Coreceptor", *J. Virol.* 76:8953-8957.
Cudeck, R. and L.L. O'Dell, (1994) "Applications of Standard Error Estimates in Unrestricted Factor Analysis: Significance Tests for Factor Loadings and Correlations", *Psychol. Bull.* 115: 475-487.
Dalgleish, A.G. et al., (1984) "The CD4 (T4) Antigen Is an Essential Component of the Receptor for the AIDS Retrovirus", *Nature* 312:763-766.
Demarest, J. et al., (2004) "Single and Multiple Dose Escalation Study to Investigate the Safety, Pharmacokinetics, and Receptor Binding of GW873140, a Novel CCR5 Receptor Antagonist, in Healthy Subjects", *11th Conference on Retroviruses and Opportunistic Infections,* San Francisco, CA, Feb. 8-11, 2004, Abstract No. 139.
Deng H. et al., (1996) "Identification of a Major Co-Receptor for Primary Isolates of HIV-1", *Nature* 81:661-666.
Dorr, P. et al., (2003) "UK-427,857, A Novel Small Molecule HIV Entry Inhibitor is a Specific Antagonist of the Chemokine Receptor CCR5", *10th Conference on Retroviruses and Opportunistic Infections*, Boston, MA, Feb. 10-14, Paper #12.

(56) References Cited

OTHER PUBLICATIONS

Dorr, P. et al., (2005) "Maraviroc (UK-427,857), A Potent, Orally Bioavailable, and Selective Small-Molecule Inhibitor of Chemokine Receptor CCR5 With Broad-Spectrum Anti-Human Immunodeficiency Virus Type 1 Activity", *Antimicrob. Agents Chemother.* 49:4721-4732.

Dragic, T.V. et al., (1996) "HIV-1 Entry Into CD4+ Cells is Mediated by the Chemokine Receptor CC-CKR-5", *Nature* 381:667-673.

Dragic, T. et al., (1992) "Complementation of Murine Cells for Human Immunodeficiency Virus Envelope/CD4-Mediated Fusion in Human/Murine Heterokaryons", *J. Virol.* 66:4794-4802.

Dragic, T.V. et al., (2000) "A Binding Pocket for a Small Molecule Inhibitor of HIV-1 Entry Within the Transmembrane Helices of CCR5", *Proc. Natl. Acad. Sci.* 97:5639-5644.

Este, J.A., (2002) "Sch-351125 and Sch-350634. Schering-Plough", *Curr. Opin. Investig. Drugs* 3:379-383.

Fatkenheuer, G. et al., (2005) "Efficacy of Short-Term Monotherapy With Maraviroc, A New CCR5 Antagonist, in Patients Infected With HIV-1", *Nat. Med.* 11:1170-1172.

Feng, Y. at al., (1996) "HIV-1 Entry Cofactor: Functional cDNA Cloning of a Seven-Transmembrane, G Protein-Coupled Receptor", *Science* 272:872-877.

Finke, P.E. et al., (2001) "Antagonists of the Human CCR5 Receptor As Anti-HIV-1 Agents. Part 4: Synthesis and Structure-Activity Relationships for 1-[N-(Methyl)-N-(Phenylsulfonyl)Amino]-2-(Phenyl)-4-(4-(N-(Alkyl)-N-(Benzyloxycarbonyl)Amino)Piperidin-1-Y1)Butanes", *Bioorg. Med. Chem. Lett.* 11:2475-2479.

Garzino-Demo, A. et al., (1999) "Spontaneous and Antigen-Induced Production of HIV-Inhibitory Beta-Chemokines are Associated With AIDS-Free Status", *Proc. Natl. Acad. Sci.* 96:11986-11991.

Hale, J.J. et al., (2001) "1,3,4-Trisubstituted Pyrrolidine CCR5 Receptor Antagonists. Part 2: Lead Optimization Affording Selective, Orally Bioavailable Compounds With Potent Anti-HIV Activity", *Bioorg. Med. Chem. Lett.* 11:2741-2745.

Hale, J.J. et al., (2002) "1,3,4-Trisubstituted Pyrrolidine CCR5 Receptor Antagonists. Part 3: Polar Functionality and Its Effect on Anti-HIV-1 Activity", *Bioorg. Med. Chem. Lett.* 12:2997-3000.

Hedge, V.R. et al., (2004) "Three New Compounds From the Plant *Lippia alva* as Inhibitors of Chemokine Receptor 5 (CCR5)", *Bioorg. Med. Chem. Lett.* 12:5339-5342.

HGS Press Release (2004) "Human Genome Sciences Characterizes Panel of Novel Human Monoclonal Antibodies That Specifically Antagonize the CCR5 Receptor and Block HIV-1 Entry", Nov. 2, 2004.

HGS Press Release (2005) "Huamn Genome Sciences Begins Dosing of Patients in a Phase 1 Clinical Trial of CCR5 mAb in Patients Infected With HIV-1", Mar. 30, 2005.

Huang, Y. et al., (1996) "The Role of a Mutant CCR5 Allele in HIV-1 Transmission and Disease Progression", *Nat. Med.* 2:1240-1243.

Huffnagle, G.B. et al., (1999) "Cutting Edge: Role of C—C Chemokine Receptor 5 in Organ-Specific and Innate Immunity to *Cryptococcus neoformans*", *J. Immunol.* 163:4642-4646.

Iizawa, Y. et al., (2003) "Anti-HIV-1 Activity of TAK-220, a Small Molecule CCR5 Antagonist", *10th Conference on Retroviruses and Opportunistic Infections.* Boston, MA, Feb. 10-14, 2003.

Imamura, S. et al., (2004) "CCR5 Antagonists as Anti-HIV-1 Agents. Part 2: Synthesis and Biological Evaluation of N-[3-(4-Benzylpiperidin-1-Y1)Propyl]-N,N'-Diphenylureas", *Bioorg. Med. Chem.* 12:2295-2306.

Imamura, S. et al., (2004) "CCR5 Antagonists as Anti-HIV-1 Agents. 1. Synthesis and Biological Evaluation of 5-Oxopyrrolidine-3-Carboxamide Derivatives", *Chem. Pharm. Bull* (Tokoyo) 52:63-73.

Imamura, S. et al., (2005) "CCR5 Antagonists as Anti-HIV-1 Agents. Part 3: Synthesis and Biological Evaluation of Piperidine-4-Carboxamide Derivatives", *Bioorg. Med. Chem.* 13:397-416.

Jayasuriya, H. et al., (2004) "Isolation and Structure of Antagonists of Chemokine Receptor (CCR5)", *J. Nat. Prod.* 67:1036-1038.

Johnson, V.A. et al., (1991) "Two-Drug Combinations of Zidovudine, Didanosine, and Recombinant Interferon-Alpha A Inhibit Replication of Zidovudine-Resistant Human Immunodeficiency Virus Type 1 Synergistically In Vitro", *J. Infect. Diseases* 164:646-655.

Kawamura, T. et al., (2003) "Candidate Microbicides Block HIV-1 Infection of Human Immature Langerhans Cells Within Epithelial Tissue Explants", *J. Exp. Med.* 192:1491-1500.

Kuhmann, S.E. et al., (2004) "Genetic and Phenotypic Analyses of Human Immunodeficiency Virus Type 1 Escape From a Small-Molecule CCR5 Inhibitor", *J. Virol.* 78:2790-2807.

Ketas, T.J. et al., (2003) "Human Immunodeficiency Virus Type 1 Attachment, Coreceptor, and Fusion Inhibitors Are Active Against Both Direct and trans Infection of Primary Cells", *J. Virol.* 77:2762-2767.

Kim, D. et al., (2001) "Discovery of Human CCR5 Antagonists Containing Hydantoins for the Treatment of HIV-1 Infection", *Bioorg. Med. Chem. Lett.* 11:3099-3102.

Kim, D. et al., (2001) "Design, Synthesis, and SAR of Heterocycle-Containing Antagonists of the Human CCR5 Receptor for the Treatment of HIV-1 Infection", *Bioorg. Med. Chem. Lett.* 11:3103-3106.

Kim, D. et al., (2005) "Potent 1,3,4-Trisubstituted Pyrrolidine CCR5 Receptor Antagonists: Effects of Fused Heterocycles on Antiviral Activity and Pharmacokinetic Properties", *Bioorg. Med. Chem. Lett.* 15:2129-2134.

Klatzmann, D. et al., (1984) "T-lymphocyte T4 molecule behaves as the receptor for human retrovirus LAV", *Nature* 312:767-768.

Koyanagi, Y., et al., (1987) "Dual Infection of the Central Nervous System by AIDS Viruses With Distinct Cellular Tropisms", *Science* 236:819-822.

Kumar, S. et al., (2003) "Pharmacokinetics and Interactions of a Novel Antagonist of Chemokine Receptor 5 (CCR5) With Ritonavir in Rats and Monkeys: Role of CYP3A and P-Glycoprotein", *J. Pharmacol. Exp. Ther.* 304:1161-1171.

Laal, S. et al., (1994) "Synergistic Neutralization of Human Immunodeficiency Virus Type 1 by Combinations of Human Monoclonal Antibodies", *J. Virol* 68:4001-4008.

Lalezari, J.P. et al., (2003) "Enfuvirtide, an HIV-1 Fusion Inhibitor, for Drug-Resistant HIV Infection in North and South America", *New Engl. J. of Med.* 348:2175-2185.

Lalezari, J. et al., (2002) "Enfuvirtide (T-20) in Combination With an Optimized Background (OB) Regimen v. OB Alone: Week 24 Response . . . HIV Antiretroviral (ARV) Resistance", 42nd Annual Interscience Conference on Antimicrobial Agents and Chemotherapy, Abstract H-1074-2002.

Lalezari, J. et al., (2003) "Final Analysis of T1249-102: T-1249 Retains Potent Short Term Antiviral Activity in Patients Who Have Failed a Regimen Containing Enfuvirtide (ENF)", 43rd Annual Interscience Conference on Antimicrobial Agents and Chemotherapy, Abstract H-444-2003.

Lalezari, J. et al., (2004) "Long Term Safety of T-1249, A Potent Inhibitor of HIV Fusion", 44th Annual Interscience Conference on Antimicrobial Agents and Chemotherapy, Abstract H-210-2004.

Lalezari, J. et al., (2004) "873140, A Novel CCR5 Antagonist: Antiviral Activity and Safety During Short-Term Monotherapy in HIV-Infected Adults", 44th Annual Interscience Conference on Antimicrobial Agents and Chemotherapy, Abstract H-1137b-2004.

Lalezari, J. et al., (2005) "Antiviral Activity and Safety of 873140, a Novel CCR5 Antagonist, During Short-Term Monotherapy in HIV-Infected Adults", *AIDS* 19:1443-1448.

Lapidot, T. et al., (2001) "Mechanism of Human Stem Cell Migration and Repopulation of NOD/SCID and B2mnull NOD/SCID Mice. The Role of SDF-1/CXCR4 Interactions", *Ann. N.Y. Acad. Sci.* 938:83-95.

Lazzarin, A. et al., (2003) "Efficacy of Enfuvirtide in Patients Infected With Drug-Resistant HIV-1 in Europe and Australia", *New Engl. J. Med.* 348:2186-2195.

Lee, B. et al., (1999) "Epitope Mapping of CCR5 Reveals Multiple Conformational States and Distinct But Overlapping Structures Involved in Chemokine Coreceptor Function", *J. Biol. Chem.* 274:9617-9626.

Li, A. et al., (1997) "Synergistic Neutralization of a Chimeric SIV/HIV Type 1 Virus With Combinations of Human Anti-HIV Type 1 Envelope Monoclonal Antibodies or Hyperimmune Globulins", *AIDS Res. Hum. Retroviruses* 13:647-56.

(56) References Cited

OTHER PUBLICATIONS

Li, A.H. et al., (1998) "Synergistic Neutralization of Simian-Human Immunodeficiency Virus SHIV-Vpu+ by Triple and Quadruple Combination of Human Monoclonal Antibodies and High-Titer Antihuman Immunodeficiency Virus Type 1 Immunoglobulins", *J. Virol.* 72:3235-3240.

Lin, P.F. et al., (2003) "A Small Molecule HIV-1 Inhibitor That Targets the HIV-1 Envelope and Inhibits CD4 Receptor Binding", *Proc. Nat. Acad. Sci.* 100:11013-11018.

Lin, P.F. et al., (2002) "Identification and Characterization of a Novel Inhibitor of HIV-1 Entry: Virology and Resistance", *9th Conference on Retroviruses and Opportunistic Infections.* Seattle, WA Feb. 24-28, 2002.

Littman, D.R., (1998) "Chemokine Receptors: Keys to AIDS Pathogenesis?", *Cell* 93:677-680.

Litwin, V. et al., (1996) "Human Immunodeficiency Virus Type 1 Membrane Fusion Mediated by a Laboratory-Adapted Strain and a Primary Isolate Analyzed by Resonance Energy Transfer", *J. Virol.* 70:6437-6441.

Liu, R. et al., (1996) "Homozygous Defect in HIV-1 Coreceptor Accounts for Resistance of Some Multiply-Exposed Individuals to HIV-1 Infection", *Cell* 86:367-377.

Liu, H. et al., (1999) "Polymorphism in RANTES Chemokine Promoter Affects HIV-1 Disease Progression", *Proc. Natl. Acad. Sci.* 96:4581-4585.

Lynch, C.L. et al., (2003) "1,3,4-Trisubstituted Pyrrolidine CCR5 Receptor Antagonists. Part 4: Synthesis of N-1 Acidic Functionality Affording Analogues With Enhanced Antiviral Activity Against HIV", *Bioorg. Med. Chem. Lett.* 12:3001-3004.

Lynch, C.L. et al., (2002) "CCR5 Antagonists: Bicyclic Isoxazolidines As Conformationally Constrained N-1-Substituted Pyrrolidines", *Bioorg. Med. Chem. Lett.* 12:677-679.

Lynch, C.L. at al., (2003) "1,3,4-Trisubstituted Pyrrolidine CCR5 Receptor Antagonists: Modifications of the Arylpropylpiperidine Side Chains", *Bioorg. Med. Chem. Lett.* 13:119-123.

Lynch, C.L. et al., (2003) "CCR5 Antagonists: 3-(Pyrrolidin-1-Yl)Propionic Acid Analogues With Potent Anti-HIV Activity", *Org. Lett.* 5:2473-2475.

Maddon, P.J. et al., (1986) "The T4 Gene Encodes the AIDS Virus Receptor and Is Expressed in the Immune System and the Brain", *Cell* 47:333-348.

Maeda, K. et al., (2004) "Spirodiketopiperazine-Based CCR5 Inhibitor Which Preserves CC-Chemokine/CCR5 Interactions and Exerts Potent Activity Against R5 Human Immunodeficiency Virus Type 1 In Vitro", *J. Virol.* 78:8654-8662.

Maeda, K. et al., (2001) "Novel Low Molecular Weight Spirodiketopiperazine Derivatives Potently Inhibit R5 HIV-1 Infection Through Their Antagonistic Effects on CCR5", *J. Biol. Chem.* 276:35194-35200.

Marozsan, A.J. et al., (2005) "Generation and Properties of a Human Immunodeficiency Virus Type 1 Isolate Resistant to the Small Molecule CCR5 Inhibitor, SCH-417690 (SCH-D)", *Virology* 338:182-199.

McCombie, S.W. et al., (2003) "Piperazine-Based CCR5 Antagonists as HIV-1 Inhibitors. III: Synthesis, Antiviral and Pharmacokinetic Profiles of Symmetrical Heteroaryl Carboxamides", *Bioorg. Med. Chem. Lett.* 13:567-571.

McDougal, J.S. et al., (1986) "Binding of HTLV-III/LAV to T4+ T Cells by a Complex of the 110K Viral Protein and the T4 Molecule", *Science* 231:382-385.

Merluzzi, V.J. et al., (1990) "Inhibition of HIV-1 Replication by a Nonnucleoside Reverse Transcriptase Inhibitor", *Science* 250:1411-1413.

Michael, N.L et al., (1997) "The Role of Viral Phenotype and CCR-5 Gene Defects in HIV-1 Transmission and Disease Progression", *Nat. Med.* 3:338-340.

Molla, A. et al., (2002) "In Vitro Antiviral Interaction of Lopinavir With Other Protease Inhibitors", *Antimicrob. Agents Chemother.* 46:2249-2253.

Moore, J.P. et al., (1992) "A Monoclonal Antibody to CD4 Domain 2 Blocks Soluble CD4-Induced Conformational Changes in the Envelope Glycoproteins of Human Immunodeficiency Virus Type 1 (HIV-1) and HIV-1 Infection of CD4+ Cells", *J. Virol.* 66:4784-4793.

Nagashima, K.A. et al., (2001) "Human Immunodeficiency Virus Type 1 Entry Inhibitors PrRO 542 and T-20 Are Potently Synergistic in Blocking Virus-Cell and Cell-Cell Fusion", *J. Infect. Dis.* 183:1121-1125.

Nakata, H. at al., (2005) "Potent Anti-R5 Human Immunodeficiency Virus Type 1 Effects of a CCR5 Antagonist, AK602/ON04128/GW873140, in a Novel Human Peripheral Blood Mononuclear Cell Nonobese Diabetic-SCID, Interleukin-2 Receptor Gamma-Chain-Knocked-Out AIDS Mouse Model", *J. Virol.* 79:2087-2096.

Nishikawa, M. et al., (2005) "Analysis of Binding Sites for the New Small-Molecule CCR5 Antagonist TAK-220 on Human CCR5", *Antimicrob. Agents Chemother.* 49:4708-4715.

O'Brien, T.R. et al., (1997) "HIV-1 Infection in a Man Homozygous for CCR5 Delta 32", *Lancet* 349:1219.

Olson, W.C. et al., (1999) "Differential Inhibition of Human Immunodeficiency Virus Type 1 Fusion, gp 120 Binding and CC-Chemokine Activity of Monoclonal Antibodies to CCR5", *J. Virol.* 73:4145-4155.

Palani, A. et al., (2002) "Synthesis, SAR, and Biological Evaluation of Oximino-Piperidino-Piperidine Amides. 1. Orally Bioavailable CCR5 Receptor Antagonists With Potent Anti-HIV Activity", *J. Med. Chem.* 45:3143-3160.

Palani, A. et al., (2001) "Discovery of 4-[(Z)-(4-Bromophenyl)-(Ethoxyimino)Methyl]-1'-[(2,4-Dimethyl-3-Pyridinyl)Carbonyl]-4'-Methyl-1,4'-Bipiperidine N-Oxide (SCH 351125): An Orally Bioavailable Human CCR5 Antagonist for the Treatment of HIV Infection", *J. Med. Chem.* 44:3339-3342.

Palani, A. et al., (2003) "Biological Evaluation and Interconversion Studies of Rotamers of SCH 351125, An Orally Bioavailable CCR5 Antagonist", *Bioorg. Med. Chem. Lett.* 13:705-708.

Palani, A. et al., (2003) "Oximino-Piperidino-Piperidine-Based CCR5 Antagonists. Part 2: Synthesis, SAR and Biological Evaluation of Symmetrical Heteroaryl Carboxamides", *Bioorg. Med. Chem. Lett.* 13:709-712.

Palella, F.L et al., (1998) "Declining Morbidity and Mortality Among Patients With Advanced Human Immunodeficiency Virus Infection", *New Engl. J. Med.* 338:853-860.

Raport, C.J. et al., (1996) "New Members of the Chemokine Receptor Gene Family", *J. Leukoc. Biol.* 59:18-23.

Ray, N. and R.W. Doms, (2006) "HIV-1 Coreceptors and Their Inhibitors", *Curr. Top. Microbiol. Immunol.* 303:97-120.

Reyes, G., (2001) "Development of CCR5 Antagonists as a New Class of Anti-HIV Therapeutic", *8th Conference on Retroviruses and Opportunistic Infections.* Chicago, IL, Feb. 5, 2001.

Reynes, J. et al., (2002) "SCH C: Safety and Antiviral Effects of a CCR5 Receptor Antagonist in HIV-1 Infected Subjects", *9th Conference on Retroviruses and Opportunistic Infections.* Seattle, WA, Feb. 25, 2002.

Robinson, B.S. et al, (2000) "BMS-232632, A Highly Potent Human Immunodeficiency Virus Protease Inhibitor That Can Be Used in Combination With Other Available Antiretroviral Agents", *Antimicrob. Agents Chemother.* 44:2093-2099.

Roschke, V. et al., (2004) "Characterization of a Panel of Novel Human Monoclonal Antibodies That Specifically Antagonize CCR5 and Block HIV Entry", *44th Annual Interscience Conference on Antimicrobial Agents and Chemotherapy,* Washington, D.C., Oct. 30-Nov. 2, 2004.

Samson, M. et al., (1997) "The Second Extracellular Loop of CCR5 Is the Major Determinant of Ligand Specificity", *J. Biol. Chem.* 272:24934-24941.

Schecter, A.D. et al., (2000) "Human Vascular Smooth Muscle Cells Possess Functional CCR5", *J. Biol. Chem.* 275:5466-5471.

Schols, D. et al., (1997) "Inhibition of T-Tropic HIV Strains by Selective Antagonization of the Chemokine Receptor CXCR4", *J. Exp. Med.* 186:1383-1398.

Schuh, J.M. et al., (2002) "The Role of CC Chemokine Receptor 5 (CCR5) and RANTES/CCL5 During Chronic Fungal Asthma in Mice", *FASEB* 16:228-230.

(56) References Cited

OTHER PUBLICATIONS

Schurmann, D. et al., (2004). "ACH D: Antiviral Activity of a CCR5 Receptor Antagonist", Abstract 140LB. *11th Conference on Retroviruses and Opportunistic Infections.* San Francisco, CA, Feb. 8-11, 2004.
Seibert, C. et al., (2006) "Interaction of Small Molecule Inhibitors of HIV-1 Entry With CCR5", *Virology* 349:41-54.
Seto, M. et al., (2005) "Orally Active CCR5 Antagonists as Anti-HIV-1 Agents. Part 3: Synthesis and Biological Activities of 1-Benzazepine Derivatives Containing a Sulfoxide Moiety", *Bioorg. Med. Chem. Lett.* 13:363-386.
Seto, M. et al., (2004) "Orally Active CCR5 Antagonists as Anti-HIV-1 Agents 2: Synthesis and Biological Activities of Anilide Derivatives Containing a Pyridine N-Oxide Moiety", *Chem. Pharm. Bull.* (Tokyo) 52:818-829.
Seto, M. et al., (2004) "Orally Active CCR5 . . . 1-Benzothiepine 1,1-Dioxide and 1-Benzazepine Derivatives Containing a Tertiary Amine Moiety", *Chem. Pharm. Bull.* (Tokyo) 52:577-590.
Shah, S.K. et al., (2005) "Synthesis and Evaluation of CCR5 Antagonists Containing Modified 4-Piperidinyl-2-Phenyl-1-(Phenylsulfonylamino)-Butane", *Bioorg. Med. Chem. Lett.* 15:977-982.
Shankaran, K. et al., (2004) "Syntheses and Biological Evaluation as 5-(Piperidin-1-yl)-3-Phenyl-Pentylsulfones as CCR5 Antagonists", *Bioorg. Med. Chem. Lett.* 14:3589-3593.
Shankaran, K. et al., (2004) "Syntheses and SAR Studies of 4-(Heteroarylpiperdin-1-Yl-Methyl)-Pyrrolidin-1-Yl-Acetic Acid Antagonists of the Human CCR5 Chemokine Receptor", *Bioorg. Med. Chem. Lett.* 14:3419-3424.
Shen, D.M. et al., (2004) "Antagonists of Human CCR5 Receptor Containing 4-(Pyrazolyl)Piperidine Side Chains. Part 1: Discovery and SAR Study of 4-Pyrazolylpiperidine Side Chains", *Bioorg. Med. Chem. Lett.* 14:935-939.
Shen, D.M. et al., (2004) "Antagonists of Human CCR5 Receptor Containing 4-(Pyrazolyl)Piperidine Side Chains. Part 2: Discovery of Potent, Selective, and Orally Bioavailable Compounds", *Bioorg. Med. Chem. Lett.* 14:941-945.
Shiraishi, M. et al., (2000) "Discovery of Novel, Potent, and Selective Small-Molecule CCR5 Antagonists as Anti-HIV-1 Agents: Synthesis and Biological Evaluation of Anilide Derivatives With a Quaternary Ammonium Moiety", *J. Med. Chem.* 43:2049-2063.
Shu, M. et al., (2004) "Antagonists of Human CCR5 Receptor Containing 4-(Pyrazolyl)Piperidine Side Chains. Part 3: SAR Studies on the Benzylpyrazole Segment", *Bioorg. Med. Chem. Lett.* 14:947-952.
Si, Z. et al., (2004) "Small-Molecule Inhibitors of HIV-1 Entry Block Receptor-Induced Conformational Changes in the Viral Envelope Glycoproteins", *Proc. Natl. Acad. Sci.* 101:5036-5041.
Simmons, G. et al., (1996) "Primary, Syncytium-Inducing Human Immunodeficiency Virus Type 1 Isolates are Dual-Tropic and Most Can Use Either Lestr or CCR5 As Coreceptors for Virus Entry", *J. Virol.* 70:8355-8360.
Spenlehauer, C. et al., (2001) "A Luciferase-Reporter Gene-Expressing T-Cell Line Facilitates Neutralization and Drug-Sensitivity Assays That Use Either R5 or X4 Strains of Human Immunodeficiency Virus Type 1", *J. Virol.* 280:292-300.
Strizki, J.M. et al., (2001) "SCH-C (SCH 351125), An Orally Bioavailable, Small Molecule Antagonist of the Chemokine Receptor CCR5, Is a Potent Inhibitor of HIV-1 Infection In Vitro and In Vivo", *Proc. Natl. Acad. Sci.* 98:12718-12723.
Tagat, J.R. et al., (2001) "Piperazine-Based CCR5 Antagonists as HIV-1 Inhibitors. II . . . Methyl-4-[3(S)-Methyl-4-[1(S)-[4-(Trifluoromethyl)Phenyl]Ethyl]-1-Piperazinyl]-Piperidine N1-Oxide (SCH-350634), An Orally Bioavailable, Potent CCR5 Antagonist", *J. Med. Chem.* 44:3343-3346.
Tagat, J.R. et al., (2001) "Piperazine-Based CCR5 Antagonists as HIV-1 Inhibitors. I: 2(S)-Methyl Piperazine as a Key Pharmacophore Element", *Bioorg. Med. Chem. Lett.* 11:2143-2146.
Tagat, J.R. et al., (2004) "Piperazine-Based CCR5 Antagonists as HIV-1 Inhibitors. IV. Discovery of 1-[(4,6-Dimethyl-5-Pyrimidinyl)Carbonyl]-4-[4-[2-Methoxy-1(R)-4-(Trifluoromethyl)Phenyl]Ethyl-3(S)-Methyl-1-Piperazinyl]-4-Methylpiperidine (Sch-417690/Sch-D), A Potent, Highly Selective, and Orally Bioavailable CCR5 Antagonist", *J. Med. Chem.* 47:2405-2408.
Takashima, K. et al., (2005) "Highly Potent Inhibition of Human, Immunodeficiency Virus Type 1 Replication by TAK-220, an Orally Bioavailable Small-Molecule CCR5 Antagonist", *Antimicrob. Agents Chemother.* 49:3474-3482.
Thali, M. et al., (1992) "Cooperativity of Neutralizing Antibodies Directed Against the VS and CD4 Binding Regions of the Human Immunodeficiency Virus gp120 Envelope Glycoprotein", *J. Acq. Immun. Defic. Synd.* 5:591-599.
Thoma, G. et al., (2004) "Orally Bioavailable Competitive CCR5 Antagonists", *J. Med. Chem.* 47:1939-1955.
Tilley, S. A., (1992) "Synergistic Neutralization of HIV-1 by Human Monoclonal Antibodies Against the V3 Loop and the CD4-Binding Site gp120", *AIDS Research and Human Retroviruses* 80:4:461-467.
Tran, E.H. et al., (2000) "Induction of Experimental Autoimmune Encephalomyelitis in C57BL/6 Mice Deficient in Either the Chemokine Macrophage Inflammatory Protein-1alpha or Its CCR5 Receptor", *Eur. J. Immunol.* 30:1410-1415.
Tremblay, C.L. et al., (1999) "Strong In Vitro Synergy Between the Fusion Inhibitor T-20 and the CXCR4 Blocker AMD-3100", *J. Acq. Immun. Defici. Synd.* 25(2)99-102.
Tremblay, C.Z. et al., (2002) "Anti-Human Immunodeficiency Virus Interactions of SCH-C (SCH 351125), A CCR5 Antagonist, With Other Antiretroviral Agents In Vitro", *Antimicrob. Agents Chemother.* 46:1336-1339.
Tremblay, C.L. et al., (2005) "TAK-652, a Novel Small Molecule Inhibitor of CCR5 Has Favorable Anti-HIV Interactions With Other Antiretorvirals In Vitro", *12th Conference on Retroviruses and Opportunistic Infections.* Boston, MA, Feb. 22-25, 2005, Abstract 542.
Tremblay, C.L. et al., (2005) "TAK-652, A Novel CCR5 Inhibitor, has Favourable Drug Interactions With Other Antiretrovirals In Vitro", *Antivir. Ther.* 10:967-968.
Tremblay, C.L. at al., (2005) "TAK-220, A Novel Small-Molecule CCR5 Antagonist, Has Favorable Anti-Human Immunodeficiency Virus Interactions With Other Antiretrovirals In Vitro", *Antimicrob. Agents Chemother.* 49:3483-3485.
Trkola, A. et al., (2001) "Potent, Broad-Spectrum Inhibition of Human Immunodeficiency Virus Type 1 by the CCR5 Monoclonal Antibody PRO 140", *J. Virol.* 75:579-588.
Trkola, A. et al., (1998) "Neutralization Sensitivity of Human Immunodeficiency Virus Type 1 Primary Isolates to Antibodies and CD4-based Reagents Is Independent of Coreceptor Usage", *J. Virol.* 72:1876-1885.
Trkola, A. et al., (1999) "A Cell Line-Based Neutralization Assay for Primary Human Immunodeficiency Virus Type 1 Isolates That Use Either the CCR5 or the CXCR4 Coreceptor", *J. Virol.* 72:8966-8974.
Tsamis, F. et al., (2003) "Analysis of the Mechanism by Which the Small-Molecule CCR5 Antagonists SCH-351125 and SCH-350581 Inhibit Human Immunodeficiency Virus Type 1 Entry", *J. Virol.* 77:5201-5208.
Vijh-Warrier, S., (1996) "Synergistic Neutralization of Human Immunodeficiency Virus Type 1 by a Chimpanzee Monoclonal Antibody Against the V2 Domain of gp120 in Combination With Monoclonal Antibodies Against the V3 Loop and the CD4-Binding Site", *J. Virol.* 70:4466-4473.
Watson, C. et al., (2005) "The CCR5 Receptor-Based Mechanism of Action of 873140, A Potent Allosteric Noncompetitive HIV Entry Inhibitor", *Mol. Pharmacal.* 67:1268-1282.
Wild, C. et al., (1992) "A Synthetic Peptide Inhibitor of Human Immunodeficiency Virus Replication: Correlation Between Solution Structure and Viral Inhibition", *Proc. Natl. Acad. Sci.* 89:10537-10541.
Willoughby, C.A. et al., (2001) "Combinatorial Synthesis of CCR5 Antagonists", *Bioorg. Med. Chem. Lett.* 11:3137-3141.
Willoughby, C.A. et al., (2003) "1,3,4 Trisubstituted Pyrrolidine CCR5 Receptor Antagonists Bearing 4-Aminoheterocycle Substituted Piperidine Side Chains", *Bioorg. Med. Chem. Lett.* 13:427-431.

(56) References Cited

OTHER PUBLICATIONS

Wu, L. et al., (1997) "Interaction of Chemokine Receptor CCR5 With its Ligands: Multiple Domains for HIV-1 gp120 Binding and a Single Domain for Chemokine Binding", *J. Exp. Med.* 186(8):1373-1381.

Zhou, Y. et al., (1998) "Impaired Macrophage Function and Enhanced T Cell-Dependent Immune Response in Mice Lacking CCR5, The Mouse Homologue of the Major HIV-1 Coreceptor", *J. Immunol.* 160:4018-4025.

Zhu, P. et al., (2001) "Structural Flexibility and Functional Valence of CD4-Igg2 (PRO 542): Potential for Cross-Linking Human Immunodeficiency Virus Type 1 Envelope Spikes", *J. Virol.* 75:6682-6686.

Dec. 12, 2008 Office Action issued in connection with U.S. Appl. No. 11/491,330.

Jun. 2, 2010 Office Action issued in connection with U.S. Appl. No. 11/491,330.

Communication Pursuant to Article 94(3) EPC issued in connection with EP 06788240.7.

Moore et al., "Co-receptors for HIV-1 entry." Current Opinion in Immunology, vol. 9: 551-562, 1997.

\* cited by examiner

Figure 1. Structures of lead compounds (A, B) and design of anilide derivatives 1 with quarternary ammonium moiety.

Scheme 1[a]

[a] (a) (1) (COCl)$_2$, cat. DMF/CH$_2$Cl$_2$, (2) 5, NEt$_3$/THF or 5, HOBt, WSC, NEt$_3$/DMF; (b) MeI/DMF; (c) ion-exchange resin (Cl$^-$)/aq MeOH.

Scheme 2[a]

[a] (a) (1) (COCl)$_2$, cat. DMF/CH$_2$Cl$_2$, (2) 7, NEt$_3$/THF ; (b) HCl/acetone; (c) SOCl$_2$, pyridine/CHCl$_3$; (d) NR$^2$R$^3$R$^4$/DMF.

PRO140-1101 CCR5 Lymphocyte Coating
*5 mg/kg cohort*

METHODS FOR INHIBITING HIV-1 REPLICATION INVOLVING THE ADMINISTRATION OF AN ANTI-CCR5 RECEPTOR MONOCLONAL ANTIBODY AND SMALL MOLECULE CCR5 RECEPTOR ANTAGONIST

This application is a divisional of U.S. Ser. No. 11/491,330, filed Jul. 21, 2006, which claims benefit of U.S. Provisional Application No. 60/702,064, filed Jul. 22, 2005; U.S. Provisional Application No. 60/701,889, filed Jul. 23, 2005; U.S. Provisional Application No. 60/711,528, filed Aug. 26, 2005; and U.S. Provisional Application No. 60/715,619, filed Sep. 9, 2005; the contents of each of which in its entirety is hereby incorporated by reference into this application.

Throughout this application, various publications are referenced in parentheses by author name and date, or by a patent or patent publication number. Full citations for these publications may be found at the end of the specification immediately preceding the claims. The disclosures of each of these publications in its entirety are hereby incorporated by reference into this application in order to more fully describe the state of the art as known to those skilled therein as of the date of this application.

This invention was made with support under United States Government Grant Nos. AI046871 and AI066329 from the National Institute of Allergy and Infectious Diseases. Accordingly, the United States Government has certain rights in the subject invention.

BACKGROUND OF THE INVENTION

Infection of cells by human immunodeficiency virus type 1 (HIV-1) is mediated by the viral envelope (Env) glycoproteins gp120 and gp41, which are expressed as a noncovalent, oligomeric complex on the surface of virus and virally infected cells. Entry of the virus into target cells proceeds through a cascade of events at the cell surface that include (1) binding of the viral surface glycoprotein gp120 to a cell surface receptor, (2) Env binding to fusion coreceptors, and (3) multiple conformational changes in gp41.

The first high-affinity interaction between the virion and the cell surface is the binding of gp120 to cell surface CD4, which is the primary receptor for HIV-1 (Dalgleish et al.; 1984; Klatzmann et al., 1984; Maddon et al., 1986; McDougal et al., 1986). This binding induces conformational changes in gp120, which enable it to interact with one of several chemokine receptors (Berger, 1997; Bieniasz et al., 1998; Dragic et al., 1997; Littman, 1998). The CC-chemokine receptor 5 (CCR5) is the major co-receptor for macrophage-tropic (R5) strains, and plays a crucial role in the transmission of HIV-1 (Berger, 1997; Bieniasz et al., 1998; Dragic et al., 1997; Littman, 1998). T cell line-tropic (X4) viruses use CXCR4 to enter target cells, and usually, but not always, emerge late in disease progression or as a consequence of virus propagation in tissue culture. Some primary HIV-1 isolates are dual-tropic (R5X4) since they can use both co-receptors, though not always with the same efficiency (Connor et al., 1997; Simmons et al., 1996). Binding of gp120 to a chemokine receptor in turn triggers conformational changes in the viral transmembrane glycoprotein gp41, which mediates fusion of the viral and cellular membranes.

Each stage of this multi-step process can be blocked with inhibitors of the appropriate viral or cellular protein, and the inhibitors of gp120, gp41, CD4 and coreceptor are collectively known as entry inhibitors. Entry inhibitors represent at least 4 distinct classes of agents based on their molecular targets and determinants of viral resistance (Olson and Maddon, 2003). Table 1 lists HIV-1 entry inhibitors known to be in clinical development or approved for clinical use.

PRO 542 is a tetravalent, third-generation CD4-IgG2 fusion protein comprising the D1D2 domains of CD4 genetically fused to the heavy and light chain constant regions of human IgG2 (Allaway et al., 1995; Zhu et al., 2001). This agent binds the HIV-1 envelope glycoprotein gp120 with nanomolar affinity and may inhibit virus attachment both by receptor blockade and by detaching gp120 from the virion surface, thereby irreversibly inactivating the virus.

TABLE 1

HIV-1 entry inhibitors

| Compound | Molecular Class | Target | Stage of Entry | Developer |
| --- | --- | --- | --- | --- |
| PRO542 | CD4-Ig Fusion Protein | gp120 | Attachment | Progenics |
| BMS-488043 | Small Molecule | gp120 | Attachment | Bristol-Myers Squibb |
| TNX-355 | Humanized antibody | CD4 | Post-Attachment | Tanox |
| PRO 140 | Humanized antibody | CCR5 | Coreceptor | Progenics |
| CCR5mAb004 | Human antibody | CCR5 | Coreceptor | Human Genome Sciences |
| SCH-D (vicriviroc) | Small Molecule | CCR5 | Coreceptor | Schering-Plough |
| UK-427,857 (maraviroc) | Small Molecule | CCR5 | Coreceptor | Pfizer |
| GW873140 | Small Molecule | CCR5 | Coreceptor | GlaxoSmithKline |
| TAK-652 | Small Molecule | CCR5 | Coreceptor | Takeda |
| AMD070 | Small Molecule | CXCR4 | Coreceptor | AnorMed |
| T-20 (enfuvirtide) | Peptide | gp41 | gp41 Fusion | Trimeris/Roche |

BMS-488043 is an optimized analog of BMS-378806 (see PCT International Publication Nos. WO 01/62255 A1 and WO 03/082289 A1), which has been variously reported to block gp120 attachment to CD4 (Lin et al., 2002; 2003) and post-attachment events (Si et al., 2004).
TNX-355 is a humanized IgG4 version of the anti-CD4 monoclonal antibody (mAb) 5A8, which blocks fusion events that occur post-attachment of gp120 to CD4 (Burkly et al., 1992; Moore et al., 1992).
PRO 140, a humanized anti-CCR5 mAb, and the small-molecule CCR5 antagonists, SCH-D (also now designated SCH 417670 or vicriviroc), UK-427,857 (also designated maraviroc) and GW873140, are discussed below.
CCR5mAb004 is a fully human mAb, generated using the Abgenix XenoMouse ® technology, that specifically recognizes and binds to CCR5 (Roschke et al., 2004). CCR5mAb004 has been reported to inhibit CCR5-dependent entry of HIV-1 viruses into human cells, and recently entered Phase 1 clinical trials (HGS Press Release, 2005).

TABLE 1-continued

HIV-1 entry inhibitors

| Compound | Molecular Class | Target | Stage of Entry | Developer |
| --- | --- | --- | --- | --- |

The first small-molecule anti-CCR5 antagonist identified as capable of inhibiting HIV-I infection was TAK-779 (Baba et al., 1999). However, TAK-779 exhibited poor oral bioavailability (Baba et al., 2005) and local injection site irritation (Iizawa et al., 2003), and has been replaced in clinical development by a TAK-779 derivative, TAK-652 (Baba et al., 2005). TAK-652 is an orally bioavailable CCR5 antagonist with potent anti-HIV-1 activity in the nanomolar range in vitro and promising pharmacological profiles in vivo (Baba et al., 2005).
AMD070 is a second-generation CXCR4 inhibitor; the first-generation CXCR4 inhibitor AMD3100 did not demonstrate a favorable safety window for HIV-1 therapy (Schols et al., 2002).
Finally, T-20 was approved for salvage therapy of HIV-1 infection following favorable antiviral and safety profiles in each of two pivotal Phase 3 studies (Lalezari et al., 2003; Lazzarin et al., 2003).

CCR5 as a Target for Anti-HIV-1 Therapy

As first demonstrated in 1986, HIV-1 binds to target cells via the CD4 receptor but requires additional host cell factors to mediate entry (Maddon et al., 1986). Over the next decade, a number of candidate coreceptors were proposed, but none reproducibly mediated viral entry when coexpressed with CD4 in otherwise nonpermissive cells. However, in 1996, certain chemokine receptors, mainly CCR5 and CXCR4, were shown to serve as requisite fusion coreceptors for HIV-1.

Cocchi et al. (1995) provided the first link between HIV-1 and chemokines, which are small (~8 kDa) homologous soluble proteins. Chemokines mediate the recruitment and activation of immune cells. They are classified as CC-, CXC-, $CX_3C$- and XC-chemokines based on the number and sequential relationship of the first two of four conserved cysteine residues; most are either CC- or CXC-chemokines. The CC-chemokines RANTES, MIP-1α and MIP-1β, were shown to block replication of primary macrophage-tropic strains of HIV-1 (Cocchi et al., 1995). Using expression cloning techniques, Feng et al. (1996) discovered that the chemokine receptor fusin (later renamed CXCR4) was a fusion coreceptor for strains of HIV-1 adapted to growth on T cell lines. Shortly thereafter, several groups reported the cloning of CCR5, a CC chemokine receptor with specificity for RANTES, MIP-1α and MIP-1β (Combadiere et al., 1996; Raport et al., 1996; Samson et al., 1997), and others then demonstrated that CCR5 was the main entry cofactor used by primary macrophage-tropic HIV-1 isolates (Alkhatib et al., 1996; Choe et al., 1996; Deng et al., 1996; Doranz et al., 1996; Dragic et al., 1996). The patterns of CCR5 and CXCR4 expression helped solve long-standing riddles concerning the tropism of different strains of HIV-1. Macrophage-tropic, T-cell-line-tropic and dual-tropic viruses could be more descriptively classified as being R5, X4 and R5X4 viruses based on their abilities to utilize CCR5, CXCR4 or both receptors, respectively, for entry.

A variety of other chemokine receptors can function as HIV-1 coreceptors when over-expressed in vitro. The list includes CCR8, Apj, V28, US28, CCR2b, CCR3, gpr1, Bonzo (STRL33, TYMSTR), and BOB (gpr15). Clearly, proteins belonging to the chemokine receptor family have biochemical properties that promote HIV-1 membrane fusion. However, most of the above-mentioned coreceptors are not very efficient, are not normally coexpressed with CD4, and function only with certain strains of HIV-1, HIV-2 or SIV. The in vivo relevance of these alternative coreceptors has not been established.

Several factors make CCR5 an attractive target for new antiretroviral therapies. CCR5 plays a central role in HIV-1 transmission and pathogenesis, and naturally-occurring mutations in CCR5 confer protection from HIV-1 infection and disease progression. The most notable CCR5 polymorphism involves a 32 bp deletion in the coding region of CCR5 (Δ32) (Liu et al., 1996). The Δ32 allele encodes a nonfunctional receptor that fails to reach the cell surface. Individuals who possess one normal and one mutant CCR5 gene express lower levels of CCR5, and their T cells are less susceptible to R5 virus infection in vitro (Liu et al., 1996; Wu et al., 1997). Δ32 heterozygotes experience a milder course of disease characterized by reduced viral burdens and delayed progression to AIDS (Huang et al., 1996; Michael et al., 1997). These results support the concept that reducing CCR5 availability can lower viral replication and slow disease progression.

Individuals with two mutant CCR5 genes comprise a significant fraction of people of northern European descent; the demography is suggestive of a prior pandemic of a CCR5-using pathogen. Such individuals represent human CCR5 "knockouts" in that they do not express a functional CCR5 protein. Except in rare instances (Balotta et al., 1997; Biti et al., 1997; O'Brien et al., 1997), these individuals are resistant to HIV-1 infection (Huang et al., 1996; Liu et al., 1996; Michael et al., 1997; Samson et al., 1997), and their T cells cannot be infected with R5 viruses in vitro (Liu et al., 1996). These findings underscore the central role of CCR5 in HIV-1 transmission. In fact, it is now known that R5 viruses mediate transmission in nearly all cases and mediate progression to AIDS in most cases.

Importantly, individuals who lack CCR5 enjoy normal health and display no obvious immunologic or other defects. This may reflect the redundancy of chemokine signaling pathways and the rather limited pattern of expression of CCR5. CCR5 expression is largely confined to activated T cells and macrophages, which represent the primary targets for HIV-1 infection in vivo, although low-level CCR5 expression has been reported on other tissues, such as smooth muscle (Schecter et al., 2000).

CCR5 knockout mice have been generated and provide further insight into the effects of abrogating CCR5 function. CCR5 knockout mice develop normally and are ostensibly healthy, although minor alterations in immune responses can be observed upon challenge with particular pathogens (Huffnagle et al., 1999; Schuh et al., 2002; Tran et al., 2000; Zhou et al., 1998). In contrast, the CXCR4 knockout is a lethal phenotype in mice (Lapidot et al., 2001), and has not been observed in humans.

Taken together, these genetic analyses strongly support a new therapeutic approach based on CCR5 as a drug target. The error-prone nature of reverse transcriptase generates immense genetic diversity that fosters the development of drug-resistant isolates, and HIV-1's ability to utilize multiple fusion coreceptors provides one path to resistance. Drug-resistant viruses have been isolated for all marketed antiretrovirals, which nevertheless provide important therapeutic benefit when used in appropriate combinations. Thus, despite the potential emergence of drug-resistant viruses, CCR5-targeting agents may serve as a new treatment paradigm for HIV-1 infection.

Although the apparent non-essential nature of CCR5 suggests that CCR5 antagonists may be well tolerated in vivo, further studies are required to determine that long-term effects of abrogating CCR5 function in individuals whose immune systems developed in its presence. Such potentially deleterious effects may be mitigated by use of agents that bind to CCR5 and inhibit binding of HIV-1 thereto, but do not impair normal CCR5 function. One agent demonstrated to have such properties is the humanized anti-CCR5 mAb, PRO 140, which effectively blocks HIV-1 replication at concentrations that do not inhibit the physiologic activity of CCR5 (Olson et al., 1999). PRO 140 was identified using a fluorescence resonance energy transfer (RET) assay screen for anti-HIV activity. It is potently antiviral, having an $IC_{90}$ of about 4 µg/ml (Olson et al., 1999; Trkola et al., 2001) and protects diverse primary target cell types (Ketas et al., 2003; Olson and Maddon, 2003). Repeated administration of PRO 140 led to prolonged control of HIV-1 replication without viral escape in the hu-PBL SCID mouse model, and PRO 140 is currently in Phase 1 human clinical trials.

Subsequent to the identification of the small-molecule CCR5 antagonist, TAK-779 (Baba et al., 1999), several other small-molecule CCR5 antagonists have been identified. Four of these (SCH-C, SCH-D, UK-427,857, GW873140) have completed similarly designed Phase 1 studies in HIV-infected individuals (Reynes et al., 2002; Schurmann et al., 2004; Dorr et al., 2003; Lalezari et al., 2004). Each of these agents mediated dose-dependent ~1 $\log_{10}$ mean reductions in HIV-1 RNA levels during the treatment period of 10-14 days. As expected, viral loads rebounded to baseline levels following cessation of therapy. The most common drug-related side-effects were neurologic (headache, dizziness) and gastrointestinal (nausea, diarrhea, flatulence), and these were not dose limiting. With the exception of SCH-C (Reyes et al., 2001), none of the above-identified agents induced clinically significant changes in QTc intervals.

A double-blind, placebo-controlled, single oral dose study has also been conducted to evaluate the safety, tolerability, and pharmacokinetics of TAK-652, the successor compound to TAK-779, in healthy male volunteers (Baba et al., 2005). The single administration of TAK-652 solution was reportedly safe and well tolerated (Baba et al., 2005).

Overall, these studies provide preliminary validation of CCR5 as a target for HIV-1 therapy. While the small-molecule CCR5 antagonists represent patentably distinct chemical series with differing pharmacokinetic and metabolic properties, the compounds share many properties in their inhibition of CCR5 function, binding site on CCR5, resistance profiles, and dosing regimen. These similarities may conceivably limit the number of genuine treatment options afforded by small-molecule CCR5 antagonists. Moreover, it remains to be determined whether there are untoward consequences of chronic blockade of CCR5 function, and the utility of small-molecule CCR5 antagonists for HIV-1 therapy remains to be established by demonstration of appropriate safety and efficacy in Phase 3 clinical studies.

Monoclonal Antibody Therapeutics

In recent years, mAb products have provided new standards of care in diverse disease settings. Currently, 18 mAbs are approved by the U.S. Food and Drug Administration (FDA) for indications including cancer, autoimmune disease, transplant rejection and viral infection. Notably, 14 mAbs have been approved since 2000. In many instances, mAbs provide safety, efficacy and ease-of-use profiles that are unrivalled by small-molecule compounds. Examples include Synagis (MedImmune, Inc., Gaithersburg, Md.), a humanized mAb to respiratory syncytial virus (RSV), and Rituxan (Genentech, San Francisco, Calif.), an anti-CD20 mAb that provides the standard of care for non-Hodgkin's lymphoma.

The humanized anti-CCR5 mAb, PRO 140, is structurally, functionally and mechanistically distinct from the small-molecule CCR5 antagonists and therefore represents a unique CCR5 inhibitor class. PRO 140 is a humanized version of the murine mAb, PA14, which was generated against $CD4^+$ $CCR5^+$ cells (Olson et al., 1999). PRO 140 binds to CCR5 expressed on the surface of a cell, and potently inhibits HIV-1 entry and replication at concentrations that do not affect CCR5 chemokine receptor activity in vitro and in the hu-PBL-SCID mouse model of HIV-1 infection (Olson et al., 1999; Trkola et al., 2001). The latter finding provides in vivo proof-of-concept for PRO 140 anti-HIV-1 therapy, and PRO 140 is currently undergoing Phase 1a clinical studies.

Important differences between PRO 140 and small-molecule CCR5 antagonists are summarized in Table 2. It is evident from Table 2 that, whereas small-molecule CCR5 antagonists in development share many properties, PRO 140 is clearly distinct from these small-molecule inhibitors. The differences between the two CCR5 inhibitor classes reveal that PRO 140 may offer a fundamentally distinct, and in many ways complementary, product profile from that of small-molecule CCR5 antagonists. Indeed, PRO 140 represents a novel therapeutic approach to treating HIV-1 infection and could play an important role in HIV-1 therapy irrespective of whether small-molecule CCR5 antagonists are ultimately clinically approved.

Synergistic Inhibition of HIV-1 Infection by Different Classes of Inhibitors

Synergistic inhibition of HIV-1 entry has previously been demonstrated using certain anti-Env antibodies in combination with other anti-Env antibodies (Thali et al., 1992; Tilley et al., 1992; Laal et al., 1994; Vijh-Warrier et al., 1996; Li et al., 1997; Li et al., 1998), anti-CD4 antibodies (Burkly et al., 1995), or CD4-based proteins (Allaway et al., 1993). Similarly, synergies have been observed using anti-CCR5 antibodies in combination with other anti-CCR5 antibodies, CC-chemokines, or CD4-based proteins (Olson et al., 1999). Prior studies described in PCT International Publication No. WO 00/35409, published Jun. 22, 2000, examined combinations of HIV-1 attachment inhibitors and CCR5 coreceptor inhibitors. Prior studies described in PCT International Publication No. WO 01/55439, published Aug. 2, 2001, examined combinations of inhibitors of gp41 fusion intermediates and HIV-1 attachment. Prior studies described in PCT International Publication No. WO 02/22077, published Mar. 21, 2002, examined combinations of fusion inhibitors and CCR5 coreceptor inhibitors, as well as the triple combination of fusion inhibitors, CCR5 coreceptor inhibitors and HIV-1 attachment inhibitors. However, no prior study has examined the combination of different classes of CCR5 coreceptor inhibitors, such as anti-CCR5 mAbs and non-antibody CCR5 antagonists.

TABLE 2

Comparison of PRO 140 and small-molecule CCR5 antagonists under development

|  | Small Molecules | PRO 140 |
| --- | --- | --- |
| Identification Screen | Chemokine Binding | HIV-1 Entry |
| Block Natural Activity of CCR5 | Yes | No |
| Potential for Immune Suppression/Dysregulation | Yes | No |

TABLE 2-continued

Comparison of PRO 140 and small-molecule CCR5 antagonists under development

|  | Small Molecules | PRO 140 |
| --- | --- | --- |
| Tolerability | Cardiac, Neurological Toxicities for some | No Toxicity |
| Binding site on CCR5 | Common Hydrophobic Pocket defined by Transmembrane Regions of CCR5 | Extracellular Epitope that spans Multiple Hydrophilic Domains |
| Viral Cross-Resistance | Significant | Limited |
| Development of Resistance In Vitro | 6 to 19 weeks | None at 40 weeks |
| Drug-Drug Interactions | Significant | Unlikely |
| Food Interactions | Significant | Unlikely |
| Dosing | Once or Twice Daily | Biweekly to Monthly |

SUMMARY OF THE INVENTION

This method provides a method for reducing HIV-1 viral load in an HIV-1-infected human subject which comprises administering to the subject at a predefined interval effective HIV-1 viral load-reducing doses of (a) a humanized antibody designated PRO 140, or of (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099), wherein the effective HIV-1 viral load-reducing dose comprises from 0.1 mg per kg to 10 mg per kg of the subject's body weight, so as to thereby reduce the subject's HIV-1 viral load.

This invention also provides a method for inhibiting in a human subject the onset or progression of an HIV-1-associated disorder, the inhibition of which is effected by inhibiting fusion of HIV-1 to CCR5+CD4+ target cells in the subject, comprising administering to the subject at a predefined interval effective fusion-inhibitory doses of a humanized antibody designated PRO 140, or of an anti-CCR5 receptor antibody which (i) binds to CD4+CCR5+ cells in the subject and inhibits fusion of HIV-1 with such cells, (ii) inhibits HIV-1 fusion with the subject's CD4+CCR5+ cells with a potency characterized by an IC90 of 10 µg/ml or less, (iii) coats the subject's CD4+CCR5+ cells without reducing the of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099), wherein each administration of the antibody delivers to the subject from 0.1 mg per kg to 10 mg per kg of the subject's body weight, so as to thereby inhibit the onset or progression of the HIV-1-associated disorder in the subject.

This invention further provides a method for reducing the likelihood of a human subject's contracting an HIV-1 infection which comprises administering to the subject at a predefined interval effective fusion-inhibitory doses of a humanized antibody designated PRO 140, or of an anti-CCR5 receptor antibody which (i) binds to CD4+CCR5+ cells in the subject and inhibits fusion of HIV-1 with such cells, (ii) inhibits HIV-1 fusion with the subject's CD4+CCR5+ cells with a potency characterized by an IC90 of 10 µg/ml or less, (iii) coats the subject's CD4+CCR5+ cells without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099), wherein each administration of the antibody delivers to the subject from 0.1 mg per kg to 10 mg per kg of the subject's body weight, so as to thereby reduce the likelihood of the subject's contracting an HIV-1 infection.

The present invention provides a method for treating a subject infected with HIV-1 comprising administering to the subject (a) an antibody which (i) binds to a CCR5 receptor on the surface of a CD4+ cell and (ii) inhibits fusion of HIV-1 to a CCR5+CD4+ cell, and (b) a non-antibody antagonist of a CCR5 receptor, in amounts effective to treat the subject.

This invention also provides a method for inhibiting in a subject the onset or progression of an HIV-1-associated disorder, the inhibition of which is effected by inhibiting fusion of HIV-1 to CCR5+CD4+ target cells in the subject, comprising administering to the subject (a) an antibody which (i) binds to a CCR5 receptor on the surface of a CD4+ cell and (ii) inhibits fusion of HIV-1 to a CCR5+CD4+ cell, and (b) a non-antibody antagonist of a CCR5 receptor, in amounts effective to inhibit fusion of HIV-1 to the CCR5+CD4+ target cells, so as to thereby inhibit the onset or progression of the HIV-1-associated disorder in the subject.

The invention further provides a method for reducing the likelihood of a subject's contracting an HIV-1 infection comprising administering to the subject (a) an antibody which (i) binds to a CCR5 receptor on the surface of a CD4+ cell and (ii)

inhibits fusion of HIV-1 to a CCR5⁺CD4+ cell, and (b) a non-antibody antagonist of a CCR5 receptor, in amounts effective to reduce the likelihood of the subject's contracting an HIV-1 infection.

This invention also provides a method of potentiating HIV-1 inhibitory activity of (i) an anti-CCR5 receptor monoclonal antibody or (ii) a non-antibody CCR5 receptor antagonist in the treatment of HIV-1 infection in a subject, comprising: administering to the subject an HIV-1 inhibitory activity potentiating amount of the anti-CCR5 receptor monoclonal antibody in combination with an HIV-1 inhibitory activity potentiating amount of a non-antibody CCR5 receptor antagonist, wherein the combination produces a synergistic effect on inhibiting HIV-1 infection, thereby potentiating the inhibitory activity of (i) the anti-CCR5 receptor monoclonal antibody or (ii) the non-antibody CCR5 receptor antagonist. In one embodiment, due to the synergistic effect, the non-antibody CCR5 receptor antagonist causes an approximately 4- to 10-fold dose reduction of the anti-CCR5 receptor monoclonal antibody and the anti-CCR5 receptor monoclonal antibody causes an approximately 3- to 16-fold dose reduction of the non-antibody CCR5 receptor antagonist.

Figure 1:
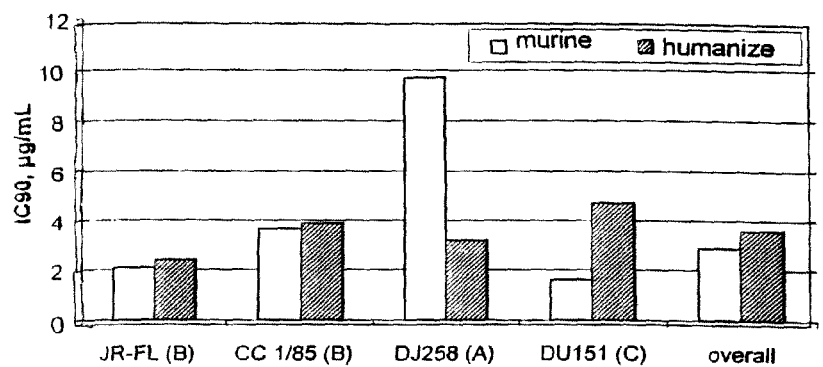
FIG. 1

Humanized PRO140 is potently antiviral. The in vitro neutralization activity of murine and humanized PRO 140 was tested against four primary R5 HIV-1 isolates using a whole virus replication assay. The data reflect the median values from 8 or more independent assays. The genetic subtypes of the viruses are indicated in parentheses.

FIG. 2

Antiviral activity is independent of target cell. Inhibition of infection of four different target cells by three primary R5 HIV-1 isolates with was tested.

FIG. 3

In vitro HIV-1 susceptibility to PRO 140 quantified using the PhenoSense™ entry assay. PRO 140 was tested for activity against 20 primary HIV-1 isolates in the PhenoSense HIV Entry™ assay at ViroLogic, Inc. Drug susceptibility is reported as $IC_{50}$ values, which represent the concentration required for 50% inhibition of viral infectivity.

FIG. 4

PRO 140 blocks HIV-1 but not chemokine signaling. The effects of PRO 140 on the inhibition of RANTES-induced calcium mobilization in L1.2-CCR5 cells and on inhibition of HIV-1$_{JR-FL}$ replication in PBMC cultures were determined. Similar results were obtained for MIP-1α and MIP-1β.

FIG. 5

PRO 140 provides prolonged control of viral replication in HIV-1-infected mice. SCID mice were reconstituted with normal human peripheral blood mononuclear cells and infected 2 weeks later with HIV-1$_{JR-CSF}$. Multiple doses of PRO 140 were administered following attainment of steady state viral levels. Plasma viral loads pre- and post-injection are indicated.

FIG. 6

PRO 140 coats but does not deplete CCR5 lymphocytes. Healthy male volunteers (n=4) were treated with a single intravenous infusion of PRO 140 at a dose level of 2 mg/kg. At the indicated times post-treatment, blood was collected and analyzed for CCR5 lymphocyte levels. The group mean values and standard deviations are indicated.

FIG. 7

Serum concentrations of PRO 140. Healthy male volunteers were treated with a single intravenous infusion of PRO 140 at dose levels of 0.1, 0.5 and 2.0 mg/kg, as indicated. At the indicated times post-treatment, serum was collected, cryopreserved, and analyzed for PRO 140 levels. Data for individual patients are indicated.

FIG. 8

PRO 140 does not affect plasma chemokine levels. Healthy male volunteers were treated with a single intravenous infusion of 0.1 mg/kg PRO 140 (Cohort 1), 0.5 mg/kg PRO 140 (Cohort 2) or matched placebo. At the indicated times post-treatment, plasma was collected, cryopreserved and analyzed for levels of RANTES. The Lower Limit of Quantification of the assay was 415 pg RANTES/mL plasma. Data represent the group mean values.

FIG. 9

Scheme for chemical synthesis of SCH-D.

FIG. 10

Scheme for chemical synthesis of TAK-779. The method is as described in Shiraishi et al., 2000.

FIG. 11

Scheme for chemical synthesis of UK-427,857. The method is as described in PCT International Publication No. WO 01/90106 A2, published Nov. 29, 2001.

FIG. 12

Synergistic inhibition of HIV-1 fusion exhibited by PRO 140 with different compounds. Interactions between PRO 140 and small-molecule, peptide, mAb, and chimeric CD4-immunoglobulin inhibitors of CCR5, CD4, gp120 and gp41 targets for inhibiting HIV-1 fusion were assessed using the RET assay. Mean combination index (CI) values with 95% confidence intervals are plotted for data obtained using the compounds combined in a 1:1 molar ratio. A CI value of <1 indicates synergistic interactions; a CI value of 1 indicates additive interactions; and a CI value of >1 indicates antagonistic interactions.

FIG. 13

PRO 140 coats but does not deplete lymphocytes. Healthy male volunteers (n=4) were treated with a single intravenous infusion of PRO 140 at a dose level of 5 mg/kg. At the indicated times post-treatment, blood was collected and analyzed for CCR5 lymphocyte levels. The group mean values and standard deviations are indicated.

FIG. 14

PRO 140 is active against HIV-1 strains that are resistant to small-molecule CCR5 antagonists. Variants of HIV-1 resistant to AD101 (a small-molecule CCR5 inhibitor structurally related to SCH-C) and SCH-D (Kuhmann et al., 2004; Maroznan et al. 2005) were tested for sensitivity to the anti-CCR5 mAb, PA14. The extent of viral replication in primary CD4+ T-cells is represented relative to p24 antigen production in the absence of any inhibitor, which is defined as 100%. Individual data points were the average of values derived from 4 separate experiments, each performed using duplicate wells. The data show that whereas the AD101- and SCH-D-resistant HIV-1 variants were resistant to SCH-C and SCH-D, respectively, replication of these variants was potently inhibited by PA14 (Maroznan et al. 2005).

FIG. 15

Dose-response curves for inhibition of HIV-1$_{JR-FL}$ envelope-mediated membrane fusion by combinations of CCR5 inhibitors. Dilutions were analyzed in triplicate wells, and the data points depict the mean and standard deviations of replicates. (A) PRO 140 and UK-427,857 were tested individually and in a 1:1 fixed molar ratio over the indicated range of concentrations. In the experiment depicted, IC50 and IC90 values were 2.9 nM and 11 nM for PRO140, 5.0 nM and 21 nM for UK-427,857, and 2.1 nM and 4.6 nM for the combination. CI50 and CI90 values were 0.58 and 0.32, respectively. (B) SCH-D and UK-427,857 were tested individually and in a 1:1 fixed molar ratio over the indicated range of concentrations. In the experiment depicted, IC50 and IC90 values were 5.5 nM and 34 nM for SCH-D, 9.7 nM and 59 nM for UK-427,857, and 6.1 nM and 31 nM for the combination. CI50 and CI90 values were 0.87 and 0.73, respectively.

FIG. 16

Inhibition of PRO 140-PE binding to CEM.NKR-CCR5 cells by unlabeled PRO 140, UK-427,857 and SCH-D. CEM.NKR-CCR5 cells were incubated with varying concentrations of unlabeled PRO 140, UK-427,857 or SCH-D for 30 min at room temperature in PBSA buffer prior to addition of 5 nM PRO 140-PE for an additional 30 min. Cells were washed and then analyzed by flow cytometry for both the mean fluorescence intensity (MFI) of binding and the percent of cells gated for positive binding of PRO 140-PE. Inhibition was assessed on the basis of both MFI (A) and percent cells gated (B).

FIG. 17

Inhibition of $^3$H-UK-427,857 binding by unlabeled UK-427,857, SCH-D and PRO 140. (A) CEM.NKR-CCR5 cells were pre-incubated with varying concentrations of unlabeled UK-427,857, SCH-D or PRO 140 for 30 min in PBSA buffer at ambient temperature prior to the addition of at 2 nM $^3$H-UK-427,857 for an additional 30 min. Cells were washed and then analyzed for radioactivity by scintillation counting. (B) The stability of UK-427,857 binding under the assay conditions was examined by pre-incubating CEM.NKR-CCR5 cells with 2 nM $^3$H-UK-427,857 prior to washing, addition of unlabeled compounds for 30 min, and processing as described above.

DETAILED DESCRIPTION OF THE INVENTION

Terms

As used in this application, except as otherwise expressly provided herein, each of the following terms shall have the meaning set forth below.

"Administering" refers to delivering in a manner which is effected or performed using any of the various methods and delivery systems known to those skilled in the art. Administering can be performed, for example, topically, intravenously, pericardially, orally, parenterally, via implant, transmucosally, transdermally, intradermally, intramuscularly, subcutaneously, intraperitoneally, intrathecally, intralymphatically, intralesionally, epidurally, or by in vivo electroporation. An agent or composition may also be administered in an aerosol, such as for pulmonary and/or intranasal delivery. Administering can also be performed, for example, once, a plurality of times, and/or over one or more extended periods.

An "antibody" shall include, without limitation, an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. "Antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Methods for humanizing antibodies are well known to those skilled in the art. "Antibody" also includes, without limitation, a fragment or portion of any of the afore-mentioned immunoglobulin molecules and includes a monovalent and a divalent fragment or portion. Antibody fragments include, for example, Fc fragments and antigen-binding fragments (Fab).

An "anti-chemokine receptor antibody" refers to an antibody which recognizes and binds to an epitope on a chemokine receptor. As used herein, "anti-CCR5 antibody" refers to an antibody which recognizes and binds to an epitope on the CCR5 chemokine receptor.

"Attachment" means the process that is mediated by the binding of the HIV-1 envelope glycoprotein to the human CD4 receptor, which is not a fusion coreceptor.

As used herein, "CCR5" is a chemokine receptor which binds members of the C—C group of chemokines and whose amino acid sequence comprises that provided in Genbank Accession Number 1705896 and related polymorphic variants. As used herein, CCR5 includes, without limitation, extracellular portions of CCR5 capable of binding the HIV-1 envelope protein. "CCR5" and "CCR5 receptor" are used synonymously.

"CD4" means the mature, native, membrane-bound CD4 protein comprising a cytoplasmic domain, a hydrophobic transmembrane domain, and an extracellular domain which binds to the HIV-1 gp120 envelope glycoprotein.

"CDR", or complementarity determining region, means a highly variable sequence of amino acids in the variable domain of an antibody.

A "cell" includes a biological cell, e.g., a HeLa cell, and a non-biological cell, e.g., a phospholipid vesicle or virion. A "cell susceptible to HIV infection" may also be referred to as a "target cell" and includes a cell capable of being infected by or fusing with HIV or an HIV-infected cell.

"CXCR4" is a chemokine receptor which binds members of the C—X—C group of chemokines and whose amino acid sequence comprises that provided in Genbank Accession No 400654 and related polymorphic variants. As used herein, CXCR4 includes extracellular portions of CXCR4 capable of binding the HIV-1 envelope protein.

"Exposed" to HIV-1 refers to contact with HIV-1 such that infection could result.

A "fully human" antibody refers to an antibody wherein all of the amino acids correspond to amino acids in human immunoglobulin molecules. "Fully human" and "human" are used synonymously.

"HIV" refers to the human immunodeficiency virus. HIV shall include, without limitation, HIV-1. HIV-1 includes but is not limited to extracellular virus particles and the forms of HIV-1 associated with HIV-1 infected cells. The human immunodeficiency virus (HIV) may be either of the two known types of HIV (HIV-1 or HIV-2). The HIV-1 virus may represent any of the known major subtypes (classes A, B, C, D, E, F, G and H) or outlying subtype (Group O). HIV-1$_{JR-FL}$ is a strain that was originally isolated at autopsy from the brain tissue of an AIDS patient. The virus has been cloned and the DNA sequences of its envelope glycoproteins are known (GenBank Accession No. U63632). In terms of sensitivity to inhibitors of viral entry, HIV-1$_{JR-FL}$ is known to be highly representative of primary HIV-1 isolates.

A "humanized" antibody refers to an antibody wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules, whereas some, most or all amino acids within one or more CDR regions are unchanged. Small additions, deletions, insertions, substitutions or modifications of amino acids are permissible as long as they do not abrogate the ability of the antibody to bind a given antigen. Suitable human immunoglobulin molecules include IgG1, IgG2, IgG3, IgG4, IgA, IgE and IgM molecules. A "humanized" antibody retains an antigenic specificity similar to that of the original antibody.

"Monoclonal antibodies," also designated a mAbs, are antibody molecules whose primary sequences are essentially identical and which exhibit the same antigenic specificity. Monoclonal antibodies may be produced by hybridoma, recombinant, transgenic or other techniques known to those skilled in the art.

A "non-antibody antagonist of a CCR5 receptor" refers to an agent that does not comprise an antibody, and which binds to a CCR5 receptor and inhibits the activity of this receptor. Such inhibition can include inhibiting the binding of HIV-1 to the CCR5 receptor. By way of example, non-antibody antagonists include nucleic acids, carbohydrates, lipids, oligopeptides, and small organic molecules.

"Reducing the likelihood of a subject's contracting a viral infection" means reducing the likelihood of the subject's becoming infected with the virus by at least two-fold. For example, if a subject has a 1% chance of becoming infected with the virus, a two-fold reduction in the likelihood of the subject contacting a viral infection would result in the subject having a 0.5% chance of becoming infected with the virus. In the preferred embodiment of this invention, reducing the likelihood of the subject's contracting a viral infection means reducing the likelihood of the subject's becoming infected with the virus by at least ten-fold.

A "small-molecule" CCR5 receptor antagonist includes, for example, a small organic molecule which binds to a CCR5 receptor and inhibits the activity of the receptor. Such inhibition includes, e.g., inhibiting the binding of HIV-1 to the receptor. In one embodiment, the small organic molecule has a molecular weight less than 1,500 daltons. In another embodiment, the molecule has a molecular weight less than 600 daltons.

"Subject" includes any animal or artificially modified animal capable of becoming infected with HIV. Animals include, but are not limited to, humans, non-human primates, dogs, cats, rabbits, ferrets, and rodents such as mice, rats and guinea pigs. Artificially modified animals include, but are not limited to, SCID mice with human immune systems. In the preferred embodiment, the subject is a human.

"Synergy" between two or more agents refers to the combined effect of the agents which is greater than their additive effects. Synergistic, additive or antagonistic effects between agents may be quantified by analysis of the dose-response curves using the Combination Index (CI) method. A CI value greater than 1 indicates antagonism; a CI value equal to 1 indicates an additive effect; and a CI value less than 1 indicates a synergistic effect. In one embodiment, the CI value of a synergistic interaction is less than 0.9. In another embodiment, the CI value is less than 0.8. In a preferred embodiment, the CI value is less than 0.7.

"Treating an HIV-1 infection in a subject" refers to slowing, stopping or reversing the progression of an HIV-1 disorder in the subject. In the preferred embodiment, "treating" refers to reversing the progression to the point of eliminating the disorder. As used herein, "treating" also means reducing the number of viral infections, reducing the number of infectious viral particles, reducing the number of virally infected cells, or ameliorating symptoms associated with HIV-1. Reducing viral load in a subject is one embodiment of treating the subject.

EMBODIMENTS OF THE INVENTION

This method provides a method for reducing HIV-1 viral load in an HIV-1-infected human subject which comprises administering to the subject at a predefined interval effective HIV-1 viral load-reducing doses of (a) a humanized antibody designated PRO 140, or of (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099), wherein the effective HIV-1 viral load-reducing dose comprises from 0.1 mg per kg to 10 mg per kg of the subject's body weight, so as to thereby reduce the subject's HIV-1 viral load.

In one embodiment, the anti-CCR5 receptor monoclonal antibody binds to the same CCR5 epitope as that to which PRO 140 binds. The anti-CCR5 receptor monoclonal antibody can be, for example, a humanized, human, or chimeric antibody. In the preferred embodiment, the antibody administered to the subject is the antibody designated PRO 140.

In one embodiment, the effective viral load-reducing dose is from 0.25 mg per kg to 7.5 mg per kg of the subject's body weight. In another embodiment, the dose is from 0.5 mg per kg to 5 mg per kg of the subject's body weight. In another embodiment, the dose is from 1 mg per kg to 3 mg per kg of the subject's body weight. In another embodiment, the dose is 2 mg per kg of the subject's body weight.

In another embodiment, the effective viral load-reducing dose is sufficient to achieve in the subject a serum concentration of the antibody of at least 400 ng/ml. In a further embodiment, the doses administered at regular intervals are sufficient to achieve and maintain in the subject a serum concentration of the antibody of at least 1 µg/ml. In a further embodiment, the doses are sufficient to achieve and maintain in the subject a serum concentration of the antibody of about 3 to about 12 µg/ml. In a further embodiment, the doses are sufficient to achieve and maintain in the subject a serum concentration of the antibody of at least 5 µg/ml. In a further embodiment, the doses are sufficient to achieve and maintain in the subject a serum concentration of the antibody of at least 10 µg/ml. In a further embodiment, the doses are sufficient to achieve and maintain in the subject a serum concentration of the antibody of at least 25 µg/ml. In a further embodiment, the doses are sufficient to achieve and maintain in the subject a serum concentration of the antibody of at least 50 µg/ml.

In one embodiment of the invention, the predefined interval is at least once weekly. In another embodiment, the predefined interval is every two to four weeks. In a further embodiment, the predefined interval is every two weeks, or every four weeks. In a further embodiment, the predefined interval is at least once monthly, every six weeks or every eight weeks. In another embodiment of the invention, the reduction of the subject's HIV-1 viral load is maintained for at least one week. In another embodiment, the subject's HIV-1 viral load is maintained for at least two weeks. In another embodiment, the reduction of the subject's HIV-1 viral load is maintained for at least four weeks. In another embodiment, the reduction of the subject's HIV-1 viral load is maintained for at least three months.

In one embodiment, the antibody is administered via intravenous infusion. In another embodiment, the antibody is administered via subcutaneous injection. In one embodiment, the subject's HIV-1 viral load is reduced by at least 50% following administration of the antibody. In another embodiment, the subject's HIV-1 viral load is reduced by at least 70% following administration of the antibody, and preferably, is reduced by at least 90% following administration of the antibody.

In one embodiment of this invention, the method further comprises administering to the subject at least one anti-HIV-1 anti-retroviral agent. The anti-HIV-1 anti-retroviral agent can be, for example, a nonnucleoside reverse transcriptase inhibitor (NNRTI), a nucleoside reverse transcriptase inhibitor (NRTI), a protease inhibitor (PI), a fusion inhibitor, or any combination thereof. In one embodiment, the subject is treatment-naïve. In the preferred embodiment, the subject is treatment-experienced.

In another embodiment, (a) prior to administering the monoclonal antibody to the subject, the subject has received treatment with at least one anti-HIV-1 anti-retroviral agent, and (b) concurrent with administering the monoclonal antibody, the subject continues to receive treatment with the agent or agents, so as to enhance the reduction of HIV-1 viral load in the subject. The anti-HIV-1 anti-retroviral agent can be, for example, a nonnucleoside reverse transcriptase inhibitor (NNRTI), a nucleoside reverse transcriptase inhibitor (NRTI), a protease inhibitor (PI), a fusion inhibitor, or any combination thereof.

This invention also provides a method for inhibiting in a human subject the onset or progression of an HIV-1-associated disorder, the inhibition of which is effected by inhibiting fusion of HIV-1 to $CCR5^+CD4^+$ target cells in the subject, comprising administering to the subject at a predefined interval effective fusion-inhibitory doses of a humanized antibody designated PRO 140, or of an anti-CCR5 receptor antibody which (i) binds to CD4+CCR5+ cells in the subject and inhibits fusion of HIV-1 with such cells, (ii) inhibits HIV-1 fusion with the subject's CD4+CCR5+ cells with a potency characterized by an IC90 of 10 μg/ml or less, (iii) coats the subject's CD4+CCR5+ cells without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099), wherein each administration of the antibody delivers to the subject from 0.1 mg per kg to 10 mg per kg of the subject's body weight, so as to thereby inhibit the onset or progression of the HIV-1-associated disorder in the subject.

This invention further provides a method for reducing the likelihood of a human subject's contracting an HIV-1 infection which comprises administering to the subject at a predefined interval effective fusion-inhibitory doses of a humanized antibody designated PRO 140, or of an anti-CCR5 receptor antibody which (i) binds to CD4+CCR5+ cells in the subject and inhibits fusion of HIV-1 with such cells, (ii) inhibits HIV-1 fusion with the subject's CD4+CCR5+ cells with a potency characterized by an IC90 of 10 μg/ml or less, (iii) coats the subject's CD4+CCR5+ cells without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099), wherein each administration of the antibody delivers to the subject from 0.1 mg per kg to 10 mg per kg of the subject's body weight, so as to thereby reduce the likelihood of the subject's contracting an HIV-1 infection. In one embodiment, the subject has been exposed to HIV-1. In another embodiment, the subject is at risk of being exposed to HIV-1.

The present invention also provides a method for reducing HIV-1 viral load in an HIV-1-infected human subject who has developed resistance to a form of anti-HIV-1 therapy, which method comprises administering to the subject at a predefined interval effective HIV-1 viral load-reducing doses of (a) a humanized antibody designated PRO 140, or of (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099), wherein the effective HIV-1 viral load-reducing dose comprises from 0.1 mg per kg to 10 mg per kg of the subject's body weight, so as to thereby reduce the subject's HIV-1 viral load.

In one embodiment, the form of anti-HIV-1 therapy is a nonnucleoside reverse transcriptase inhibitor (NNRTI), a nucleoside reverse transcriptase inhibitor (NRTI), a protease inhibitor (PI), a fusion inhibitor, or any combination thereof. In another embodiment, the fusion inhibitor is a non-antibody CCR5 antagonist. In a further embodiment, the non-antibody CCR5 antagonist is a small-molecule CCR5 antagonist. In yet another embodiment, the small-molecule CCR5 antagonist is orally administered.

In the methods of this invention, the antibody may be administered at the same time, concurrently, prior to the administration of the small-molecule CCR5 antagonist or subsequent to the administration of the small-molecule CCR5 antagonist. With respect to the administration of two or more agents to a subject in order to treat the subject, each agent may be administered to the subject within the same treatment time period as is each other agent. The agents can be administered together, at the same time and in the same or different compositions or via the same or different routes of administration. Alternatively, each agent is administered via a dosing regimen (e.g., frequency, route and amount) different from that by which each other agent is administered. For example, the first of two administered agents (e.g., an antibody) may be administered via subcutaneous injection at two-week intervals for a one-year treatment time period, whereas during that same one-year period, the second administered agent (e.g., a small molecule) is orally administered twice per day. Accordingly, "concurrent administration" refers to the administration of at least two agents within one treatment period.

This invention also provides a method for treating a subject infected with HIV-1 comprising administering to the subject (a) an antibody which (i) binds to a CCR5 receptor on the surface of the subject's $CD4^+$ cells and (ii) inhibits fusion of HIV-1 to the subject's $CCR5^+CD4+$ cells, and (b) a non-antibody CCR5 receptor antagonist, in amounts effective to treat the subject.

This invention also provides a method for inhibiting in a subject the onset or progression of an HIV-1-associated disorder, the inhibition of which is effected by inhibiting fusion of HIV-1 to $CCR5^+CD4^+$ target cells in the subject, comprising administering to the subject (a) an antibody which (i) binds to a CCR5 receptor on the surface of the subject's $CD4^+$ cells and (ii) inhibits fusion of HIV-1 to the subject's $CCR5^+$ CD4+ cells, and (b) a non-antibody CCR5 receptor antagonist, in amounts effective to inhibit the onset or progression of the HIV-1-associated disorder in the subject.

This invention further provides a method for reducing the likelihood of a subject's contracting an HIV-1 infection comprising administering to the subject (a) an antibody which (i) binds to a CCR5 receptor on the surface of the subject's $CD4^+$ cells and (ii) inhibits fusion of HIV-1 to the subject's $CCR5^+$ CD4+ cells, and (b) a non-antibody CCR5 receptor antagonist, in amounts effective to reduce the likelihood of the subject's contracting an HIV-1 infection. In one embodiment, the subject has been exposed to HIV-1. In another embodiment, the subject is at risk of being exposed to HIV-1.

This invention also relates to the effect of the combination of distinct classes of compounds which bind to CCR5, namely anti-CCR5 mAbs and non-antibody CCR5 antagonists, on HIV-1 fusion to, and entry into, susceptible target cells. Synergistic inhibition of HIV-1 infection of target cells has previously been demonstrated using combinations of different HIV-1 entry inhibitors. However, no prior study has examined the combination of different classes of inhibitors which target the same CCR5 coreceptor.

Specifically, this invention also provides a method for treating a subject infected with HIV-1 comprising administering to the subject (a) an antibody which (i) binds to a CCR5 receptor on the surface of the subject's $CD4^+$ cells and (ii) inhibits fusion of HIV-1 to the subject's $CCR5^+CD4+$ cells and (b) a non-antibody CCR5 receptor antagonist, in amounts effective to treat the subject.

This invention further provides a method for inhibiting in a subject the onset or progression of an HIV-1-associated disorder, the inhibition of which is effected by inhibiting fusion of HIV-1 to $CCR5^+CD4^+$ target cells in the subject, comprising administering to the subject (a) an antibody which (i) binds to a CCR5 receptor on the surface of the subject's $CD4^+$ cells and (ii) inhibits fusion of HIV-1 to the subject's $CCR5^+$ CD4+ cells, and (b) a non-antibody CCR5 receptor antagonist, in amounts effective to inhibit the onset or progression of the HIV-1-associated disorder in the subject.

This invention also provides a method for reducing the likelihood of a subject's contracting an HIV-1 infection comprising administering to the subject (a) an antibody which (i) binds to a CCR5 receptor on the surface of the subject's $CD4^+$ cells and (ii) inhibits fusion of HIV-1 to the subject's $CCR5^+$ CD4+ cells, and (b) a non-antibody CCR5 receptor antagonist, in amounts effective to reduce the likelihood of the subject's contracting an HIV-1 infection. In one embodiment, the subject has been exposed to HIV-1. In another embodiment, the subject is at risk of being exposed to HIV-1.

This invention also provides a method of potentiating HIV-1 inhibitory activity of (i) an anti-CCR5 receptor monoclonal antibody or (ii) a non-antibody CCR5 receptor antagonist in the treatment of HIV-1 infection in a subject, comprising: administering to the subject an HIV-1 inhibitory activity potentiating amount of the anti-CCR5 receptor monoclonal antibody in combination with an HIV-1 inhibitory activity potentiating amount of a non-antibody CCR5 receptor antagonist, wherein the combination produces a synergistic effect on inhibiting HIV-1 infection, thereby potentiating the inhibitory activity of (i) the anti-CCR5 receptor monoclonal antibody or (ii) the non-antibody CCR5 receptor antagonist. In one embodiment, due to the synergistic effect, the non-antibody CCR5 receptor antagonist causes an approximately 4- to 10-fold dose reduction of the anti-CCR5 receptor monoclonal antibody and the anti-CCR5 receptor monoclonal antibody causes an approximately 3- to 16-fold dose reduction of the non-antibody CCR5 receptor antagonist.

In another embodiment, the method comprises an HIV-1 inhibitory activity potentiating amount of one or more non-antibody CCR5 receptor antagonists. In another embodiment, the method comprises an HIV-1 inhibitory activity potentiating amount of one or more anti-CCR5 receptor monoclonal antibodies. In yet another embodiment, the anti-CCR5 receptor monoclonal antibody and the non-antibody CCR5 receptor antagonist are concurrently administered to the subject.

In one embodiment, the monoclonal antibody is PA14 produced by the hybridoma cell line designated PA14 (ATCC Accession No. HB-12610), or an antibody that competes with monoclonal antibody PA-14 in binding to the CCR5 receptor. In another embodiment, the monoclonal antibody is the humanized antibody designated PRO 140, or an antibody that competes with PRO 140 in binding to the CCR5 receptor, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I) (ATCC Deposit Designation PTA-4099). In another embodiment, the monoclonal antibody is the humanized antibody designated PRO140. In yet another embodiment, the monoclonal antibody is CCR5mAb004 or 2D7.

In one embodiment, the non-antibody CCR5 receptor antagonist is SCH-D, TAK-779, TAK-652, UK-427,857, RANTES, GW873140, or a combination thereof. In another embodiment, the non-antibody CCR5 receptor antagonist is a small organic molecule that competes with SCH-D in binding to the CCR5 receptor. In another embodiment, the non-antibody CCR5 receptor antagonist is a small organic molecule that competes with UK-427,857 in binding to the CCR5 receptor. In yet another embodiment, the non-antibody CCR5 receptor antagonist is a small organic molecule that competes with TAK-779 in binding to the CCR5 receptor. In one embodiment, the non-antibody CCR5 receptor antagonist is a small organic molecule that competes with TAK-652 in binding to the CCR5 receptor. In another embodiment, the non-antibody CCR5 receptor antagonist is a small organic molecule that competes with GW873140 in binding to the CCR5 receptor.

In one embodiment of any of the methods described herein, the anti-CCR5 antibody is a monoclonal antibody. In another embodiment, the antibody is a polyclonal antibody. In a further embodiment, the antibody is a humanized antibody. In a still further embodiment, the antibody is a human antibody. In an additional embodiment, the antibody is a chimeric antibody. In one embodiment, the antibody is the anti-CCR5 human antibody designated CCR5mAb004, produced by Human Genome Sciences.

Murine hybridomas secreting monoclonal antibodies PA8, PA9, PA10, PA11, PA12 and PA14 were deposited pursuant to, and in satisfaction of, the requirements of the Budapest Treaty on the International Recognition of the Deposit of Microorganisms for the Purposes of Patent Procedure (the "Budapest treaty") with the American Type Culture Collection (ATCC), 10801 University Boulevard, Manassas, Va. 20110-2209 on Dec. 2, 1998 under the following Accession Nos.: ATCC Accession No. HB-12605 (PA8), ATCC Accession No. HB-12606 (PA9), ATCC Accession No. 12607 (PA10), ATCC Accession No. HB-12608 (P11), ATCC Accession No. HB-12609 (PA12), and ATCC Accession No. HB-12610 (PA14).

In a further embodiment of the present invention, the monoclonal antibody is PA14 produced by the hybridoma cell line designated PA14 (ATCC Accession No. HB-12610), or an antibody that competes with monoclonal antibody PA14's binding to the CCR5 receptor. In a still further embodiment, the monoclonal antibody is an antibody that binds to the same epitope as that to which monoclonal antibody PA14 binds. When binding to the same epitope occurs, competitive inhibition results.

In another embodiment, the monoclonal antibody is selected from the group consisting of PA14 produced by the hybridoma designated PA14 (ATCC Accession No. HB-12610), PA8 produced by the hybridoma designated PA8 (ATCC Accession No. HB-12605), PA9 produced by the hybridoma designated PA9 (ATCC Accession No. HB-12606), PA10 produced by the hybridoma designated PA10 (ATCC Accession No. HB-12607), PA11 produced by the hybridoma designated PA11 (ATCC Accession No. HB-12608), PA12 produced by the hybridoma designated PA12 (ATCC Accession No. HB-12609), and 2D7 (Wu et al., 1997). In a further embodiment, the monoclonal antibody is PA14.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody.

U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site-directed mutagenesis is used to graft the CDRs onto the framework.

Other approaches for humanizing an antibody are described in U.S. Pat. Nos. 5,585,089 and 5,693,761, and PCT International Publication No. WO 90/07861, which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody. The above methods are merely illustrative of some of the methods that one skilled in the art could employ to make humanized antibodies.

Methods for making fully human antibodies are also well known to one skilled in the art. For example, fully human monoclonal antibodies can be prepared by immunizing animals transgenic for large portions of human immunoglobulin heavy and light chain loci. See, e.g., U.S. Pat. Nos. 5,591,669, 5,545,806, 5,545,807, 6,150,584, and references cited therein, the contents of which are incorporated herein by reference. These transgenic animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these animals (e.g., XenoMouse® (Abgenix), HuMAb-Mouse® (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Nucleic acids encoding heavy and light chains of the humanized PRO 140 antibody have been deposited with the ATCC. Specifically, the plasmids designated pVK-HuPRO140, pVg4-HuPRO140 (mut B+D+I) and pVg4-HuPRO140 HG2, respectively, were deposited pursuant to, and in satisfaction of, the requirements of the Budapest Treaty with the ATCC, Manassas, Va., U.S.A. 20108, on Feb. 22, 2002, under ATCC Accession Nos. PTA 4097, PTA 4099 and PTA 4098, respectively.

In a preferred embodiment of the instant methods, the monoclonal antibody is the humanized antibody designated PRO 140 or an antibody that competes with PRO 140's binding to the CCR5 receptor, wherein PRO 140 comprises (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099). In a further embodiment, the monoclonal antibody is a humanized or human antibody that binds to the same epitope as that to which antibody PRO 140 binds. In another embodiment, the monoclonal antibody is the humanized antibody designated PRO 140. In a further embodiment, the monoclonal antibody is the human antibody designated CCR5mAb004 (Roschke et al., 2004; HGS Press Release, 2004; 2005).

In one embodiment of the methods described herein, the portion of the antibody comprises a light chain of the antibody. In another embodiment, the portion of the antibody comprises a heavy chain of the antibody. In a further embodiment, the portion of the antibody comprises an Fab portion of the antibody. In a still further embodiment, the portion of the antibody comprises an F(ab')$_2$ portion of the antibody. In an additional embodiment, the portion of the antibody comprises an Fd portion of the antibody. In another embodiment, the portion of the antibody comprises an Fv portion of the antibody. In a further embodiment, the portion of the antibody comprises a variable domain of the antibody. In a still further embodiment, the portion of the antibody comprises one or more CDR domains of the antibody. In yet another embodiment, the portion of the antibody comprises six CDR domains of the antibody.

In one embodiment of the instant methods, the antibody is administered to the subject a plurality of times and each administration of the antibody delivers from 0.01 mg per kg body weight to 50 mg per kg body weight of the antibody to the subject. In another embodiment, each administration of the antibody delivers from 0.05 mg per kg body weight to 25 mg per kg body weight of the antibody to the subject. In a further embodiment, each administration of the antibody delivers from 0.1 mg per kg body weight to 10 mg per kg body weight of the antibody to the subject. In a still further embodiment, each administration of the antibody delivers from 0.5 mg per kg body weight to 5 mg per kg body weight of the antibody to the subject. In another embodiment, each administration of the antibody delivers from 1 mg per kg body weight to 3 mg per kg body weight of the antibody to the subject. In a preferred embodiment, each administration of the antibody delivers about 2 mg per kg body weight of the antibody to the subject.

In one embodiment, the antibody is administered a plurality of times, and a first administration of the antibody is separated from the subsequent administration of the antibody by an interval of less than one week. In another embodiment, the first administration of the antibody is separated from the subsequent administration of the antibody by an interval of at least one week. In a further embodiment, the first administration of the antibody is separated from the subsequent administration of the antibody by an interval of one week. In another embodiment, the first administration of the antibody is separated from the subsequent administration of the antibody by an interval of two to four weeks. In a preferred embodiment, the first administration of the antibody is separated from the subsequent administration of the antibody by an interval of two weeks. In a further embodiment, the first administration of the antibody is separated from the subsequent administration of the antibody by an interval of four weeks. In yet another embodiment, the antibody is administered a plurality of times, and a first administration of the antibody is separated from the subsequent administration of the antibody by an interval of at least one month.

In a further embodiment, the antibody is administered to the subject via intravenous infusion. In a preferred embodiment, the antibody is administered to the subject via subcutaneous injection. In another embodiment, the antibody is administered to the subject via intramuscular injection.

In one embodiment of the instant methods, the non-antibody CCR5 receptor antagonist is a small organic molecule. In another embodiment, the CCR5 receptor antagonist is selected from the group consisting of SCH-D, UK-427,857, TAK-779, TAK-652, GW873140 and RANTES. In a further embodiment, the CCR5 receptor antagonist is an agent that competes with SCH-D's binding to the CCR5 receptor. In a still further embodiment, the CCR5 receptor antagonist is an agent that competes with UK-427,857's binding to the CCR5 receptor. In another embodiment, the CCR5 receptor antagonist is an agent that competes with TAK-779's binding to the CCR5 receptor. In yet another embodiment, the CCR5 receptor antagonist is an agent that competes with TAK-652's binding to the CCR5 receptor. In a further embodiment, the CCR5 receptor antagonist is an agent that competes with GW873140's binding to the CCR5 receptor.

In an additional embodiment of the methods described herein, the CCR5 receptor antagonist is administered a plurality of times and each administration of the CCR5 receptor antagonist delivers from 0.5 mg to 2,500 mg of the antagonist to the subject. In another embodiment, each administration of the CCR5 receptor antagonist delivers from 5 mg to 1,250 mg of the antagonist to the subject. In yet another embodiment, each administration of the CCR5 receptor antagonist delivers from 5 mg to 15 mg of the antagonist to the subject. In a further embodiment, each administration of the CCR5 receptor antagonist delivers from 50 mg to 1,250 mg of the antagonist to the subject. In a still further embodiment, each administration of the CCR5 receptor antagonist delivers from 200 mg to 800 mg of the antagonist to the subject. In another embodiment, each administration of the CCR5 receptor antagonist delivers from 300 mg to 600 mg of the antagonist.

Because of their rapid clearance, small-molecule CCR5 receptor antagonists require at least daily or twice-daily dosing in order to maintain selective pressure on the virus. Table 3 summarizes the dosing regimens employed with various small-molecule CCR5 antagonists currently undergoing clinical trials. In one embodiment of the present methods, the CCR5 receptor antagonist is administered orally to the subject at least once per day. In another embodiment, the CCR5 receptor antagonist is administered orally to the subject once or twice per day. In a further embodiment, the CCR5 receptor antagonist is administered orally three or fewer times per day.

TABLE 3

Dosing regimens of small-molecule CCR5 receptor antagonists undergoing clinical trials

| Compound | Dosage$^a$ | Clinical Trial |
| --- | --- | --- |
| SCH-D | 5-15 mg daily | Phase II |
| UK-427,857 | 300 mg daily or twice daily | Phase II and III |
| GW873140 | 50-1200 mg once daily, or 200-800 mg daily or twice daily | Phase II |

Dosages are indicated for the CCR5 antagonists at www.clinicaltrials.gov web site sponsored by the National Institute of Allergy and Infectious Diseases (NIAID). Dosage information for GW873140 was obtained from Demarest et al. (2004).

Additionally, one embodiment of the instant methods further comprises administering to the subject at least one anti-HIV-1, anti-retroviral agent. Since the approval of the nucleoside-analog reverse transcriptase inhibitor (NRTI) AZT (zidovudine) in 1987, the HIV-1 armamentarium has grown to at least 21 drugs and prodrugs representing 4 treatment classes: eight NRTIs, three non-nucleoside reverse transcriptase inhibitors (NNRTIs), nine protease inhibitors (PIs), and one fusion inhibitor (H) (see Table 4). In another embodiment, the anti-retroviral agent is a nonnucleoside reverse transcriptase inhibitor (NNRTI), a nucleoside reverse transcriptase inhibitor (NRTI), a protease inhibitor (PI), a fusion inhibitor, or any combination thereof. In further embodiments, the at least one anti-retroviral agent is one of the agents listed in Table 4 or any combination of these agents. Various anti-retroviral agents are marketed in combinations (see Table 5 for such combinations and dosing regimens) for more efficacious therapy. In embodiments of the present methods, anti-retroviral agents are administered to the subject in amounts shown in Table 5. In a preferred embodiment, the anti-retroviral agent is a NNRTI or a PI.

In another embodiment of the instant invention, the subject is treatment-naïve, i.e., the subject has not previously undergone treatment with any anti-HIV-1, anti-retroviral agents. In a preferred embodiment, the subject is treatment-experienced, i.e., the subject has undergone, and/or is undergoing, treatment with one or more anti-HIV-1, anti-retroviral agents, such as one or more agents listed in Table 4. In a preferred embodiment, the instant methods are used in a program of combination therapy for treating HIV-1 infection, wherein an anti-CCR5 mAb and a non-antibody CCR5 antagonist are administered in combination with one or more anti-retroviral agents to a subject in need of such treatment.

TABLE 4

Approved HIV-1 inhibitors

| Inhibitor | Manufacturer |
|---|---|
| Nucleoside Reverse Transcriptase Inhibitors (NRTIs) | |
| Retrovir ® (AZT) | GlaxoSmithKline |
| Epivir ® (3TC) | GlaxoSmithKline |

TABLE 4-continued

Approved HIV-1 inhibitors

| Inhibitor | Manufacturer |
|---|---|
| Emtriva ® (emtricitabine) | Gilead Sciences |
| Hivid ® (ddC) | Hoffmann-La Roche |
| Videx ® (ddI) | Bristol-Myers Squibb |
| Viread ® (tenofovir DF) | Gilead Sciences |
| Zerit ® (d4T) | Bristol-Myers Squibb |
| Ziagen ® (abacavir) | GlaxoSmithKline |
| Non-nucleoside Reverse Transcriptase Inhibitors (NNRTIs) | |
| Rescriptor ® (delavirdine) | Pfizer |
| Sustiva ® (efavirenz) | Bristol-Myers Squibb |
| Viramune ® (nevirapine) | Boehringer Ingelheim |
| Protease Inhibitors (PIs) | |
| Agenerase ® (amprenavir) | GlaxoSmithKline/Vertex |
| Aptivus ® (tipranavir)[a] | Boehringer Ingelheim |
| Crixivan ® (indinavir) | Merck & Co. |
| Invirase ® (saquinavir) | Hoffmann-La Roche |
| Lexiva ® (fosamprenavir) | GlaxoSmithKline/Vertex |
| Lopinavir[b] | Abbott Laboratories |
| Norvir ® (ritonavir) | Abbott Laboratories |
| Reyataz ® (atazanavir) | Bristol-Myers Squibb |
| Viracept ® (nelfinavir) | Pfizer |
| Fusion Inhibitors (Fis) | |
| Fuzeon ® (T-20) | Trimeris/Hoffmann-La Roche |

[a]To be co-administered with ritonavir to boost therapeutic levels of Aptivus ®.
[b]Sold only in combination with ritonavir under the trade name Kaletra ®.

TABLE 5

Dosing regimens of marketed HIV-1 antiviral agents

| Generic Name | Brand/other Name | Dosage* | Formulation | Manufacturer | Approval date |
|---|---|---|---|---|---|
| Nonnucleoside Reverse Transcriptase Inhibitors (NNRTIs) | | | | | |
| Delavirdine | Rescriptor, DLV | 400 (4 × 100 or 2 × 200) mg tid | Tablet | Pfizer | Apr. 04, 1997 |
| Efavirenz | Sustiva, EFV | 600 mg qd | Tablet | Bristol-Myers Squibb | Sep. 17, 1998 |
| Nevirapine | Viramune, NVP | 200 mg bid (qd first 2 wks of Rx) | Tablet | Boehringer Ingelheim | Jun. 21, 1996 |
| Nucleoside Reverse Transcriptase Inhibitors (NRTIs) | | | | | |
| Abacavir | Ziagen, ABC | 600 (2 × 300) mg qd or 300 mg bid | Tablet | GlaxoSmithKline | Dec. 17, 1998 |
| Abacavir, Lamivudine | Epzicom | **600/300 mg qd | Tablet | GlaxoSmithKline | Aug. 02, 2004 |
| Abacavir, Lamivudine, Zidovudine | Trizivir | **300/150/300 mg qd | Tablet | GlaxoSmithKline | Nov. 14, 2000 |
| Didanosine | Videx, ddI, Videx EC | 400 mg qd (≥60 kg) or 250 mg qd (<60 kg) | Delayed-release Capsule | Bristol-Myers Squibb | Oct. 09, 1991; Oct. 31, 2000 (EC) |
| Emtricitabine | Emtriva, FTC, Coviracil | 200 mg qd | Capsule | Gilead Sciences | Jul. 02, 2003 |
| Emtricitabine Tenofovir DF | Truvada | **200/300 mg qd | Tablet | Gilead Sciences | Aug. 02, 2004 |
| Lamivudine | Epivir, 3TC | 300 mg qd or 150 mg bid | Tablet | GlaxoSmithKline | Nov. 17, 1995 |
| Lamivudine, Zidovudine | Combivir | **150/300 mg bid | Tablet | GlaxoSmithKline | Sep. 27, 1997 |
| Stavudine | Zerit, d4T | 40 mg bid (≥60 kg) or 30 mg bid (<60 kg) | Capsule | Bristol-Myers Squibb | Jun. 24, 1994 |
| Tenofovir DF | Viread, TDF | 300 mg qd | Tablet | Gilead Sciences | Oct. 26, 2001 |
| Zalcitabine | Hivid, ddC | 0.750 mg tid | Tablet | Hoffmann-La Roche | Jun. 19, 1992 |
| Zidovudine | Retrovir, AZT, ZDV | 300 mg bid or 200 (2 × 100) mg tid | Tablet or Capsule | GlaxoSmithKline | Mar. 19, 1987 |
| Protease Inhibitors (PIs) | | | | | |
| Amprenavir | Agenerase, APV | 1200 (8 × 150) mg bid | Capsule | GSK, Vertex | Apr. 15, 1999 |
| Atazanavir | Reyataz, ATV | Naïve pts: 400 (2 × 200) mg qd Salvage: 300 (2 × 150) mg qd w/ritonavir 100 mg qd | Capsule | Bristol-Myers Squibb | Jun. 20, 2003 |
| Fosamprenavir | Lexiva, FPV | 1400 (2 × 700) mg bid | Tablet | GSK, Vertex | Oct. 20, 2003 |
| Indinavir | Crixivan, IDV | 800 (2 × 400) mg tid | Capsule | Merck | Mar. 13, 1996 |
| Lopinavir, Ritonavir | Kaletra, LPV/r | **400/100 (3 × 133.3/33.3) mg bid | Capsule | Abbott Laboratories | Sep. 15, 2000 |

TABLE 5-continued

Dosing regimens of marketed HIV-1 antiviral agents

| Generic Name | Brand/other Name | Dosage* | Formulation | Manufacturer | Approval date |
|---|---|---|---|---|---|
| Nelfinavir | Viracept, NFV | 1250 mg (5 × 250 or 2 × 625) bid or 750 mg (3 × 250) tid | Tablet | Agouron | Mar. 14, 1997 |
| Ritonavir | Norvir, RTV | 600 (6 × 100) mg bid | Capsule | Abbott Laboratories | Mar. 01, 1996 |
| Saquinavir | Fortovase, SQV | 1200 (6 × 200) mg tid | Capsule | Hoffmann-La Roche | Nov. 07, 1997 |
|  | Invirase | 1000 (5 × 200) mg bid w/ritonavir 100 mg bid | Capsule | Hoffmann-La Roche | Dec. 06, 1995 |
| Tipranivir | Aptivus | 1000 (2 × 250) mg bid w/ ritonavir (2 × 100) mg bid | Capsule | Boehringer Ingelheim | Jun. 23, 2005 |
| Fusion Inhibitors (FIs) | | | | | |
| Enfuvirtide | Fuzeon, T-20 | sc: 90 mg (1 ml) bid | Reconstituted solution | Hoffmann-La Roche, Trimeris | Mar. 13, 2003 |

*Adult doses unadjusted for combination therapies; Route of administration: po unless otherwise indicated
**Combination therapies administered in a single formulation
Legend:
qd = once daily
bid = twice daily
tid = three times daily
po = oral administration
sc = subcutaneous administration This invention further provides a composition of matter comprising (a) a monoclonal antibody (e.g., PRO 140) which (i) binds to a CCR5 receptor and (ii) inhibits fusion of HIV-1 to CCR5+CD4+ cells, and (b) a non-antibody CCR5 receptor antagonist (e.g., any of SCH-D, UK-427,857, TAK-779, TAK-652, GW873140 and RANTES). The composition can further comprise a pharmaceutically acceptable carrier. This invention also provides a method for determining whether a monoclonal antibody (e.g., PRO 140) which (i) binds to a CCR5 receptor and (ii) inhibits fusion of HIV-1 to CCR5+CD4+ cells, behaves synergistically with a non-antibody CCR5 receptor antagonist with respect to inhibiting fusion of HIV-1 to CCR5+CD4+ cells, comprising determining the presence or absence of such synergy according to the experimental methods detailed below. Finally, this invention provides a kit for performing the instant methods comprising, in separate compartments and preferably in readily administrable forms, (a) a monoclonal antibody (e.g., PRO 140) which (i) binds to a CCR5 receptor and (ii) inhibits fusion of HIV-1 to CCR5+CD4+ cells, and (b) a non-antibody CCR5 receptor antagonist (e.g., any of SCH-D, UK-427,857, TAK-779, TAK-652, GW873140 and RANTES). The antibody and antagonist are each preferably admixed with a pharmaceutically acceptable carrier.

The following Experimental Details are set forth to aid in an understanding of the subject matter of this disclosure, but are not intended to, and should not be construed to, limit in any way the claims which follow thereafter.

Experimental Details

Part I

Materials and Methods
Compounds and mAbs

PRO 140 was prepared by expression in Sp2/0 cells using Hybridoma serum-free medium supplemented with 2 mM L-glutamine (Invitrogen, Carlsbad, Calif.). Bulk mAb was clarified using a 5.0 μm Depth filter (Sartorius, Goettingen, Germany) followed by passage over a 0.2 μm sterilizing grade filter (Sartorius). The mAb was purified by passage first over an affinity column (MabSelect Protein A column, Amersham, Piscataway, N.J.) and then by ion exchange chromatography (SP Sepharose Cation Exchange resin, Amersham). PRO 140 was nanofiltered using a Viresolve™ 10 Opticap NFP capsule (Millipore, Billerica, Mass.) followed by a 0.2 μm filter and concentrated/diafiltered over disposable TFF cartridges (Millipore). The mAb was then polished over a hydroxyapatite column (Bio-Rad, Hercules, Calif.), concentrated to 10 mg/ml in phosphate-buffered saline and stored at −70° C. or colder prior to use.

RANTES was purchased from R&D Systems (Minneapolis, Minn.). The anti-CCR5 mAb 2D7 was purchased from BD Biosciences (Cat. #555993), and the anti-CCR5 mAb CTC5 was purchased from R&D Systems (Cat. #FAB1802P).

RET Assay

The HIV-1 RET assay has been described in detail previously (Litwin et al., 1996). Briefly, fluorescein octadecyl ester (F18; Molecular Probes, Eugene, Oreg.; 5 mg/ml in ethanol), was diluted 1:800 in DMEM labeling medium (DMEM; Invitrogen, Carlsbad, Calif.) with 10% fetal bovine serum (FBS; HyClone, Logan, Utah) and adjusted to an $A_{506}$ of 0.34±10%. Octadecyl rhodamine B chloride (R18; Molecular Probes; 10 mg/ml in ethanol) was diluted 1:2050 in labeling medium and adjusted to an $A_{565}$ of 0.52±10%. Both dyes were further diluted 2-fold by addition to cells in T75-cm² flasks. HeLa-Env$_{JRFL}$ and CEM NKR-CCR5 cells were incubated overnight in F18- and R18-containing culture medium, respectively. The following day, medium from HeLa-Env$_{JRFL}$ cells was removed and 10 ml of 0.5 mM EDTA was added and incubated at 37° C. for 5 min. EDTA was removed and the flask was returned to the incubator for another 5 min followed by striking of the flask to dislodge cells. Ten ml of PBS− with 15% FBS were added to the flask and the contents were transferred to a 50-ml conical centrifuge tube. Suspension CEM NKR-CCR5 cells were added directly to a separate 50-ml conical centrifuge tube. Both cell lines were centrifuged at 300×g for 5 min. The supernatant was discarded and cells were resuspended in 10 ml of PBS−/15% FBS. The centrifugation/wash step was repeated twice, after which the cells were counted and concentrations adjusted to 1.5×10⁶ cells/ml. Ten μl of each cell type (15,000 cells) were seeded into wells of a 384-well plate. Inhibitor compounds were added immediately thereafter to bring the final well volume to 40 μl, and the plates were incubated for 4 h at 37° C. Compounds were tested individually and in combination at a fixed molar ratio or mass ratio over a range of serial dilutions. The plates were then read on a fluorescence plate reader (Victor², Perkin Elmer, Boston, Mass.) using the excitation/emission filter combinations shown in Table 6.

TABLE 6

Excitation/emission filter combinations for RET assay

| Scan No. | Excitation wavelength | Emission wavelength |
|---|---|---|
| 1 | 450 nm/50 nm | 530 nm/25 nm |
| 2 | 530 nm/25 nm | 590 nm/35 nm |
| 3 | 450 nm/50 nm | 590 nm/35 nm |

The "% RET" was calculated according to the following formula after subtraction of background (blank) readings:

$$\% \text{ RET} = 100 \times [(A_3 - (A_1 \times F_{spill}) - (A_2 \times R_{spill}))/A_2]$$

Where:
$F_{spill}$=HeLa cells alone, Scan 3/Scan 1;
$R_{spill}$=CEM cells alone, Scan 3/Scan 2;
$A_1$=Scan 1 value for HeLa and CEM cells in combination;
$A_2$=Scan 2 value for HeLa and CEM cells in combination; and
$A_3$=Scan 3 value for HeLa and CEM cells in combination.

The "% Inhibition" was calculated according to the following formula:

$$\% \text{ Inhibition} = 100 \times [(\text{Max \% RET} - \% \text{ RET for sample well})/(\text{Max \% RET} - \text{Min \% RET})]$$

Where:
Max % RET=average of % RET values for HeLa and CEM cell combination without added inhibitor; and
Min % RET=average of % RET values for HeLa and CEM cell combination in presence of 500 ng/ml of Leu-3a mAb (an antibody that targets CD4 and fully blocks fusion in the RET assay at this concentration).

Fifty percent inhibition ($IC_{50}$) values were determined by fitting the inhibition data with a non-linear, four-parameter, variable slope equation (GraphPad Prism, 4.02; GraphPad Software, San Diego, Calif.). Upper and lower inhibition values were constrained to 100% and 0%, respectively for curve fitting.

Preparation of PBMCs

Replication of authentic HIV-1 is measured in activated peripheral blood mononuclear cells (PBMCs) using the monocyte/macrophage-tropic HIV-1 clone, JRFL (HIV-$1_{JRFL}$), for these studies.

PBMCs are isolated from 4 separate donors (Leukopacks) by centrifugation on a Ficoll gradient. CD8 cells are depleted using RosetteSep CD8 Depletion Cocktail (#15663, StemCell Research, Vancouver, BC). Cells are diluted to $4 \times 10^6$/ml and added in equal parts to three T175-cm² flasks and then stimulated by addition of one of the following media: IL-2 Medium [RPMI 1640 (#10-040-CV, Cellgro, Herndon, Va.), 10% FBS (#35-010-CV), 2 mM L-Glutamine (#25-005-CI), 100 U/ml IL-2 (Sigma, St. Louis, Mo.)]; PHA 5 Medium: [IL-2 Medium with 5 ug/ml Phytohemagglutinin PHA-P (PHA) (#L8754, Sigma, St. Louis, Mo.), filtered]; or PHA 0.5 Medium: [IL-2 Medium with 0.5 ug/ml PHA, filtered]. Each flask receives a total of 50-150 ml of medium. Flasks are incubated for 3 days at 37° C. followed by pooling of the contents prior to use in the infection assay.

Virus Titration

Serial dilutions of virus are tested in quadruplicate on activated PBMCs ($1.4 \times 10^5$ PBMC/well). Titration Medium [IL-2 Medium with 100 IU/ml penicillin/streptomycin (#30-002-CI, Cellgro)] is utilized for virus titrations. Fifty μl of diluted virus is added to 100 μl of PBMCs in flat bottom, tissue-culture treated 96-well plates (VWR#29442-054, Corning, Corning, N.Y.) and the plates are incubated at 37° C. in a humidified, 5% $CO_2$ incubator. After 7 days, 50 μl are removed from each well an for virus levels by p24 antigen ELISA (Perkin Elmer, Boston, Mass.). Virus titer is determined by the method of Reed and Muench (Table 11, see below).

Neutralization Assay

Stimulated PBMCs are seeded into wells of 96-well flat bottom plates at a density of $1.4 \times 10^5$ cells/well. Virus is diluted to 2,000 $TCID_{50}$/ml and mixed with serial 0.5 $\log_{10}$ dilutions of compound for 1 h at 37° C. prior to addition to the cell plates. The final amount of virus added per well is 100 $TCID_{50}$. The final DMSO concentration in the assay is always 0.5% whenever small molecule inhibitors are being tested. Plates are incubated at 37° C. for 5 days, at which time an aliquot of supernatant is removed for p24 antigen ELISA. If control wells (virus without inhibitor) exhibit low p24 antigen levels then the plates are brought back to full volume with Titration medium and incubated for an additional 24 h.

Data Analysis

Neutralization activity is displayed by plotting the percent inhibition of p24 antigen production (after background values are subtracted from all datapoints) versus $\log_{10}$ drug concentration. The percent inhibition is derived as follows [1−(p24 levels in the presence of drug/p24 levels in the absence of drug)]×100. $IC_{50}$ values are determined by fitting the inhibition data with a non-linear, four-parameter, variable slope equation (GraphPad Prism, ver. 4.02; GraphPad Software, San Diego, Calif.). Upper and lower inhibition values are constrained to 100% and 0%, respectively for curve fitting.

Phase 1a Clinical Study

Individuals were treated in sequential, dose-rising cohorts of 5 subjects (4 active and 1 placebo) each and evaluated for up to 120 days post-treatment. A population of healthy, i.e., HIV-1 uninfected, male volunteers with no abnormal findings on physical exam, medical history and ECG, aged 19-50, was administered a single intravenous infusion of PRO 140 (0.1, 0.5, 2.0 and 5.0 mg per kg body weight). Safety assessments consisted of monitoring the following: vital signs (blood pressure, pulse, temperature, etc; hematology (hemoglobin, hematocrit, leukocytes, platelets, etc.); serum chemistries (AST/ALT, alkaline phosphatase, BUN, creatinine, etc.); urinalysis (pH, specific gravity, protein, glucose, leukocytes, etc.); and ECGs (12-lead).

Measurement of Coating of CCR5 Cells by PRO 140

Whole blood specimens were combined separately with the indicated phycoerythrin-labeled anti-CCR5 antibodies or with appropriate isotype-control antibodies. Erythrocytes were lysed and leukocytes were stabilized using the ImmunoPrep Reagent System (Beckman Coulter), and the cells were analyzed on a TQ Prep™ flow cytometry workstation (Beckman Coulter). Data were expressed as the percent of CCR5 cells relative to all cells gated in the analysis. CTC5 is an anti-CCR5 antibody that does not compete with PRO 140. 2D7 is an anti-CCR5 antibody that does compete with PRO 140.

Measurement of Serum Concentrations of PRO 140

Sera were diluted as appropriate and combined with L1.2-CCR5 cells, which are mouse pre-B lymphoma cells engineered to stably express human CCR5. In order to generate a standard curve, PRO 140 standard was tested in parallel at concentrations ranging from 0.062 to 4.0 mg/ml in 10% normal human serum (NHS). 10% NHS containing no PRO 140 was analyzed as a negative control. Following incubation with test samples, cells were washed and combined with a FITC-labeled sheep antibody against human IgG4 (The Binding Site Limited, Cat. #AF009). Cells were washed again and analyzed by flow cytometry. The concentration of PRO 140 was determined by comparing the median fluorescence intensity (MFI) of the test sample with MFI values of the standard curve.

Determination of Plasma RANTES Concentration

The assay employed the Quantikine™ Human RANTES Immunoassay Kit (R&D Systems, Minneapolis, Minn.). Briefly, platelet-poor plasma was collected in CTAD/EDTA tubes and stored at −20° C. Test samples and RANTES standard were added to microtiter plates that were pre-coated with a mouse monoclonal antibody to RANTES. Following incubation, plates were washed and contacted with an anti-RANTES polyclonal antibody conjugated to horseradish peroxidase (HRP). Plates were washed again prior to addition of tetramethlybenzidine substrate for colorimetric detection. The Lower Limit of Quantification of the assay was 415 pg RANTES/ml plasma.

Results and Discussion

PRO 140 is a humanized IgG4,κ anti-CCR5 mAb being developed for HIV-1 therapy. This antibody has been shown to broadly and potently inhibit CCR5-mediated fusion of HIV-1 to target cells in vitro. PRO 140 is also highly active in a therapeutic hu-PBL-SCID mouse model, and preliminary data are now available from a Phase 1a clinical study in healthy human subjects.

In Vitro Antiviral Activity of PRO 140

Murine and humanized PRO 140 were tested against four primary R5 HIV-1 isolates as described in the Methods. FIG. 1 shows that PRO 140 has potent antiviral activity in vitro, neutralizing a variety of primary R5 strains with an IC90 of 3-4 µg/ml. PRO 140 exhibited similar antiviral activity to the murine mAb, PA14, from which PRO 140 is derived.

Preliminary Data from Phase 1a Clinical Study

The primary objective of the Phase 1a study was to evaluate the safety and tolerability of PRO 140 given as a single dose in a rising dose cohort regimen in healthy male subjects. The secondary objectives were (1) to gain information about the pharmacokinetics of intravenously administered PRO 140, and (2) to gain information on the effects of PRO 140 on blood levels of CCR5+ cells and chemokines.

Pharmacokinetics of PRO 140

Healthy male volunteers were treated with a single intravenous infusion of PRO 140 at dose levels of 0.1, 0.5, 2.0 and 5.0 mg/kg. PRO 140 and placebo were generally well tolerated with no significant changes in ECGs and no dose-limiting toxicity.

Figure 7:
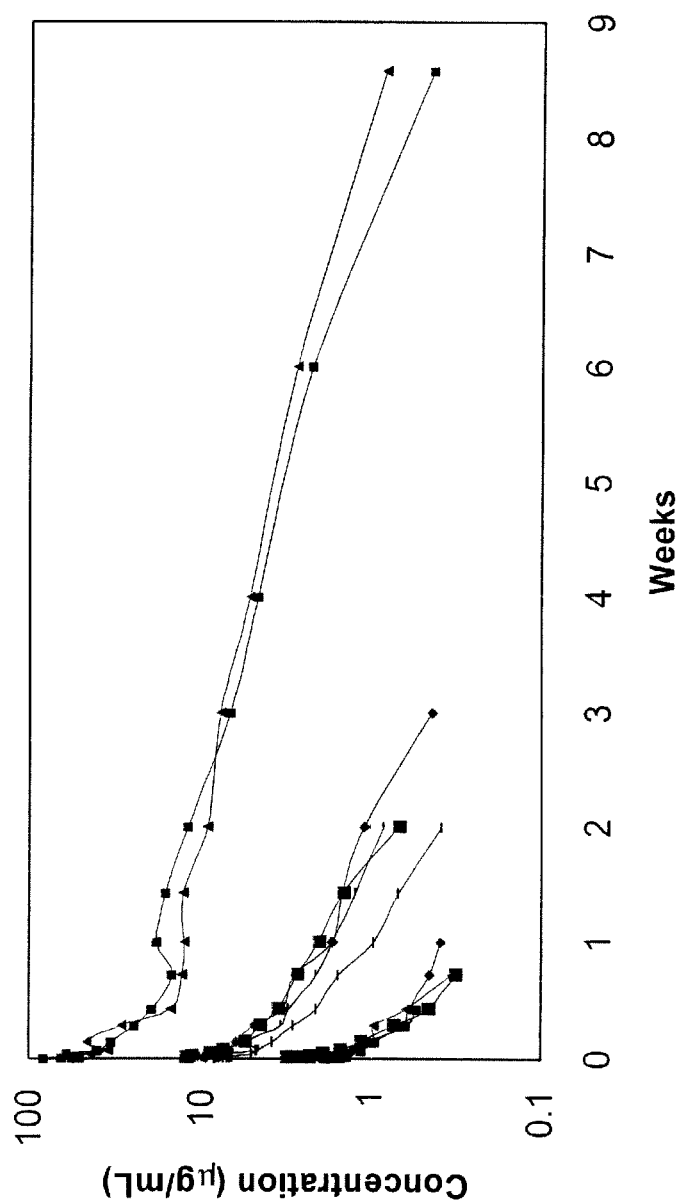

Serum was collected post-treatment, cryopreserved, and analyzed for PRO 140 levels. Peak serum concentrations ranged to 3 mg/ml at 0.1 mg/kg and 12 mg/ml at 0.5 mg/kg. Serum concentrations remained detectable (>400 ng/ml for up to 5 days at 0.1 mg/kg, 21 days at 0.5 mg/kg, and for over 60 days following a single 2 mg/kg injection (FIG. 7). Serum concentrations of PRO 140 increased proportionally with dose level, and the clearance rate was similar to that of other humanized mAbs. Pharmacokinetic (PK) metrics were determined using WinNonLin (PharSight Corporation, Mountain View, Calif.) using a noncompartmental model, and the terminal serum half-life of PRO 140 was determined to be 10-12 days. As expected, no subject developed antibodies to the humanized PRO 140.

Coating and Non-Depletion of CCR5 Lymphocytes by PRO 140

Healthy male volunteers (n=4) were treated with a single intravenous infusion of PRO 140 at a dose level of 2 mg/kg. For up to 60 days post-treatment, at the times indicated in FIG. 6, blood was collected and analyzed for CCR5 lymphocyte levels.

Figure 6:
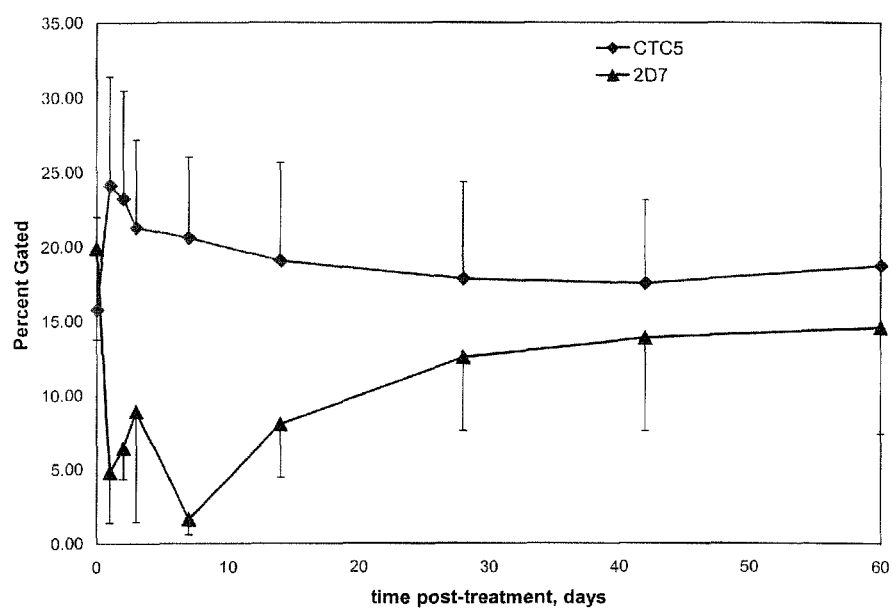

Following treatment with PRO 140, there was no decrease in the overall number of CCR5 lymphocytes at measured by CTC5 binding; however, the binding of antibody 2D7 was significantly decreased (FIG. 6). Background binding of isotype control antibodies was unchanged. Since the binding of CTC5 is not decreased by the presence of PRO 140, the CTC5-PE values are a measure of the total number of circulating CCR5 lymphocytes. Since 2D7 competes with PRO 140, the 2D7-PE values reflect the number of CCR5 lymphocytes that are not coated with PRO 140.

Figure 13:
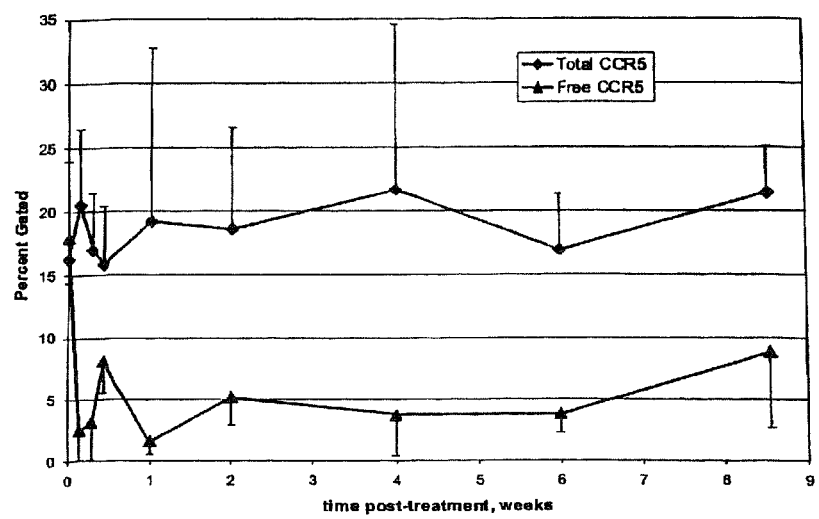
Figure 14:
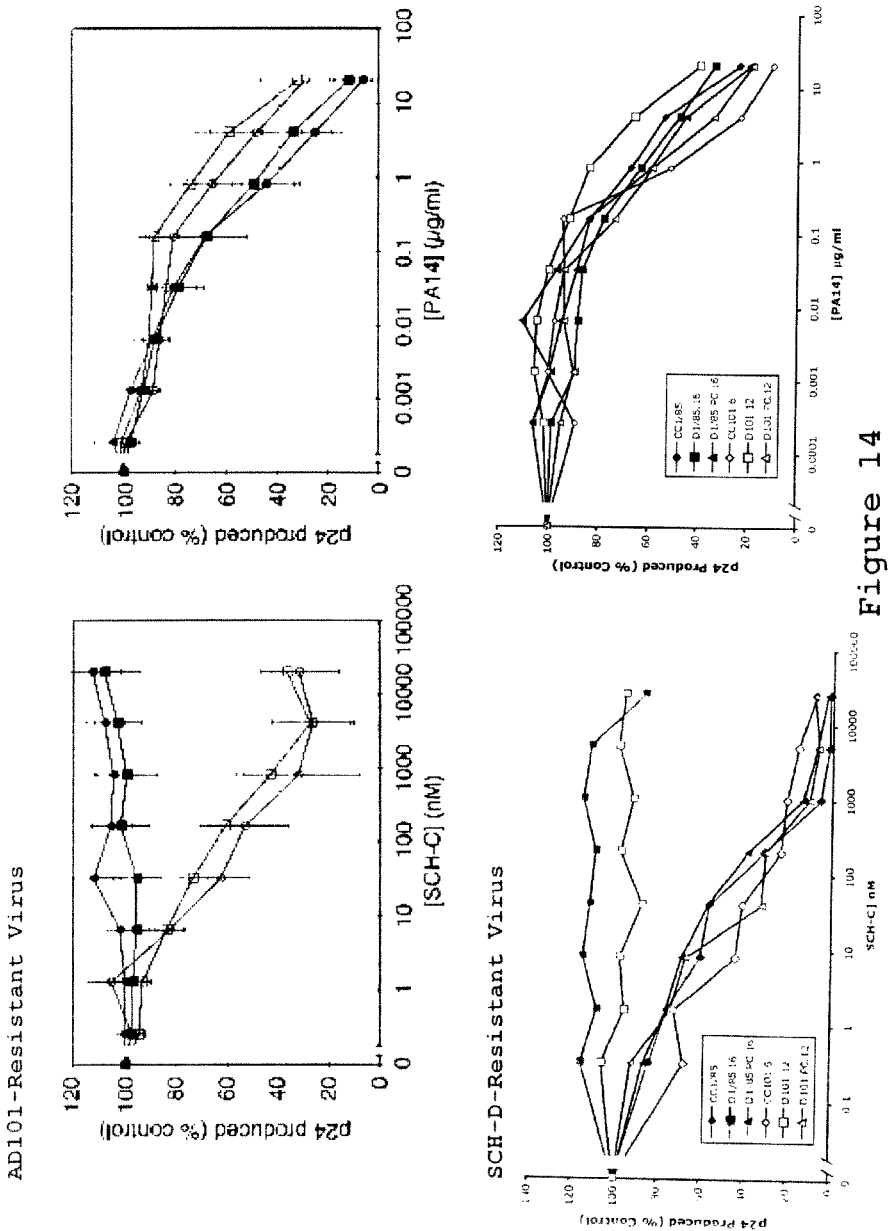

The data indicate that a single 2 mg/kg dose of PRO 140 effectively coats CCR5 lymphocytes without cellular depletion for two weeks, and cells remain partially coated for >4 weeks. In addition, CCR5 coating was more prolonged in patients treated with 5 mg/kg PRO 140. The data indicate that a single 5 mg/kg dose of PRO 140 effectively coats CCR5 lymphocytes without cellular depletion and the cells remain partially coated for >60 days (FIG. 13). Since CCR5 coating is the mechanism whereby PRO 140 inhibits HIV, viral loads in HIV-infected individuals could be expected to decrease in a similar temporal manner.

Effect of PRO 140 on Plasma Chemokine Levels

Figure 8:
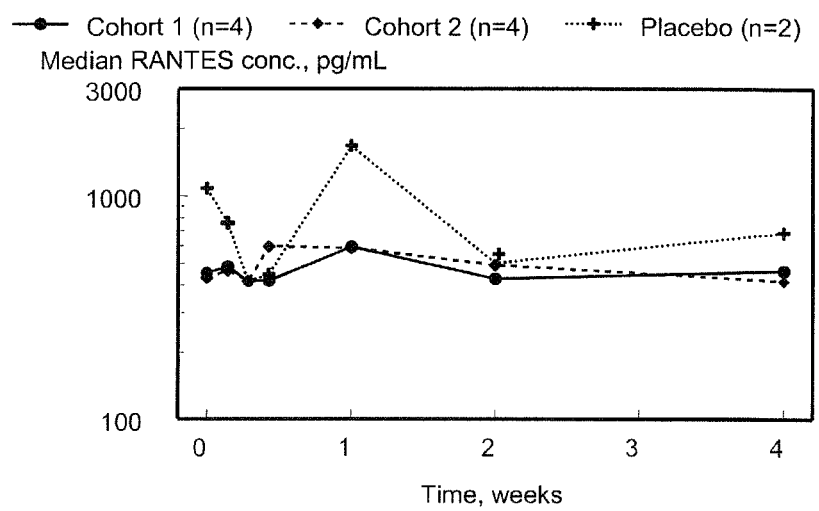
Figure 9:
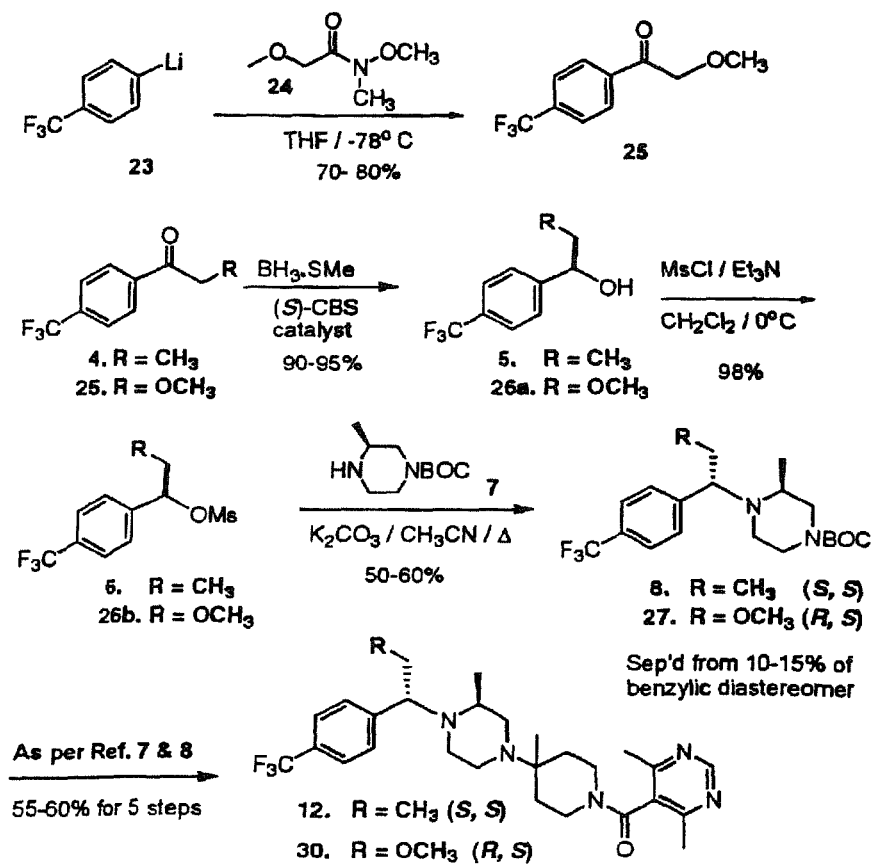
Figure 10:
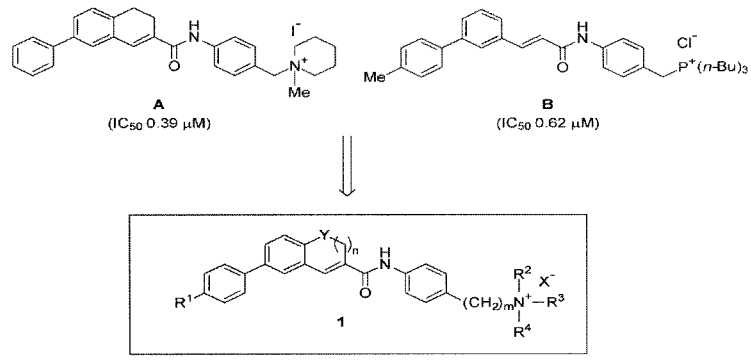
Figure 10:
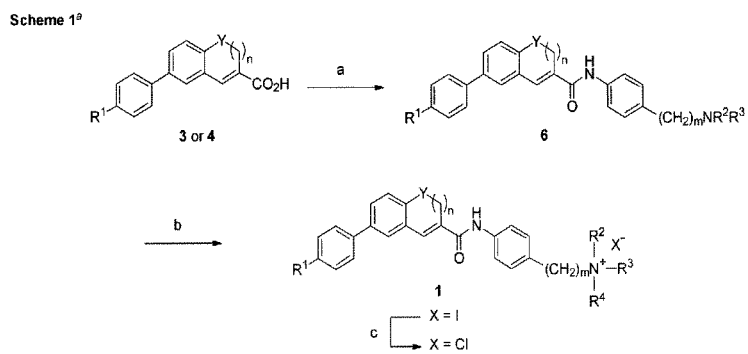
Figure 10:
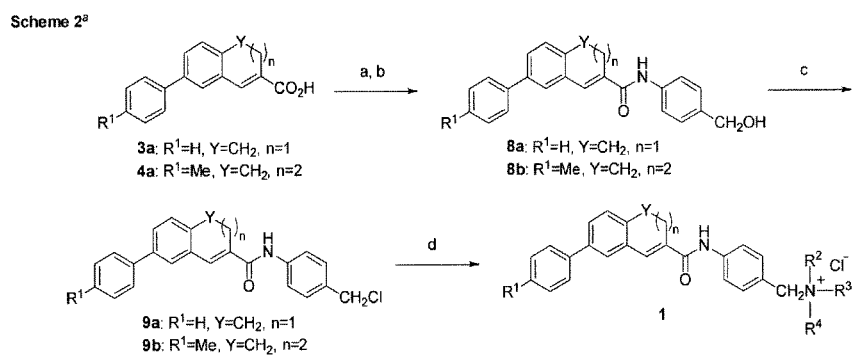
Figure 11:
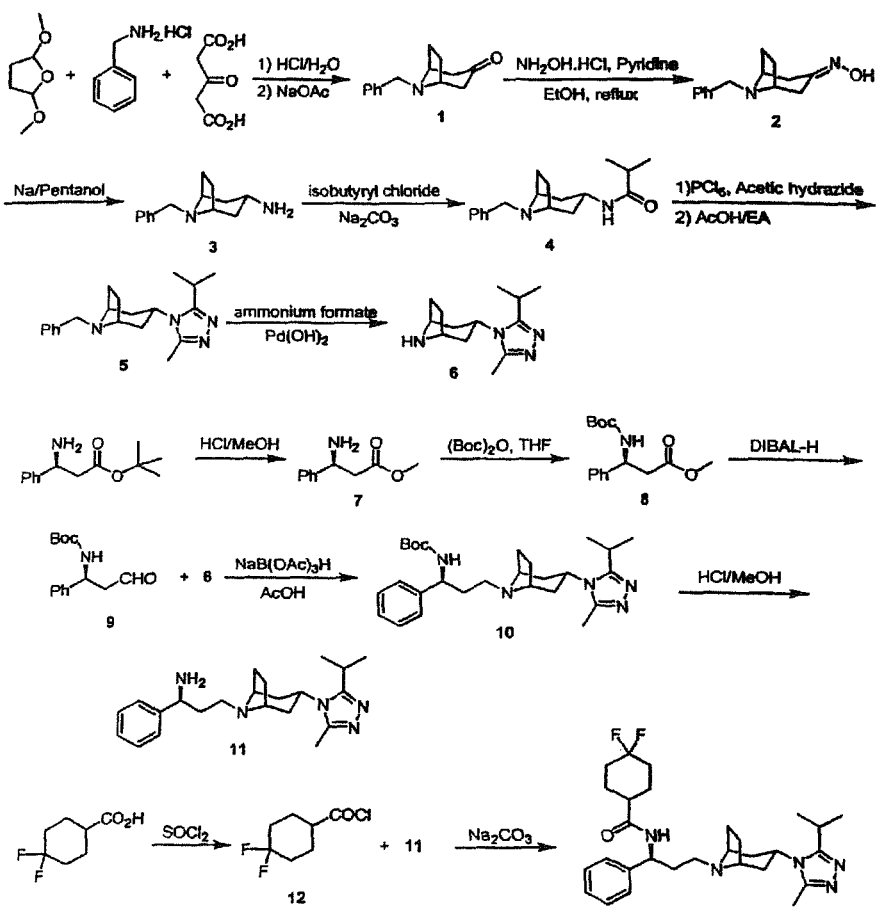
Figure 12:
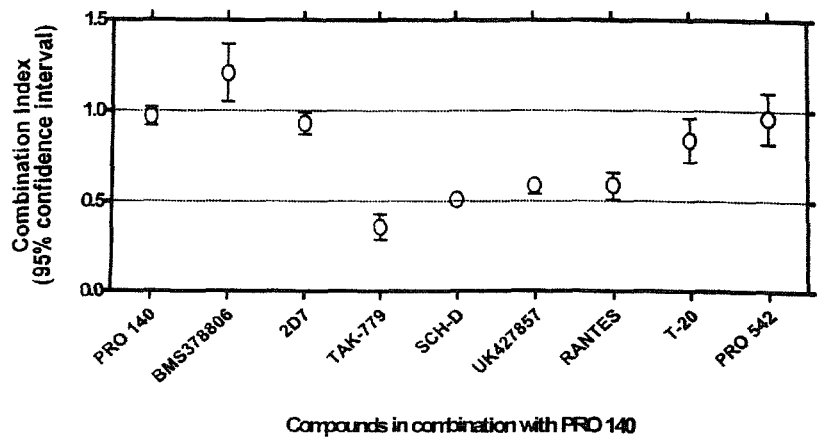

Healthy male volunteers were treated with a single intravenous infusion 010.1 mg/kg PRO 140 (Cohort 1), 0.5 mg/kg PRO 140 (Cohort 2) or matched placebo. Plasma was collected post-treatment at the indicated times, cryopreserved and analyzed for levels of RANTES, a CC-chemokine that serves as a natural ligand for CCR5. RANTES levels were measured by ELISA in platelet-depleted plasma pre-dose and up to 28 days post-dose. As shown in FIG. 8, there was no significant change in RANTES levels following PRO 140 treatment ($P>0.14$ all times). These data are consistent with in vitro findings that PRO 140 does not antagonize CCR5 function. The findings suggest that PRO 140 does not have untoward effects on CCR5-mediated immune function in treated patients.

The results described herein indicate that in addition to PRO 140 broadly and potently inhibiting CCR5-mediated HIV-1 entry without CCR5 antagonism or other immunologic side effects in preclinical testing, this has demonstrated favorable tolerability, PK and immunologic profiles in preliminary results from an ongoing Phase 1a study in healthy volunteers. Thus, in many respects, PRO 140 offers a novel and attractive product profile for anti-HIV-1 therapy.

Moreover, the activities of anti-CCR5 mAbs are fundamentally distinct from, but complementary to, those of small-molecule CCR5 antagonists (see Table 2) which are also currently undergoing human clinical trials. PRO 140 has recently been shown to work synergistically with non-antibody CCR5 antagonists in inhibiting CCR5-mediated HIV-1 fusion to target cells. Accordingly, combination therapy comprising administration of anti-CCR5 mAbs and non-antibody CCR5 antagonists may offer powerfully effective, new approaches to preventing and treating HIV-1 infection.

Part II

Example 1

Combination Testing of Pro 140 and HIV-1 Entry Inhibitors in the Fluorescence RET Assay Materials and Methods Compounds and mAbs PRO 140 was prepared by expression in Sp2/0 cells using Hybridoma serum-free medium supplemented with 2 mM L-glutamine (Invitrogen, Carlsbad, Calif.). Bulk mAb was clarified using a 5.0 μm Depth filter (Sartorius, Goettingen, Germany) followed by passage over a 0.2 μm sterilizing grade filter (Sartorius). The mAb was purified by passage first over an affinity column (MabSelect Protein A column, Amersham, Piscataway, N.J.) and then by ion exchange chromatography (SP Sepharose Cation Exchange resin, Amersham). PRO 140 was nanofiltered using a Viresolve™ 10 Opticap NFP capsule (Millipore, Billerica, Mass.) followed by a 0.2 μm filter and concentrated/diafiltered over disposable TFF cartridges (Millipore). The mAb was then polished over a hydroxyapatite column (Bio-Rad, Hercules, Calif.), concentrated to 10 mg/ml in phosphate-buffered saline and stored at −70° C. or colder prior to use.

TAK-779 has the following structure:

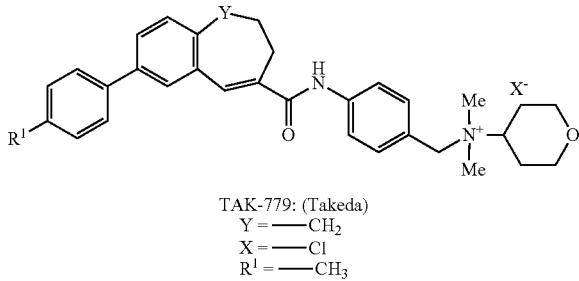

TAK-779: (Takeda)
Y = ——CH$_2$
X = ——Cl
R$^1$ = ——CH$_3$

Figure 2:
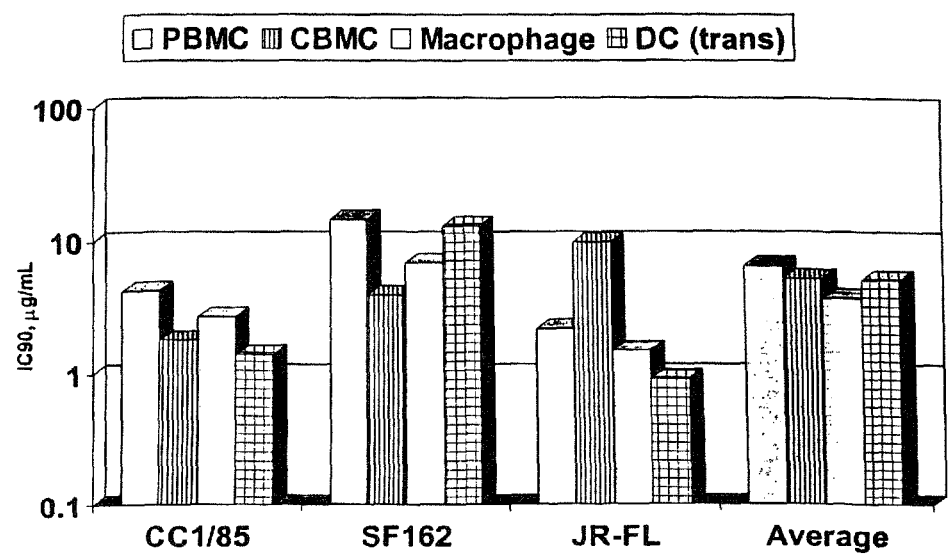

TAK-779 was synthesized according to the procedure described in Shiraishi et al. (2000) and set forth in FIG. 2.

TAK-652 has the following structure:

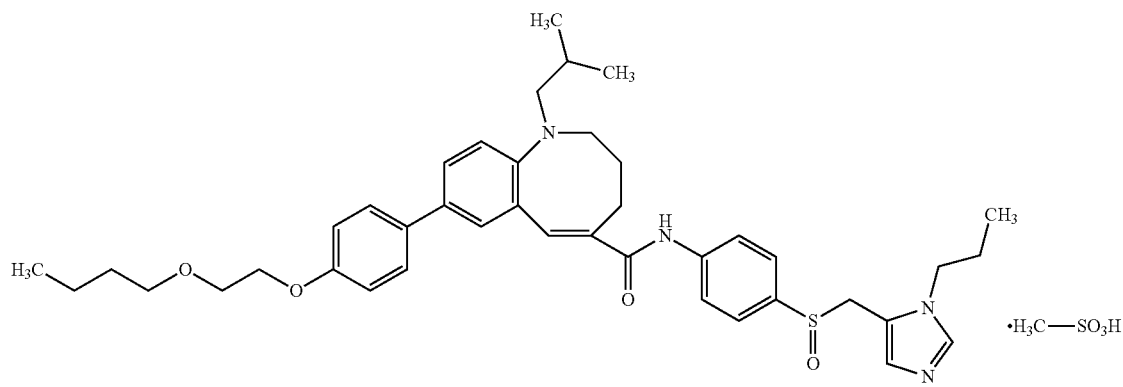

SCH-D (Schering Plough; Tagat et al., 2004), TAK-779 (Takeda Pharmaceuticals; Shiraishi et al., 2000), UK-427, 857 (Pfizer; Wood and Armour, 2005), and BMS378806 (Bristol-Myers Squibb; Lin et al., 2003) were prepared by commercial sources.

SCH-D has the following structure:

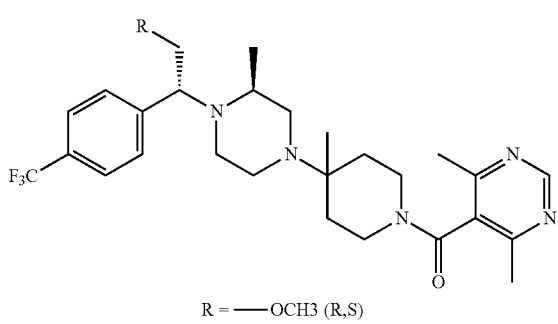

R = ——OCH3 (R,S)

SCH-D (also designated SCH-417690): 1-[(4(4,6-dimethyl-5-pyrimidinyl)carbonyl]-4-[4-[2-methoxy-1(R)-4-(trifluoromethyl)phenyl]ethyl-3(S)-methyl-1-piperazinyl]-4-methylpiperidine (Schering-Plough)

SCH-D was synthesized according to the procedure described in Tagat et al. (2004) and set forth in FIG. 1.

UK-427,857 has the following structure:

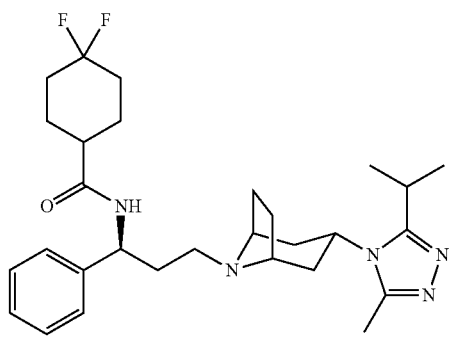

UK-427,857: (Pfizer)

Figure 3:
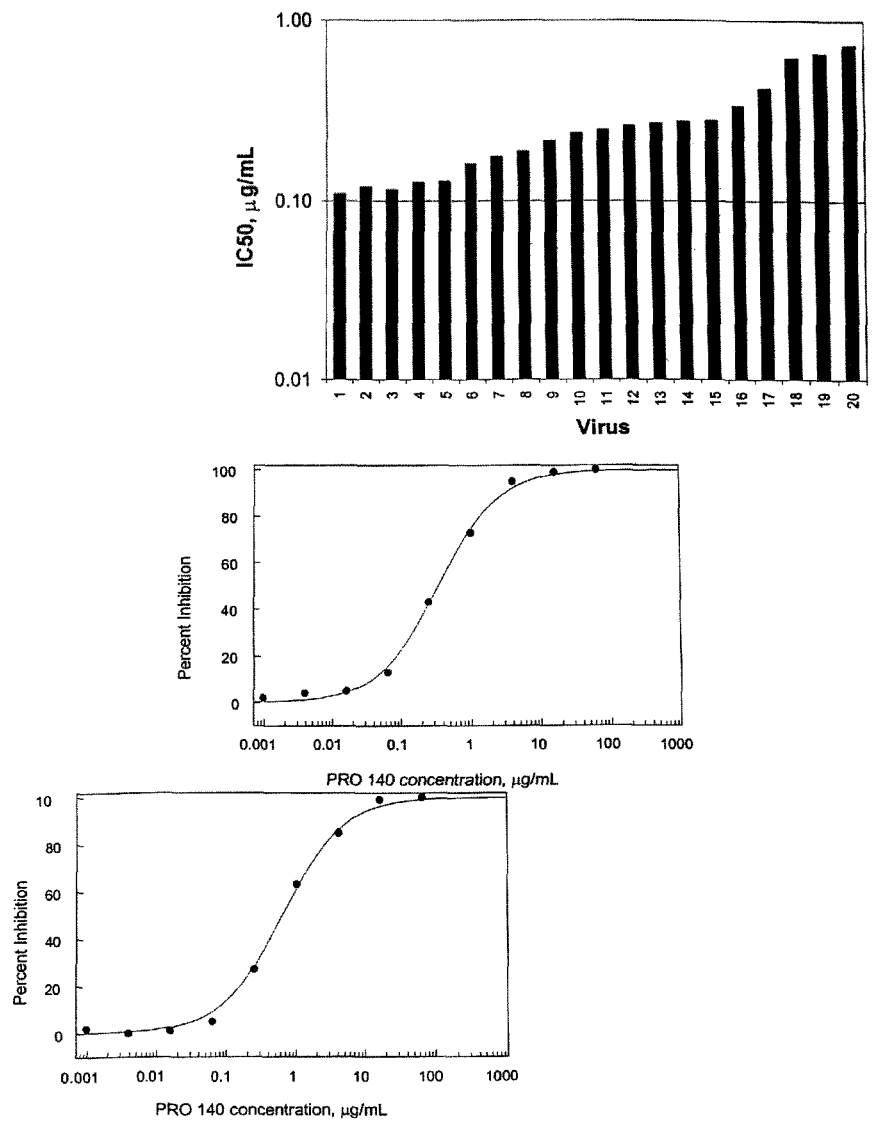

UK-427,857 was synthesized according to the procedure described in PCT International Publication No. WO 01/90106 and set forth in FIG. 3.

BMS378806 has the following structure:

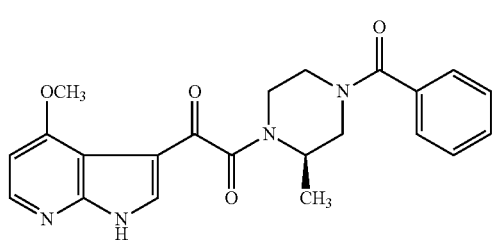 [SMILES: COc1ccnc2[nH]cc(C(=O)C(=O)N3CCN(C(=O)c4ccccc4)C[C@H]3C)c12]

BMS378806: (R)—N-(benzoyl)-3-methyl-N'-[(4-methoxy-7-azaindol-3-yl)-oxoacetyl]-piperazine (Bristol-Myers Squibb)

It was synthesized according to the procedure described in U.S. Pat. No. 6,476,034 (compound 17a).

Nevirapine (Boehringer Ingelheim; Merluzzi et al., 1990) and atazanavir (Bristol-Myers Squibb; Robinson et al., 2000) were purchased from commercial sources. PRO 542 was expressed in Chinese hamster ovary cells and purified as described previously (Allaway et al., 1995). T-20 (Fuzeon®) was synthesized by solid-phase fluroenylmethoxycarbonyl chemistry, was purified by reverse-phase chromatography and was analyzed for purity and size by HPLC and mass spectroscopy as described previously (Nagashima et al., 2001). AZT was purchased from Sigma Chemicals (St. Louis, Mo.). RANTES was purchased from R&D Systems (Minneapolis, Minn.). The anti-CCR5 mAb 2D7 was purchased from Pharmingen (San Diego, Calif.), and the anti-CD4 mAb Leu-3A was purchased from Becton Dickinson (Franklin Lakes, N.J.).

For testing, small molecule compounds were solubilized in dimethylsulfoxide (DMSO) to 10 mM and then diluted in DMSO to 200× the final concentration to be utilized in the antiviral assay. Serial dilutions of small molecules were conducted in DMSO. Subsequent dilutions were conducted in medium to achieve a final DMSO concentration in the assay of 0.5%. Peptides and mAbs were diluted in PBS in the absence of DMSO. Typically, inhibitor concentrations in the RET assay included eleven 3-fold dilutions ranging from 200 nM to 3.0 pM.

Cell Preparation

HeLa cells were engineered to express HIV-1 gp120/gp41 from the macrophage-tropic primary isolate JRFL as described (HeLa-Env$_{JRFL}$: Litwin et al., 1996). Briefly, the HIV-1$_{LAI}$ Env gene was excised from the plasmid pMA243 (Dragic et al., 1992) and the HIV-1$_{JRFL}$ Env gene was inserted. The HIV-1$_{JRFL}$ Env gene was amplified from the plasmid pUCFL112-1 (Koyanagi et al., 1987). The resulting plasmid, designated JR-FL-pMA243, was sequenced by standard methods and transfected into HeLa cells using lipofectin (Gibco BRL/Invitrogen, Carlsbad, Calif.). HeLa-Env$_{JRFL}$ transfectants were selected in methotrexate (Sigma, St. Louis, Mo.) and cloned twice by limiting dilution. The transduced human T cell leukemia line CEM NKR-CCR5 cells were obtained from the NIH AIDS Research and Reference Program (Cat. No. 458).

RET Assay

The HIV-1 RET assay has been described in detail previously (Litwin et al., 1996). Briefly, fluorescein octadecyl ester (F18; Molecular Probes, Eugene, Oreg.; 5 mg/ml in ethanol), was diluted 1:800 in DMEM labeling medium (DMEM; Invitrogen, Carlsbad, Calif.) with 10% fetal bovine serum (FBS; HyClone, Logan, Utah) and adjusted to an $A_{506}$ of 0.34±10%. Octadecyl rhodamine B chloride (R18; Molecular Probes; 10 mg/ml in ethanol) was diluted 1:2050 in labeling medium and adjusted to an $A_{565}$ of 0.52±10%. Both dyes were further diluted 2-fold by addition to cells in T75-cm² flasks. HeLa-Env$_{JRFL}$ and CEM NKR-CCR5 cells were incubated overnight in F18- and R18-containing culture medium, respectively. The following day, medium from HeLa-Env$_{JRFL}$ cells was removed and 10 ml of 0.5 mM EDTA was added and incubated at 37° C. for 5 min. EDTA was removed and the flask was returned to the incubator for another 5 min followed by striking of the flask to dislodge cells. Ten ml of PBS– with 15% FBS were added to the flask and the contents were transferred to a 50-ml conical centrifuge tube. Suspension CEM NKR-CCR5 cells were added directly to a separate 50-ml conical centrifuge tube. Both cell lines were centrifuged at 300×g for 5 min. The supernatant was discarded and cells were resuspended in 10 ml of PBS–/15% FBS. The centrifugation/wash step was repeated twice, after which the cells were counted and concentrations adjusted to 1.5×10⁶ cells/ml. Ten μl of each cell type (15,000 cells) were seeded into wells of a 384-well plate. Inhibitor compounds were added immediately thereafter to bring the final well volume to 40 μl, and the plates were incubated for 4 h at 37° C. Compounds were tested individually and in combination at a fixed molar ratio or mass ratio over a range of serial dilutions. The plates were then read on a fluorescence plate reader (Victor², Perkin Elmer, Boston, Mass.) using the excitation/emission filter combinations shown in Table 6.

TABLE 6

Excitation/emission filter combinations for RET assay

| Scan No. | Excitation wavelength | Emission wavelength |
|---|---|---|
| 1 | 450 nm/50 nm | 530 nm/25 nm |
| 2 | 530 nm/25 nm | 590 nm/35 nm |
| 3 | 450 nm/50 nm | 590 nm/35 nm |

The "% RET" was calculated according to the following formula after subtraction of background (blank) readings:

$$\% \text{RET} = 100 \times [(A_3 - (A_1 - F_{spill}) - (A_2 \times R_{spill}))/A2]$$

Where:
$F_{spill}$=HeLa cells alone, Scan 3/Scan 1;
$R_{spill}$=CEM cells alone, Scan 3/Scan 2;
$A_1$=Scan 1 value for HeLa and CEM cells in combination;
$A_2$=Scan 2 value for HeLa and CEM cells in combination; and
$A_3$=Scan 3 value for HeLa and CEM cells in combination.

The "% Inhibition" was calculated according to the following formula:

$$\% \text{Inhibition} = 100 \times [(\text{Max } \% \text{ RET} - \% \text{ RET for sample well})/(\text{Max } \% \text{ RET} - \text{Min } \% \text{ RET})]$$

Where:
Max % RET=average of % RET values for HeLa and CEM cell combination without added inhibitor; and
Min % RET=average of % RET values for HeLa and CEM cell combination in presence of 500 ng/ml of Leu-3a mAb (an antibody that targets CD4 and fully blocks fusion in the RET assay at this concentration).

Fifty percent inhibition ($IC_{50}$) values were determined by fitting the inhibition data with a non-linear, four-parameter, variable slope equation (GraphPad Prism, ver. 4.02; GraphPad Software, San Diego, Calif.). Upper and lower inhibition values were constrained to 100% and 0%, respectively for curve fitting.

Synergy Determinations

Cooperative inhibition effects of drug combinations were determined by the method of Chou and Talalay (1984). $IC_{50}$ values were generated for all combinations as described above. Combination Index (CI) and Dose Reduction (DR) values were calculated according to the following formulas:

$$CI = \left(\frac{IC_{50}Dcomb1}{IC_{50}Dsolo1}\right) + \left(\frac{IC_{50}Dcomb2}{IC_{50}Dsolo2}\right) + \alpha\left(\frac{(IC_{50}Dcomb1)(IC_{50}Dcomb2)}{(IC_{50}Dsolo1)(IC_{50}Dsolo2)}\right)$$

$$\text{DR (for compound 1)} = (IC_{50}Dsolo1/IC_{50}Dcomb1)$$

$$\text{DR (for compound 2)} = (IC_{50}Dsolo2/IC_{50}Dcomb2)$$

Where:
"$IC_{50}$ Dcomb1"=$IC_{50}$ of drug 1 in combination with drug 2;

"IC$_{50}$ Dsolo1"=IC$_{50}$ of drug 1 when tested alone;
"IC$_{50}$ Dcomb2"=IC$_{50}$ of drug 2 in combination with drug 1;
"IC$_{50}$ Dsolo2"=IC$_{50}$ of drug 2 when tested alone;
α=0 if the effects of the two drugs are mutually exclusive; and
α=1 if the effects of the two drugs are mutually nonexclusive Combinations with CI<1 are determined to be synergistic, whereas combinations with CI>1 are determined to be antagonistic. Additivity is reflected in combinations for which CI=1.

Ninety five percent Confidence Intervals were calculated in Microsoft Excel using the formula:

=Confidence(alpha,stdev,$n$)

Where:
alpha=0.05 (95% confidence);
stdev=standard deviation of dataset mean; and
n=number of replicates.

Results

Preparation of Small-Molecule Fusion Inhibitors

SCH-D, TAK-779, UK-427,857, and BMS378806 were prepared by commercial sources. The desired quantities and HPLC purity of the compounds were realized. Purity of the compounds was supported by results obtained from elemental analysis, and the identities of the products were confirmed by proton NMR (proton and carbon-13) and/or mass spectrum data.

Synergistic Interactions Revealed by RET Assay

Synergy experiments were conducted using the cell-cell RET fusion assay to assess initially the potential for cooperative interactions between PRO 140 and small-molecule and peptide-based inhibitors of CCR5, CD4, HIV-1 gp120 and HIV-1 gp41. The experiments were then extended to the CCR5-specific murine monoclonal antibody, 2D7 (Wu et al., 1997).

Experiments measuring inhibition of HIV-1 Env-mediated fusion were first conducted using combinations of PRO 140 with, respectively, PRO 140 itself, 3 small-molecule CCR5 antagonists (SCH-D, TAK-779, UK427857), the natural peptide ligand of CCR5 (RANTES), and an anti-CCR5 mAb (2D7), a peptide-based inhibitor of gp41 (T-20), a protein-based inhibitor of gp120 (PRO 542), a small-molecule inhibitor of gp120 (BMS378806), and an anti-CD4 mAb (Leu3A). Mass ratios of PRO 140 to other entry inhibitors ranged from 0.75 to 364. The results are shown in Table 7.

TABLE 7

Combination Index and Dose Reduction Values for inhibition of HIV-1 Env-mediated fusion with combinations of PRO 140 and entry inhibitors

| PRO 140 in combination with:[a] | No. of tests | Cpd mass ratios[b] | Inhibitor target | Mean CI[c] | Mean Dose Reduction (PRO 140) | Mean Dose Reduction (Cpd in combination) |
|---|---|---|---|---|---|---|
| | | | | | Cell-cell fusion assay | |
| PRO 140 | 9 | 1 | CCR5 | 0.97 ± 0.08 | 2.07 ± 0.18 | 2.07 ± 0.18 |
| TAK-779 | 8 | 282 | CCR5 | 0.36 ± 0.10 | 4.10 ± 2.03 | 15.86 ± 7.10 |
| SCH-D | 9 | 279 | CCR5 | 0.51 ± 0.05 | 4.21 ± 0.96 | 3.90 ± 0.71 |
| UK-427,857 | 3 | 292 | CCR5 | 0.59 ± 0.04 | 4.16 ± 0.41 | 2.98 ± 0.65 |
| RANTES | 4 | 19 | CCR5 | 0.59 ± 0.08 | 4.13 ± 0.99 | 3.24 ± 1.06 |
| 2D7 | 2 | 1 | CCR5 | 0.93 ± 0.04 | 1.87 ± 0.07 | 2.54 ± 0.13 |
| T-20 | 7 | 33 | gp41 | 0.84 ± 0.16 | 1.77 ± 0.40 | 7.47 ± 3.34 |
| PRO 542 | 6 | 0.75 | gp120 | 0.96 ± 0.17 | 1.59 ± 0.21 | 5.54 ± 1.49 |
| BMS-378806 | 7 | 364 | gp120 | 1.21 ± 0.21 | 1.64 ± 0.30 | 2.85 ± 0.76 |

[a]Compounds were tested at a 1:1 molar ratio.
[b]Mass of PRO 140/mass of other HIV-1 entry inhibitor tested in combination. Molecular weights of inhibitors are: PRO 140 ≈ 150,000 g/mole; SCH-D = 538 g/mole; TAK-779 = 531 g/mole (hydrochloride salt); UK-427,857 = 514 g/mole; RANTES ≈ 7,800 g/mole; 2D7 ≈ 150,000 g/mole; T-20 = 4,492 g/mole; PRO 542 ≈ 200,000 g/mole; BMS-378806 = 412 g/mole.
[c]Combination Index at IC$_{50}$ value. The mutually exclusive CI formula (α = 0) was utilized for PRO 140 in combination with molecules that bind CCR5, and the mutually non-exclusive formula (α = 1) was utilized for PRO 140 in combination with molecules that bind other targets (Chou and Rideout, 1991).

Two small-molecule CCR5 antagonists, SCH-D and TAK-779, were assayed in combination. PRO 542, a recombinant antibody-like fusion protein in which the heavy- and light-chain variable domains of human IgG2 have been replaced with the D1D2 domains of human CD4, was also tested in combination with the anti-CD4 mAb, Leu-3A. The results of these assays are shown in Table 8.

TABLE 8

Other drug combinations tested in the RET assay for cooperativity

| Drug 1 | Drug 2 | Molar ratios (Drug 1 to 2) | N | Mean CI ± stdev[a] | Mean DR (Drug 1) | Mean DR (Drug 2) |
|---|---|---|---|---|---|---|
| SCH-D | TAK-779 | 1:1 | 4[b] | 1.12 ± 0.32 | 1.48 ± 0.96 | 4.31 ± 1.82 |
| PRO 542 | Leu-3A | 22.9:1 | 2 | 16.9 ± 0.3 | 0.7 ± 0 | 0.16 ± 0 |

[a]CI values were calculated using the mutually exclusive formula for SCH-D vs. TAK-779 (i.e., where α = 0) and the mutually non-exclusive formula for PRO 542 vs. Leu-3A (i.e., where α = 1; see methods).
[b]One aberrant datapoint was culled from the calculation of Mean CI and Mean DRs.

Figure 4:
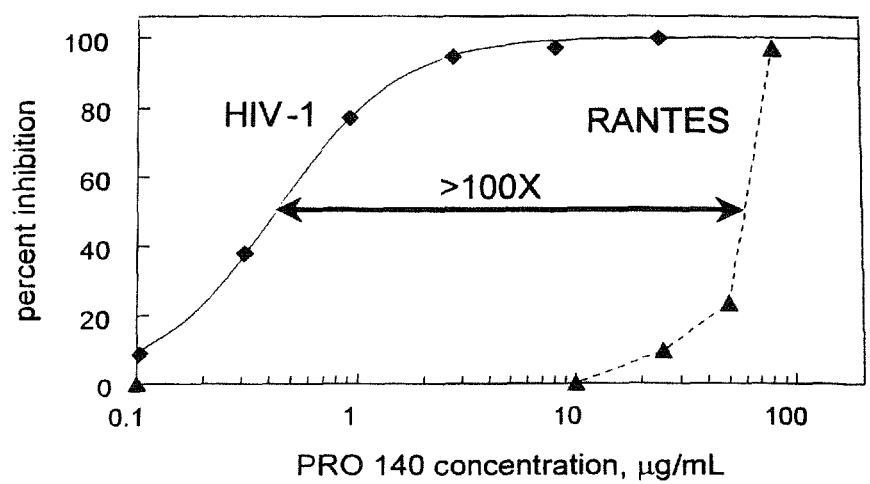
Figure 5:
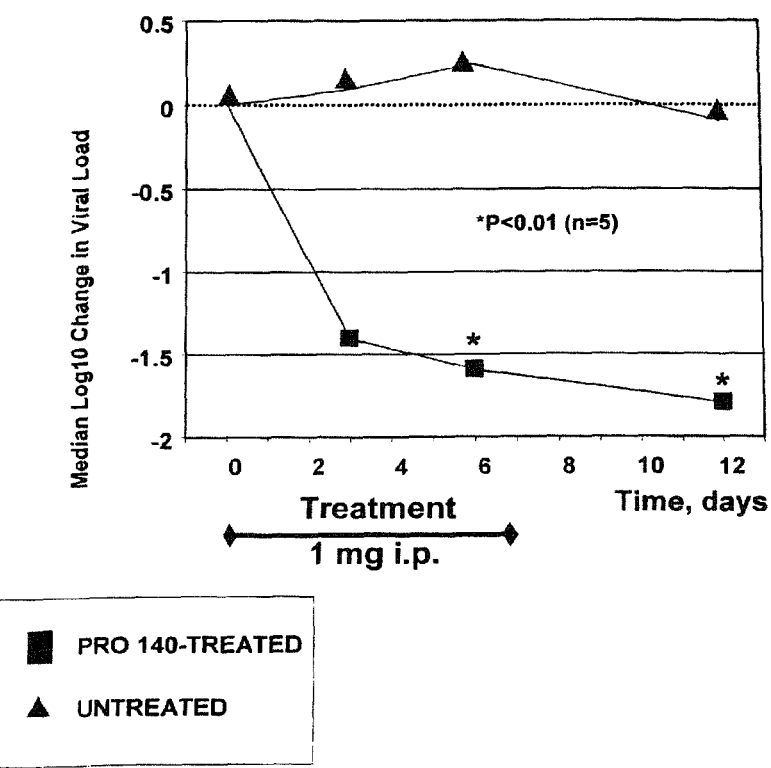

The effect of varying the relative amounts of compounds in the combinations on the level of cooperativity was also measured. Molar ratios of 5:1 and 1:5 PRO 140 were used. The results are tabulated in Table 9, and the mean CI values with 95% confidence intervals are plotted in FIG. 4 for the 1:1 molar ratio data. In addition to PRO 140, the inhibitory activity of mAb 2D7, a CCR5-specific murine antibody (Wu et al., 1997) was also tested in combination with the small-molecule CCR5 antagonists and with RANTES using the fluorescent RET assay. The results are shown in Table 10.

TABLE 9

Combination Index and Dose Reduction Values for inhibition of HIV-1 Env-mediated fusion with combinations of PRO 140 and entry inhibitors

| PRO 140 in combination with: | Ratio[a] | Cpd Mass Ratios[b] | Mean Combination Index[c] | Mean Dose Reduction (PRO 140) | Mean Dose Reduction (Cpd. in combination) |
|---|---|---|---|---|---|
| | | | | Cell-cell fusion assay | |
| PRO 140 | 5:1 | 5 | 1.15 ± 0.09 | 1.05 ± 0.08 | 5.26 ± 0.41 |
| PRO 140 | 1:5 | 0.2 | 1.09 ± 0.08 | 5.54 ± 0.38 | 1.10 ± 0.08 |
| TAK-779 | 5:1 | 1410 | 0.57 ± 0.07 | 1.89 ± 0.14 | 33.59 ± 18.85 |
| TAK-779 | 1:5 | 56.4 | 0.52 ± 0.20 | 5.58 ± 0.52 | 3.78 ± 1.95 |
| SCH-D | 5:1 | 1395 | 0.66 ± 0.10 | 1.92 ± 0.40 | 8.44 ± 1.27 |
| SCH-D | 1:5 | 55.8 | 0.69 ± 0.05 | 9.95 ± 2.03 | 1.73 ± 0.19 |
| UK-427,857 | 5:1 | 1460 | 0.66 ± 0.11 | 2.00 ± 0.35 | 7.25 ± 2.19 |
| UK-427,857 | 1:5 | 58.4 | 0.73 ± 0.05 | 11.31 ± 2.14 | 1.58 ± 0.17 |
| RANTES | 5:1 | 95 | 0.84 ± 0.14 | 1.63 ± 0.43 | 5.39 ± 1.13 |
| RANTES | 1:5 | 3.8 | 0.66 ± 0.06 | 13.64 ± 4.75 | 1.75 ± 0.28 |
| T-20 | 5:1 | 165 | 1.10 ± 0.12 | 0.98 ± 0.11 | 31.85 ± 10.19 |
| T-20 | 1:5 | 6.6 | 0.76 ± 0.27 | 2.93 ± 0.68 | 3.85 ± 1.50 |
| PRO 542 | 5:1 | 3.75 | 1.13 ± 0.10 | 1.01 ± 0.07 | 15.73 ± 4.15 |
| PRO 542 | 1:5 | 0.15 | 1.18 ± 0.17 | 2.83 ± 0.50 | 1.71 ± 0.29 |
| BMS-378806 | 5:1 | 1820 | 1.12 ± 0.10 | 1.14 ± 0.06 | 8.88 ± 4.16 |
| BMS-378806 | 1:5 | 72.8 | 1.55 ± 0.24 | 3.64 ± 0.73 | 1.07 ± 0.31 |

[a]Molar ratio of PRO 140 to other entry inhibitor tested in combination (n = 3 for all experimental results)
[b]Mass of PRO 140/mass of other HIV-1 entry inhibitor tested in combination. Molecular weights of inhibitors are: PRO 140 ≈ 150,000 g/mole; SCH-D = 538 g/mole; TAK-779 = 531 g/mole (hydrochloride salt); UK-427,857 = 514 g/mole; RANTES ≈ 7,800 g/mole; T-20 = 4,492 g/mole; PRO 542 ≈ 200,000 g/mole; BMS-378806 = 412 g/mole.
[c]Combination Index at $IC_{50}$ value. The mutually exclusive CI formula ($\alpha = 0$) was utilized for PRO 140 in combination with molecules that bind CCR5, and the mutually non-exclusive formula ($\alpha = 1$) was utilized for PRO 140 in combination with molecules that bind other targets (Chou and Rideout, 1991).

TABLE 10

Combination Index and Dose Reduction Values for inhibition of HIV-1 Env-mediated fusion with combinations of 2D7 and entry inhibitors

| 2D7 in combination with:[a] | Cpd Mass Ratios[c] | Inhibitor target | Mean Combination Index[b] | Mean Dose Reduction (2D7) | Mean Dose Reduction (Cpd in combination) |
|---|---|---|---|---|---|
| | | | | Cell-cell fusion assay | |
| TAK-779 | 282 | CCR5 | 0.15 ± 0.03 | 17.20 ± 3.23 | 11.95 ± 4.94 |
| SCH-D | 279 | CCR5 | 0.57 ± 0.10 | 3.25 ± 0.56 | 4.04 ± 0.78 |
| UK427857 | 292 | CCR5 | 0.58 ± 0.03 | 2.45 ± 0.12 | 5.73 ± 0.54 |
| RANTES | 19 | CCR5 | 0.62 ± 0.04 | 1.94 ± 0.08 | 10.18 ± 1.86 |
| PRO 140 | 1 | CCR5 | 0.93 ± 0.04 | 2.54 ± 0.13 | 1.87 ± 0.07 |

[a]Compounds were tested at a 1:1 molar ratio (all data are n = 3 except for 2D7 and PRO 140, where n = 2)
[b]Combination Index at $IC_{50}$ value. The mutually exclusive CI formula ($\alpha = 0$) was utilized for 2D7 in combination with molecules that bind CCR5 (Chou and Rideout, 1991).
[c]Mass of 2D7/mass of other HIV-1 entry inhibitor tested in combination. Molecular weights of inhibitors are: 2D7 ≈ 150,000 g/mole; SCH-D = 538 g/mole; TAK-779 = 531 g/mole (hydrochloride salt); UK-427,857 = 514 g/mole; RANTES ≈ 7,800 g/mole.

Example 2

Combination Testing of Pro 140 with Small Molecule, Peptide and Protein Inhibitors, and HIV-1 in the HIV-1 Pseudovirus Particle (HIV-1PP) Assay Materials and Methods
Preparation of HIV-1 Pseudoparticles HIV-1 pseudoparticles (HIV-1pp) are generated in 293T cells by transient coexpression of an HIV-1-based NL4/3luc+ env-plasmid and a construct encoding HIV-1$_{JRFL}$ Env. The NL4/3luc+env-plasmid was obtained from the NIH AIDS Research and Reference Reagent Program (Cat. No. 3418), and the HIV-1$_{JRFL}$ Env was inserted into the pcDNA3.1 vector (Invitrogen). Briefly, 293T cells are calcium phosphate transfected with a 1:1 ratio of NL4/3luc+env-reporter vector and Env expression vector in Hepes buffer (Profection Mammalian Transfection Kit, Promega). After 16 h the transfection medium is aspirated and fresh cell culture medium (DMEM with 10% FBS, glutamine and antibiotics) is added and the incubation is continued at 37° C. for an additional 24-32 h. Cell culture supernatants are collected 48 h post-transfection and centrifuged at 1,400 rpm for 10 min to pellet cell debris. The viral supernatant is brought to a final concentration of 5% sucrose and stored aliquoted at −80° C.

Cells

U87-CD4-CCR5 cells were obtained from the NIH AIDS Research and Reference Program (Cat. No. 4035). These cells are maintained in culture medium (DMEM with 10% FBS, antibiotics and glutamine) containing 0.3 mg/ml G418 and 0.5 mg/ml puromycin. Cells are grown in T175-cm$^2$ flasks at 37° C. and diluted 1:5 every 3-4 days. For assay plate preparation, cells are trypsinized and seeded into wells of 96-well tissue-culture treated flat bottom opaque polystyrene plates (Perkin Elmer, Boston, Mass.) at a density of 3×10$^3$ cells/well. Plates are incubated for no more than 4 h at 37° C. in a humidified 5% $CO_2$ incubator prior to their use in the HIV-1 pp susceptibility assay.

Compound Preparation

Fifty μl of diluted compound at 4× the desired final concentration are added per well. For compounds solubilized in DMSO, the 4× stock will contain 2% DMSO (such that the final DMSO concentration in the assay is always 0.5% for small molecules). Control wells receiving no compound are included on each plate. In addition, an AZT inhibition control is included in each assay. Compounds are tested individually and at a fixed mass or molar ratio over a broad range of concentrations.

Virus Addition

A vial of frozen, aliquoted HIV-1pp is thawed in a 37° C. waterbath and then placed on wet ice. Virus is diluted in cold cell culture medium as necessary to achieve the desired final virus concentration in the HIV-1pp assay (about 10,000 relative light units (rlu) per well), 50 μl of diluted virus are added per well, bringing the final well volume to 200 μl. A no-virus control (minimum or background luminescence) and a no-compound control (maximum luminescence) are included on each plate. The plates are incubated for 72 h at 37° C. in a humidified 5% $CO_2$ incubator followed by processing for luciferase signal (see below).

Plate Processing for Luciferase Assay

Assay medium is aspirated and 200 μl of PBS are added to each well. The PBS is aspirated and 50 μl of 1× Cell Lysis Reagent (Promega—Cat. No. E1531) are added to each well. Assay plates are then frozen for at least 2 h at −80° C. followed by thawing at room temperature and vigorous mixing with an electronic pipettor. 25 μl from each well are transferred to an opaque 96-well plate (Costar #3922). Four replicates are pooled into the same well on the opaque plate. 100 μl of freshly thawed and reconstituted luciferase substrate (Luciferase Assay System, Promega—Cat. No. E1501) are added to each well of the plate with the electronic pipettor, and luminescence is detected immediately on a Dynex MLX plate reader set to medium gain.

Data Analysis

Neutralization activity is displayed by plotting the percent inhibition of luciferase activity (after background rlu values are subtracted from all datapoints) versus $log_{10}$ drug concentration. The percent inhibition is derived as follows: [1−(luciferase activity in the presence of drug/luciferase activity in the absence of drug)]×100. $IC_{50}$ values are determined by fitting the inhibition data with a non-linear, four-parameter, variable slope equation (GraphPad Prism, ver. 4.02; GraphPad Software, San Diego, Calif.). Upper and lower inhibition values are constrained to 100% and 0%, respectively for curve fitting.

Synergy Determination

Cooperative interactions between PRO 140 and small-molecule and peptide-based inhibitors of CCR5, CD4, HIV-1 gp120, HIV-1 gp41 and HIV-1 reverse transcriptase (see Tables 4 and for listing of HIV-1 inhibitors approved for clinical use) are determined as described in Example 1. Cooperative inhibition effects of drug combinations are determined by the method of Chou and Talalay (1984). $IC_{50}$ values are generated for all combinations as described above. Combination Index (CI) and Dose Reduction (DR) values are calculated according to the following formulas:

$$CI = \left(\frac{IC_{50}Dcomb1}{IC_{50}Dsolo1}\right) + \left(\frac{IC_{50}Dcomb2}{IC_{50}Dsolo2}\right) + \alpha\left(\frac{(IC_{50}Dcomb1)(IC_{50}Dcomb2)}{(IC_{50}Dsolo1)(IC_{50}Dsolo2)}\right)$$

DR (for compound 1)=$(IC_{50}Dsolo1/IC_{50}Dcomb1)$

DR (for compound 2)=$(IC_{50}Dsolo2/IC_{50}Dcomb2)$

Where:

"$IC_{50}$ Dcomb1"=$IC_{50}$ of drug 1 in combination with drug 2;

"$IC_{50}$ Dsolo1"=$IC_{50}$ of drug 1 when tested alone;

"$IC_{50}$ Dcomb2"=$IC_{50}$ of drug 2 in combination with drug 1;

"$IC_{50}$ Dsolo2"=$IC_{50}$ of drug 2 when tested alone;

$\alpha=0$ if the effects of the two drugs are mutually exclusive; and $\alpha=1$ if the effects of the two drugs are mutually nonexclusive.

Combinations with CI<1 are determined to be synergistic, whereas combinations with CI>1 are determined to be antagonistic. Additivity is reflected in combinations for which CI=1.

Example 3

Combination Testing of Pro 140 with Small Molecule, Peptide and Protein Inhibitors in the HIV-1 Authentic Virus Replication Assay Materials and Methods Preparation of PBMCs Replication of authentic HIV-1 is measured in activated peripheral blood mononuclear cells (PBMCs) using the monocyte/macrophage-tropic HIV-1 clone, JRFL (HIV-$1_{JRFL}$), for these studies.

PBMCs are isolated from 4 separate donors (Leukopacks) by centrifugation on a Ficoll gradient. CD8 cells are depleted using RosetteSep CD8 Depletion Cocktail (#15663, Stem-Cell Research, Vancouver, BC). Cells are diluted to $4 \times 10^6$/ml and added in equal parts to three T175-$cm^2$ flasks and then stimulated by addition of one of the following media: IL-2 Medium [RPMI 1640 (#10-040-CV, Cellgro, Herndon, Va.), 10% FBS (#35-010-CV), 2 mM L-Glutamine (#25-005-CI), 100 U/ml IL-2 (Sigma, St. Louis, Mo.)]; PHA 5 Medium: [IL-2 Medium with 5 ug/ml Phytohemagglutinin PHA-P (PHA) (#L8754, Sigma, St. Louis, Mo.), filtered]; or PHA 0.5 Medium: [IL-2 Medium with 0.5 ug/ml PHA, filtered]. Each flask receives a total of 50-150 ml of medium. Flasks are incubated for 3 days at 37° C. followed by pooling of the contents prior to use in the infection assay.

Virus Titration

Serial dilutions of virus are tested in quadruplicate on activated PBMCs ($1.4 \times 10^5$ PBMC/well). Titration Medium [IL-2 Medium with 100 IU/ml penicillin/streptomycin (#30-002-CI, Cellgro)] is utilized for virus titrations. Fifty μl of diluted virus is added to 100 μl of PBMCs in flat bottom, tissue-culture treated 96-well plates (VWR#29442-054, Corning, Corning, N.Y.) and the plates are incubated at 37° C. in a humidified, 5% $CO_2$ incubator. After 7 days, 50 μl are removed from each well and tested for virus levels by p24 antigen ELISA (Perkin Elmer, Boston, Mass.). Virus titer is determined by the method of Reed and Muench (Table 11).

Neutralization Assay

Stimulated PBMCs are seeded into wells of 96-well flat bottom plates at a density of $1.4 \times 10^5$ cells/well. Virus is diluted to 2,000 $TCID_{50}$/ml and mixed with serial 0.5 $log_{10}$ dilutions of compound for 1 h at 37° C. prior to addition to the cell plates. The final amount of virus added per well is 100 $TCID_{50}$. The final DMSO concentration in the assay is always 0.5% whenever small molecule inhibitors are being tested. Plates are incubated at 37° C. for 5 days, at which time an aliquot of supernatant is removed for p24 antigen ELISA. If control wells (virus without inhibitor) exhibit low p24 antigen levels then the plates are brought back to full volume with Titration medium and incubated for an additional 24 h.

TABLE 11

Reed and Muench formula for calculating virus titer[a]

| No. of pos. wells | TCID$_{50}$/ml (10$^x$) |
|---|---|
| 1 | 0.74 |
| 2 | 0.83 |
| 3 | 0.92 |
| 4 | 1.00 |
| 5 | 1.09 |
| 6 | 1.17 |
| 7 | 1.26 |
| 8 | 1.35 |
| 9 | 1.44 |
| 10 | 1.52 |
| 11 | 1.61 |
| 12 | 1.70 |
| 13 | 1.79 |
| 14 | 1.87 |
| 15 | 1.96 |
| 16 | 2.05 |
| 17 | 2.14 |
| 18 | 2.22 |
| 19 | 2.31 |
| 20 | 2.40 |
| 21 | 2.49 |
| 22 | 2.57 |
| 23 | 2.66 |
| 24 | 2.75 |
| 25 | 2.83 |
| 26 | 2.92 |
| 27 | 3.01 |
| 28 | 3.10 |
| 29 | 3.18 |
| 30 | 3.27 |
| 31 | 3.36 |
| 32 | 3.45 |
| 33 | 3.53 |
| 34 | 3.62 |
| 35 | 3.71 |
| 36 | 3.80 |
| 37 | 3.88 |
| 38 | 3.97 |
| 39 | 4.06 |
| 40 | 4.15 |
| 41 | 4.23 |
| 42 | 4.32 |
| 43 | 4.41 |
| 44 | 4.49 |
| 45 | 4.58 |
| 46 | 4.67 |
| 47 | 4.76 |
| 48 | 4.84 |
| 49 | 4.93 |
| 50 | 5.02 |
| 51 | 5.11 |
| 52 | 5.19 |
| 53 | 5.28 |
| 54 | 5.37 |
| 55 | 5.46 |
| 56 | 5.54 |
| 57 | 5.63 |
| 58 | 5.72 |
| 59 | 5.81 |
| 60 | 5.89 |
| 61 | 5.98 |
| 62 | 6.07 |
| 63 | 6.15 |
| 64 | 6.24 |
| 65 | 6.33 |
| 66 | 6.42 |
| 67 | 6.50 |
| 68 | 6.59 |
| 69 | 6.68 |
| 70 | 6.77 |
| 71 | 6.85 |
| 72 | 6.94 |
| 73 | 7.03 |
| 74 | 7.12 |
| 75 | 7.20 |
| 76 | 7.29 |
| 77 | 7.38 |
| 78 | 7.47 |
| 79 | 7.55 |
| 80 | 7.64 |

[a]To calculate virus titer, first multiply the total number of positive wells by 2 (the chart was designed to be used with replicates of 8), then look up the corresponding TCID$_{50}$/mL titer and add 0.7 (the formula requires the addition of a log dilution factor).

Data Analysis

Neutralization activity is displayed by plotting the percent inhibition of p24 antigen production (after background values are subtracted from all datapoints) versus $\log_{10}$ drug concentration. The percent inhibition is derived as follows [1−(p24 levels in the presence of drug/p24 levels in the absence of drug)]×100. IC$_{50}$ values are determined by fitting the inhibition data with a non-linear, four-parameter, variable slope equation (GraphPad Prism, ver. 4.02; GraphPad Software, San Diego, Calif.). Upper and lower inhibition values are constrained to 100% and 0%, respectively for curve fitting.

Synergy Determinations

Cooperative interactions between PRO 140 and small-molecule and peptide-based inhibitors of CCR5, CD4, HIV-1 gp120, HIV-1 gp41, HIV-1 reverse transcriptase and HIV-1 protease (Table 8) are determined as described for Example 1. Cooperative inhibition effects of drug combinations are determined by the method of Chou and Talalay (1984). IC$_{50}$ values are generated for all combinations as described above. Combination Index (CI) and Dose Reduction (DR) values are calculated according to the following formulas:

$$CI = \left(\frac{IC_{50}Dcomb1}{IC_{50}Dsolo1}\right) + \left(\frac{IC_{50}Dcomb2}{IC_{50}Dsolo2}\right) + \alpha\left(\frac{(IC_{50}Dcomb1)(IC_{50}Dcomb2)}{(IC_{50}Dsolo1)(IC_{50}Dsolo2)}\right)$$

DR (for compound 1)=(IC$_{50}$Dsolo1/IC$_{50}$Dcomb1)

DR (for compound 2)=(IC$_{50}$Dsolo2/IC$_{50}$Dcomb2)

Where:
"IC$_{50}$ Dcomb1"=IC$_{50}$ of drug 1 in combination with drug 2;
"IC$_{50}$ Dsolo1"=IC$_{50}$ of drug 1 when tested alone;
"IC$_{50}$ Dcomb2"=IC$_{50}$ of drug 2 in combination with drug 1;
"IC$_{50}$ Dsolo2"=IC$_{50}$ of drug 2 when tested alone;
α=0 if the effects of the two drugs are mutually exclusive; and
α=1 if the effects of the two drugs are mutually nonexclusive.

Combinations with CI<1 are determined to be synergistic, whereas combinations with CI>1 are determined to be antagonistic. Additivity is reflected in combinations for which CI=1.

Discussion

PRO 140 is a CCR5-specific mAb being developed for HIV-1 therapy. It is a humanized IgG4,κ version (see PCT International Publication No. WO 03/072766, published Sep. 4, 2003) of the murine antibody, PA14 (Olson et al., 1999;

PCT International Publication No. WO 00/35409, published Jun. 20, 2000), which binds to the CCR5 receptor on the surface of a cell and inhibits CCR5-mediated fusion of HIV-1 to the cell. The studies described herein concern the testing of the antiviral activity of PRO 140 in combination with small-molecule and peptide inhibitors of HIV-1 infection. Data generated from this testing were analyzed for potential cooperative effects on inhibition of HIV-1 infection.

In one series of experiments, inhibition of HIV-1 infection was assayed using a fluorescence resonance energy transfer (RET) assay, which measures the fusion of effector cells (HeLa-Env$_{JRFL}$) expressing recombinant HIV-1 strain JRFL envelope glycoproteins (Env) to target cells (CEM NKR-CCR5) expressing CD4 and CCR5 (Litwin et al., 1996). In this assay, effector cells are labeled with the F18 dye and target cells with the R18 dye. HIV-1 Env-mediated fusion of effector and target cells results in the placement of these two dyes within close proximity in the cell membrane. When F18 is excited at its optimum wavelength (450 nm), it emits light at a wavelength (530 nm) that will excite R18 when the two dyes are co-localized in the same membrane, resulting in R18-specific emission at 590 nm. Drug susceptibility is measured by adding serial concentrations of drugs to target cells prior to addition of effector cells. Inhibition of HIV-1 Env-mediated fusion is reflected in a reduction in fluorescence emission due to R18 in a dose-dependent manner, providing a quantitative measure of drug activity.

Initial experiments measuring inhibition of HIV-1 Env-mediated fusion were conducted in order to demonstrate the robustness of the assay system for quantifying cooperative interactions. In these experiments, PRO 140 was run in combination with itself, a combination that should result in combination index (CI) values indicative of additive interactions. Using the methodology of Chou and Talalay (1984), CI values of <1.0, =1.0 and >1.0 are taken to indicate synergistic, additive and antagonistic interactions, respectively. Indeed, PRO 140 run in combination with itself returned a CI value of 0.97±0.08 (n=9; Table 7), indicating that the assay system accurately represented this interaction.

Synergy experiments were then conducted between PRO 140 and 3 small-molecule (SCH-D, TAK-779, UK427857), one peptide (RANTES) and one mAb (2D7) antagonist of CCR5. In addition, cooperative interactions were measured between PRO 140 and T-20 (peptide-based inhibitor of gp41), PRO 542 (protein-based inhibitor of gp120), BMS378806 (small molecule inhibitor of gp120) and Leu-3A (anti-CD4 mAb).

The results (see Table 7) revealed potent synergy between PRO 140 and all 3 small-molecule CCR5 antagonists as well as RANTES. CI values between PRO 140 and these CCR5 antagonists ranged from 0.36±0.10 to 0.59±0.08. Dose reduction values indicated that the compound in combination exerted about a 4-fold effect on PRO 140 activity, whereas the effect of PRO 140 on the compound in combination ranged from about 3- to about 16-fold (Table 7). Modest synergy to additivity was observed between PRO 140 and T-20, PRO 542, BMS-378806 and 2D7 (CI=0.84±0.16, 0.96±0.17, 1.21±0.21, and 0.93±0.04, respectively).

Small molecule antagonists of CCR5 run in combination (SCH-D and TAK-779) returned a mean CI value of 1.12±0.32, indicating a slightly additive interaction (Table 8). Conversely, the combination of the recombinant antibody-like fusion protein PRO 542 with the anti-CD4 mAb, Leu-3A, resulted in a mean CI value of 16.9±0.3, indicating potent antagonism between these two HIV-1 inhibitors (Table 8).

Varying the molar ratios of compounds demonstrated similar patterns of cooperativity. At both 5:1 and 1:5 molar ratios of PRO 140 to SCH-D, TAK-779, UK-427,857 and RANTES, potent synergistic inhibition of HIV-1-Env-mediated entry was observed (Table 9). This represents a broad range of inhibitor mass ratios, from a low of 0.15 to a high of 1,820. CI values between PRO 140 and CCR5 antagonists ranged from 0.52±0.20 to 0.84±0.14. More modest synergy to additivity was observed for combinations of PRO 140 with T-20, PRO 542 or BMS-378806. The results of these investigations identify clearly the potent synergistic activities of PRO 140 with CCR5 antagonists, as well as more modest synergy between PRO 140 and T-20 (see FIG. 4).

The HIV-1 inhibitory activity of the CCR5-specific murine mAb, 2D7, in combination with the small-molecule CCR5 antagonists and with RANTES, was also tested using the fluorescent RET assay. 2D7 was found to act synergistically with these CCR5 antagonists and with RANTES (Table 10). CI values between 2D7 and these CCR5 antagonists ranged from 0.15±0.03 to 0.62±0.04. Dose reduction values indicated that the compound in combination exerted about a 2- to 3-fold effect on 2D7 activity, except for TAK-779 which had an approximately 17-fold effect on 2D7 activity. The effect of 2D7 on the compound in combination ranged from about 2- to about 12-fold (Table 10). As observed previously, PRO 140 and 2D7 in combination were essentially additive or modestly synergistic (CI=0.93±0.04).

These results indicate that synergistic inhibition of HIV-1 Env-mediated cell-cell fusion is observed between multiple mAbs and small molecules that bind to CCR5. This property may be broadly applicable to mAbs that target CCR5, including, for example, the mAb CCR5mAb004 that has been shown to bind to and antagonize CCR5 and block HIV-1 entry in a cell-cell fusion assay (Roschke et al., 2004). A large and growing number of small molecules have been identified as CCR5 antagonists (see Table 12). Certain of these small molecule CCR5 antagonists may also produce synergistic inhibition of HIV-1 Env-mediated fusion in combination with PRO140 and other anti-CCR5 mAbs.

An alternative approach for examining synergistic interactions utilizes a virus-cell fusion assay as described previously (Nagashima et al., 2001; Trkola et al., 1998). In this assay an HIV genomic vector (pNLluc$^+$Env$^-$) containing a luciferase reporter gene is pseudotyped with Env from HIV-1$_{JRFL}$. Recombinant pseudotyped virus particles are used to infect U87 cells expressing CD4 and CCR5 (U87-CD4-CCR5). Production of luciferase in target cells is dependent on virus entry and the completion of one round of virus replication. Drug susceptibility is measured by adding serial concentrations of drugs to target cells prior to addition of pseudotyped virus particles. Inhibition of virus entry is reflected in a reduction in luciferase activity in a dose-dependent manner, providing a quantitative measure of drug susceptibility. Since the HIV genomic vector requires expression of functional HIV-1 reverse transcriptase (RT) to drive luciferase expression, this pseudovirus assay is also sensitive to inhibition by nucleotide/nucleoside reverse transcriptase inhibitors (NRTIs) and non-nucleoside reverse transcriptase inhibitors (NNRTIs). As such, the HIV-1pp assay is suitable for examining cooperative interactions between PRO 140 and small-molecule, peptide and protein inhibitors of CCR5, CD4, HIV-1 gp120, HIV-1 gp41 and HIV-1 reverse transcriptase.

TABLE 12

Small-Molecule CCR5 antagonists

| Small-Molecule CCR5 antagonist | Reference |
| --- | --- |
| 1,3,4-trisubstituted pyrrolidines | Kim et al., 2005 |
| Modified 4-piperidinyl-2-phenyl-1-(phenylsulfonylamino)-butanes | Shah et al., 2005 |
| Anibamine•TFA, Ophiobolin C, and 19,20-epoxycytochalasin Q | Jayasuriya et al., 2004 |
| 5-(piperidin-1-yl)-3-phenyl-pentylsulfones | Shankaran et al., 2004a |
| 4-(heteroarylpiperdin-1-yl-methyl)-pyrrolidin-1-yl-acetic acid antagonists | Shankaran et al., 2004b |
| Agents containing 4-(pyrazolyl)piperidine side chains | Shu et al., 2004 |
| Agents containing 4-(pyrazolyl)piperidine side chains. | Shen et al., 2004a; 2004b |
| 3-(pyrrolidin-1-yl)propionic acid analogues | Lynch et al., 2003c |
| [2-(R)-[N-methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)amino]-3-methylbutanoic acid (MRK-1)] | Kumar et al., 2003 |
| 1,3,4 trisubstituted pyrrolidines bearing 4-aminoheterocycle substituted piperidine side chains | Willoughby et al., 2003; Lynch et al., 2003a; Lynch et al., 2003b; Hale et al., 2002 |
| Bicyclic isoxazolidines | Lynch et al., 2002 |
| Combinatorial synthesis of CCR5 antagonists | Willoughby et al., 2001 |
| Heterocycle-containing compounds | Kim et al., 2001b |
| Antagonists containing hydantoins | Kim et al., 2001a |
| 1,3,4 trisubstituted pyrrolidines | Hale et al., 2001 |
| 1-[N-(methyl)-N-(phenylsulfonyl)amino]-2-(phenyl)-4-(4-( N-(alkyl)-N-(benzyloxycarbonyl)amino)piperidin-1-yl)butanes | Finke et al., 2001 |
| Compounds from the plant *Lippia alva* | Hedge et al., 2004 |
| Piperazine-based CCR5 antagonists | Tagat et al., 2004 |
| Oximino-piperidino-piperidine-based CCR5 antagonists | Palani et al., 2003b |
| Rotamers of SCH 351125 | Palani et al., 2003a |
| Piperazine-based symmetrical heteroaryl carboxamides | McCombie et al., 2003 |
| Oximino-piperidino-piperidine amides | Palani et al., 2002 |
| Sch-351125 and Sch-350634 | Este, 2002 |
| SCH-C | Strizki et al., 2001 |
| 1-[(2,4-dimethyl-3-pyridinyl)carbonyl]-4-methyl-4-[3(S)-methyl-4-[1(S)-[4-(trifluoromethyl)phenyl]ethyl]-1-piperazinyl]-piperidine N1-oxide (Sch-350634) | Tagat et al., 2001a |
| 4-[(Z)-(4-bromophenyl)-(ethoxyimino)methyl]-1'-[(2,4-dimethyl-3-pyridinyl)carbonyl]-4'-methyl-1,4'-bipiperidine N-oxide (SCH 351125) | Palani et al., 2001 |
| 2(S)-methyl piperazines | Tagat et al., 2001b |
| Piperidine-4-carboxamide derivatives | Imamura et al., 2005 |
| 1-benzazepine derivatives containing a sulfoxide moiety | Seto et al., 2005 |
| anilide derivatives containing a pyridine N-oxide moiety | Seto et al., 2004a |
| 1-benzothiepine 1,1-dioxide and 1-benzazepine derivatives containing a tertiary amine moiety | Seto et al., 2004b |
| N-[3-(4-benzylpiperidin-1-yl)propyl]-N,N'-diphenylureas | Imamura et al., 2004a |
| 5-oxopyrrolidine-3-carboxamide derivatives | Imamura et al., 2004b |
| Anilide derivatives with a quaternary ammonium moiety | Shiraishi et al., 2000 |
| AK602/ONO4128/GW873140 | Nakata et al., 2005 |
| Spirodiketopiperazine derivatives | Maeda et al., 2001; Maeda et al., 2004 |
| Selective CCR5 antagonists | Thoma et al., 2004 |

A third approach for examining antiviral synergy utilizes a whole virus assay. Cooperativity between all classes of inhibitor molecules can be examined in this assay format.

In both the virus-cell fusion luciferase assay and the whole virus assay, $IC_{50}$ values are generated for all combinations as described herein for the RET assay. Cooperative inhibition effects of drug combinations are determined by the method of Chou and Talalay (1984).

PRO 140 broadly and potently inhibited CCR5-mediated HIV-1 entry without CCR5 antagonism or other immunologic side effects in preclinical testing. More recently, PRO 140 has demonstrated favorable tolerability, PK and immunologic profiles in preliminary results from an ongoing Phase 1a study in healthy volunteers. Thus, in many respects, PRO 140 offers a novel and attractive product profile for anti-HIV-1 therapy. Moreover, the activities of anti-CCR5 mAbs are fundamentally distinct from, but complementary to, those of small-molecule CCR5 antagonists (see Table 2).

It might have been expected that combinations of anti-CCR5 mAbs and non-antibody CCR5 antagonists would produce additive effects in inhibiting fusion of HIV-1 to $CD4^+$ $CCR5^+$ target cells since both classes of agents bind to the same target molecule. Surprisingly, however, the data presented herein reveal that anti-CCR5 mAbs, exemplified by PRO 140 and 2D7, exhibited potent and reproducible synergy with non-antibody CCR5 antagonists, exemplified by SCH-D, TAK-779, UK-427,857 and RANTES, in inhibiting HIV-1 Env-mediated cell-cell fusion. Synergies routinely translated into 4- to 10-fold dose reductions, suggesting significant improvement in inhibitory potency for the drug combinations. In contrast, purely additive effects were observed for combinations of non-antibody CCR5 antagonists. These findings likely reflect the different patterns of CCR5 recognition of these molecules: whereas small-molecule CCR5 antagonists bind a common hydrophobic pocket within the transmembrane domains of CCR5, PRO 140 recognizes a hydrophilic, extracellular epitope of CCR5. Overall, the data support the use of PRO 140 in combination with non-antibody HIV-1 entry inhibitors and suggest that PRO 140 represents a distinct subclass of CCR5 inhibitor.

Moreover, the available data suggest that the observed synergy may also be exhibited by combinations involving anti-CCR5 mAbs other than PRO 140, including, but not limited to, mAb CCR5mAb004 (Roschke et al., 2004), as well as non-antibody CCR5 antagonists other than SCH-D, TAK-779, UK-427,857 and RANTES. Thus, these antibodies likely produce synergistic effects in combination with GW873140 (Lalezari et al., 2004), TAK-652 (Baba et al., 2005), and at least certain of the small-molecule CCR5 antagonists listed in Table 12. Accordingly, combination therapy comprising administration of anti-CCR5 mAbs and non-antibody CCR5 antagonists may offer powerfully effective, new approaches to preventing and treating HIV-1 infection. It is expected that such therapy will result in more potent and more durable ant-HIV-1 treatments. Additionally, the synergistic effects described herein may enable a reduction in dosages of drugs administered to a subject as well as a reduction in dosing frequency.

Example 4

Loading and Maintenance Dose Regimens

The loading regimen, which can, for example, be more dose-intensive than the maintenance regimen, can, for example, have the following characteristics:

Number of doses: 1 or more (up to about 5 doses).

Dose level: About 25%, 50%, 75%, 100%, 150% or 200% greater than the maintenance dose regimen.

Dose frequency: About 1.5×, 2×, 3× or 4× more frequently than the maintenance dose regimen.

As an example, if the maintenance dose regimen is 2 mg/kg every two weeks, the loading dose regimen could comprise weekly 2 mg/kg doses. Alternatively, the loading dose regimen could comprise a single 4 mg/kg dose or multiple 4 mg/kg doses at weekly or biweekly intervals.

The loading dose regimen can be designed, for example, so as to accelerate the achievement of a pharmacokinetic steady state in the subject, as defined by uniform peak and trough blood concentrations of drug between doses. A preferred loading dose regimen can be determined by routine experimentation wherein the drug is administered to the subject by differing loading and maintenance regimens, and blood levels of drug are measured.

Also, in another embodiment, PRO 140 is administered according to a fixed-dose regimen such as, for example, 75 mg, 150 mg, 300 mg and 600 mg per administration.

Part III

Materials And Methods

Inhibitors

PRO 140 was expressed in mammalian cells and purified by protein A, ion exchange and hydroxyapatite chromatographies. UK-427,857 (Dorr et al. 2005), SCH-D (Tagat et al. 2004), TAK-779 (Baba et al. 1999), enfuvirtide (T-20 (Wild et al. 1992); BMS-378806 (Lin et al. 2003)) and PRO 542 (CD4-IgG2, (Allaway et al. 1995)) were prepared according to published methods. Zidovudine (azidothymidine, AZT), RANTES, the CCR5 mAb 2D7 and the CD4 mAb Leu-3A were purchased from Sigma Chemicals (St. Louis, Mo.), R&D Systems (Minneapolis, Minn.), Pharmingen (San Diego, Calif.), and Becton Dickinson (Franklin Lakes, N.J.), respectively. UK-427,857 and SCH-D were radiolabeled with tritium by GE Healthcare (Piscataway, N.J.), and PRO 140 was conjugated to phycoerythrin (PE) by Southern Biotech, Inc. (Birmingham, Ala.).

HIV-1 Membrane Fusion Assay

HIV-1 envelope-mediated membrane fusion was examined using a fluorescence resonance energy transfer (RET) assay (Litwin et al. 1996) with modifications. Briefly, HeLa cells that stably express HIV-1$_{JR-FL}$ gp120/gp41 (Litwin et al. 1996) and CEM.NKR-CCR5 cells (NIH AIDS Research and Reference Reagent Program, (Spenlehauer et al. 2001; Trkola et al. 1999)) were labeled separately overnight with fluorescein octadecyl ester (F18; Molecular Probes, Eugene, Oreg.) and rhodamine octadecyl ester (R18; Molecular Probes), respectively. Cells were washed in phosphate-buffered saline containing 15% fetal bovine serum (PBSF) and co-seeded at 15,000 cells/well into a 384-well plate. Inhibitors were added, and the plates were incubated in PBSF plus 0.5% dimethylsulfoxide (DMSO) for 4 h at 37° C. prior to measurement of RET using a Victor$^2$ plate reader (Perkin-Elmer, Boston, Mass.) as previously described (Litwin et al. 1996). The CD4 mAb Leu3a was used as a control inhibitor, and percent inhibition was calculated as: (RET in the absence of inhibitor—RET in the presence of inhibitor)/(RET in the absence of inhibitor—RET in the presence of Leu3a)×100.

HIV-1 Pseudovirus Assay

A self-inactivating (SIN) vector was derived from the pNL4-3ΔEnv-luciferase vector (Dragic et al. 1996) by deleting 507 basepairs in the U3 region of the 3' long terminal repeat (LTR) so as to remove the TATA box and transcription factor binding sites. The human cytomegalovirus promoter was inserted upstream of the luciferase (luc) gene to enable expression of luciferase following integration.

Reporter viruses pseudotyped with HIV-1$_{JR-FL}$ or HIV-1$_{SF162}$ envelopes were generated by cotransfection of 293T cells with the SIN vector and the appropriate pcDNA env-expressing vector as previously described (Dragic et al, 1996). U87-CD4-CCR5 cells (8,000/well; NIH AIDS Research and Reference Reagent Program) were infected with 125-375 pg of HIV-1 pseudoviruses in 384-well plates in the presence or absence of inhibitor(s). Cultures were incubated for 72 h at 37° C. in DMEM containing 10% fetal bovine serum, 1 mg/mL puromycin, 0.3 mg/mL geneticin, antibiotics, and 0.5% DMSO. Luciferase activity (relative light units or RLU) was measured using BrightGlo reagent (Promega, Madison, Wis.) according to the manufacturer's instructions. Percent inhibition was calculated as: (1−RLU in the presence of inhibitor/RLU in the absence of inhibitor)× 100. IC50 and IC90 were used to denote the respective concentrations required for 50% and 90% inhibition of HIV-1.

Synergy Determinations

Experimental design and data analysis were based on the combination index (CI) method (Chou et al. 1991; Chou et al. 1984). Compounds were tested individually and in combination at a fixed molar ratio over a range of serial dilutions. Entry inhibitors were combined in equimolar amounts, whereas a 1:10 molar ratio was used for PRO 140 in combination with azidothymidine and nevirapine. Dose-response curves were fit using a four-parameter sigmoidal equation with upper and lower inhibition values constrained to 100% and 0%, respectively, in order to calculate concentrations required for 50% (IC50) and 90% (IC90) inhibition (GraphPad Prism, GraphPad Software, San Diego, Calif.). CI values for 50% (CI50) and 90% (CI90) inhibition were calculated as previously described (Chou et al. 1991; Chou et al. 1984). The mutually exclusive CI formula was used for combinations of CCR5 inhibitors, while the mutually non-exclusive formula was utilized for combinations of inhibitors to distinct targets (Chou et al. 1991). Each test was conducted 4-12 times. Synergy, additivity and antagonism are indicated by CI<1, CI=1 and CI>1, respectively.

Competition Binding Assays

To examine inhibition of PRO 140 binding, CEM.NKR-CCR5 cells were suspended in phosphate-buffered saline with 0.1% sodium azide (PBSA) and incubated with varying concentrations of unlabeled CCR5 antagonists at ambient temperature for 30 minutes. Azide was added to block CCR5 internalization during the assay. Cells were washed in PBSA and incubated with 5 nM PRO 140-PE for an additional 30 minutes prior to washing and analysis by flow cytometry using a FACSCalibur instrument (Becton Dickinson). The extent of PRO 140-PE binding was measured in terms of both the mean fluorescence intensity (MFI) and the percent of cells gated for positive staining.

To examine inhibition of UK-427,857 binding, CEM.NKR-CCR5 cells were pre-incubated with unlabeled CCR5 inhibitors as described above prior to addition of 2 nM $^3$H-UK-427,857 for an additional 30 minutes. The cells were washed in PBSA and lysed with 0.5N HCl prior to scintillation counting using a Wallac1410 instrument. An additional study reversed the order of addition in order to examine the stability of UK-427,857 binding over the course of the assay. Cells were pre-incubated with 2 nM $^3$H-UK-427,857 for 30 min prior to washing, addition of unlabeled inhibitors, and processing as described above. EC50 and EC90 were used to denote the concentrations of unlabeled compound required to inhibit binding of labeled compound by 50% and 90%, respectively.

Statistical Analyses

Two-tailed t-tests were used to test mean CI50 and CI90 values for the null hypothesis $H_0$: CI=1 (additivity) using GraphPad Prism software. P values were corrected for multiple comparisons from $\alpha$=0.05 according to the Bonferroni method (Cudeck and O'Dell 1994), excluding the PRO 140/PRO 140 mock combination that was included as an assay control. In the Bonferroni correction, P=$\alpha$/n, where n is the number of comparisons. Twenty-two synergy comparisons (11 compounds×2 CI values) were made based on data generated in the membrane fusion assay, resulting in a corrected P value of 0.0023. In the pseudovirus assay, 32 synergy comparisons (8 compounds×2 viruses×2 CI values) resulted in a corrected P value of 0.0016.

Results

Inhibition of HIV-1 Membrane Fusion

Figure 15:
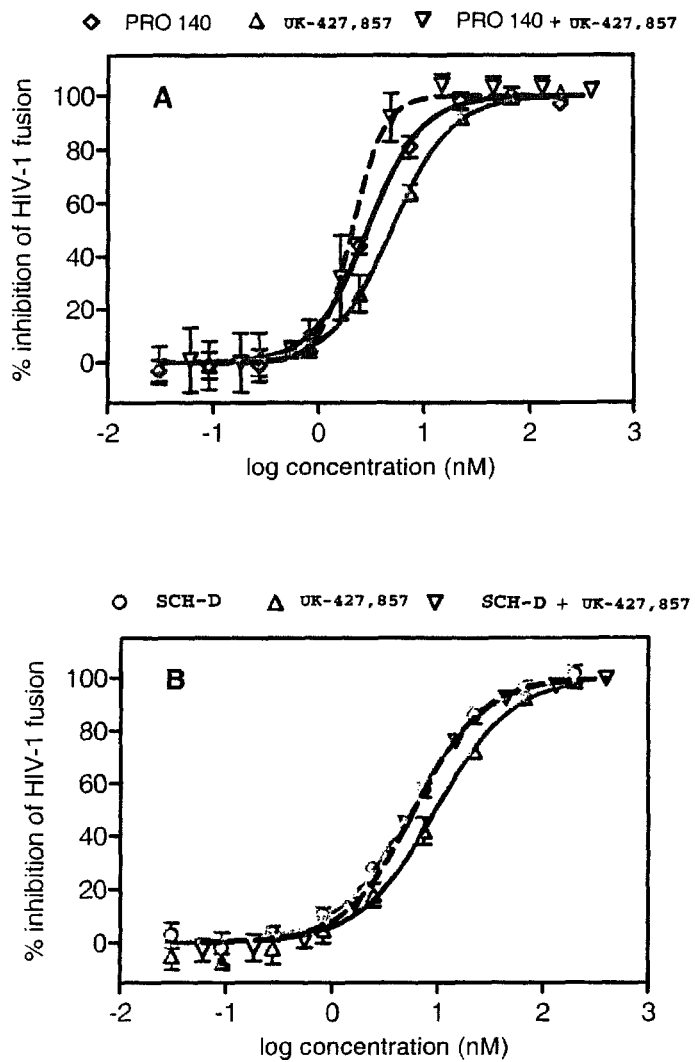

PRO 140 and UK-427,857 were used individually and together to inhibit HIV-1$_{JR-FL}$ envelope-mediated membrane fusion in the RET cell-cell fusion assay, and representative dose-response curves for the individual agents and combination are illustrated in FIG. 15A. Although both PRO 140 and UK-427,857 individually blocked HIV-1 fusion at low nanomolar potency, the combination was markedly more potent. In this assay, 50% inhibition was obtained using 2.9 nM PRO 140 alone, 5.0 nM UK-427,857 used alone, or 2.1 nM of the combination (1.05 nM PRO 140 plus 1.05 nM UK-427,857). This supra-additive effect is indicative of antiviral synergy between the two agents. In contrast, the combination of SCH-D and UK-427,857 was no more potent than individual agents (FIG. 15B). In this example, the dose-response curves for the individual inhibitors and the combination were overlapping, with 50% inhibition requiring 9.7 nM UK-427,857, 5.5 nM SCH-D and 6.1 nM of the combination. The data suggest purely additive effects for these inhibitors.

These studies were extended to additional CCR5 (TAK-779, RANTES and 2D7), gp120 (BMS-378806 and PRO 542) and gp41 (enfuvirtide) inhibitors, and were repeated four or more times for each condition. CI50 and CI90 values were calculated for each condition and averaged across the independent assays. Cooperativity was assessed using t-tests to determine if the CI50 and CI90 values were significantly different from one. As a test of these methods, a PRO 140/PRO 140 mock combination was examined by adding PRO 140 to the assay wells in two separate additions. CI50 and CI90 values for the PRO 140/PRO 140 combination were 0.96 and 0.97, respectively (Table 13); therefore, purely additive effects were observed for this mock combination, as expected.

TABLE 13

CI values for inhibition of HIV-1$_{JR-FL}$ envelope-mediated membrane fusion[a]

| 1$^{st}$ Inhibitor | Target | IC50, nM | IC90, nM | 2$^{nd}$ Inhibitor | CI50 | P value | CI90 | P value |
|---|---|---|---|---|---|---|---|---|
| PRO 140 | CCR5 | 2.5 | 8.6 | PRO 140 | 0.97 ± 0.07 | 0.13 | 0.96 ± 0.14 | 0.37 |
| UK-427,857 | CCR5 | 5.3 | 27 | PRO 140 | *0.61 ± 0.05* | *<0.0001* | *0.40 ± 0.06* | *<0.0001* |
| SCH-D | CCR5 | 3.2 | 16 | PRO 140 | *0.51 ± 0.05* | *<0.0001* | *0.36 ± 0.06* | *<0.0001* |
| TAK-779 | CCR5 | 11 | >200 | PRO 140 | *0.38 ± 0.08* | *<0.0001* | N/A | N/A |
| RANTES | CCR5 | 2.4 | 38 | PRO 140 | *0.59 ± 0.08* | 0.0022 | *0.43 ± 0.05* | 0.0002 |
| RANTES | CCR5 | 2.4 | 38 | UK-427,857 | *0.48 ± 0.03* | 0.0017 | *0.18 ± 0.01* | *<0.0001* |
| SCH-D | CCR5 | 3.2 | 16 | UK-427,857 | 0.86 ± 0.03 | 0.016 | 0.75 ± 0.02 | 0.0033 |
| SCH-D | CCR5 | 3.2 | 16 | TAK-779 | 1.3 ± 0.18 | 0.12 | N/A | N/A |
| 2D7 | CCR5 | 3.7 | 58 | PRO 140 | 1.0 ± 0.14 | 0.61 | 1.9 ± 0.61 | 0.024 |
| enfuvirtide | gp41 | 8.6 | 66 | PRO 140 | 0.84 ± 0.16 | 0.040 | 0.89 ± 0.20 | 0.19 |
| PRO 542 | gp120 | 8.9 | 91 | PRO 140 | 0.96 ± 0.17 | 0.56 | 0.94 ± 0.19 | 0.45 |
| BMS-378806 | gp120 | 5.2 | 20 | PRO 140 | *1.3 ± 0.19* | 0.0015 | 1.1 ± 0.22 | 0.19 |

[a]Statistically significant results (P < 0.0023 after application of the Bonferroni correction for multiple comparisons) are indicated in italicized bold text.
IC50 and IC90 denote values for the 1$^{st}$ inhibitor.
N/A = not applicable;
TAK-779 did not consistently achieve 90% inhibition in the assay.
CI values represent the means and standard deviations of 4-12 independent assay Potent synergy was observed for PRO 140 in combination with each of three small-molecule CCR5 antagonists (UK-427,857, SCH-D and TAK-779), and the findings were statistically significant even when the data were corrected for multiple comparisons via the Bonferroni method (Table 13). CI values ranged from 0.36 to 0.61, and these synergies translated into dose reductions ranging from 3- to 8-fold across the different conditions. Synergies were greater at 90% inhibition than at 50% inhibition. Synergy between PRO 140 and small-molecule CCR5 antagonists was robust in that it was observed at both the 50% and 90% inhibition levels in every instance. The exception was TAK-779, which did not mediate 90% inhibition when used individually, and therefore a CI90 was not determined. Similarly potent synergy was observed when RANTES was used in combination with either PRO 140 or UK-427,857 (Table 13). Additional tests examined combinations of two small-molecule CCR5 antagonists (SCH-D/UK-427,857 and SCH-D/TAK-779) or two CCR5 mAbs (PRO 140/2D7). No significant synergy was observed for these combinations, although the SCH-D/UK-427,857 CI90 values trended towards significance. The findings are consistent with prior observations of overlapping binding sites for PRO 140 and 2D7 (Olson et al. 1999) and for SCH-D and TAK-779 (Seibert et al. 2006). PRO 140 was also tested in combination with the gp41 fusion inhibitor enfuvirtide and with the gp120 attachment inhibitors PRO 542 and BMS-378806 (Table 13). CI values ranged from 0.84 to 1.28, and none of these combinations demonstrated synergy that met the criteria for statistical significance. For the PRO 140/BMS-378806 combination, modest antagonism was observed at 50% but not 90% inhibition. The biological significance of this result is unclear.

Inhibition of HIV-1 Pseudoviruses

Single-cycle HIV-1 reporter viruses were used to examine whether the synergistic effects were limited to cell-cell fusion or whether they extended to other modes of HIV-1 entry. Signals in this assay require both viral entry and reverse transcription, so that both NRTI and NNRTI may be included in the analyses. Each combination was tested against reporter viruses pseudotyped with envelopes from HIV-1$_{JR-FL}$ and HIV-1$_{SF162}$ in at least 4 independent assays per virus. A PRO 140/PRO 140 mock combination was again included as an assay control, and demonstrated additive effects against both HIV-1$_{JR-FL}$ and HIV-1$_{SF162}$ pseudoviruses, as expected (Table 14).

PRO 140 potently synergized with both UK-427,857 and SCH-D in blocking virus-cell fusion, and the results met the criteria for statistical significance. Comparable levels of synergy were observed against both HIV-1$_{JR-FL}$ and HIV-1$_{SF162}$ pseudoviruses at 50% and 90% inhibition (Table 14), with CI values ranging from 0.18 to 0.64. These synergies translated into dose reductions ranging to 14-fold. These results are in good agreement with those obtained in the cell-cell fusion assay (Table 13). Neither TAK-779 nor RANTES mediated consistent, high-level inhibition of HIV-1 pseudovirus entry, and therefore these compounds were not included in this analysis (data not shown).

TABLE 14

CI values for inhibition of HIV-1 reporter viruses pseudotyped with envelopes from HIV-1$_{JR-FL}$ and HIV-1$_{SF162}$.[a]

| 1st Inhibitor | Target | HIV-1 Envelope | IC50, nM | IC90, nM | 2nd Inhibitor | CI50 | P value | CI90 | P value |
|---|---|---|---|---|---|---|---|---|---|
| PRO 140 | CCR5 | JRFL | 2.2 | 28 | PRO 140 | 1.2 ± 0.32 | 0.16 | 0.90 ± 0.15 | 0.047 |
|  |  | SF162 | 1.3 | 20 | PRO 140 | 1.0 ± 0.27 | 1.0 | 0.86 ± 0.33 | 0.21 |
| SCH-D | CCR5 | JRFL | 2.4 | 44 | PRO 140 | *0.47 ± 0.15* | *<0.001* | *0.18 ± 0.04* | *<0.001* |
|  |  | SF162 | 0.34 | 14 | PRO 140 | *0.60 ± 0.17* | *<0.001* | *0.28 ± 0.11* | *<0.001* |
| UK-427,857 | CCR5 | JRFL | 7.4 | 46 | PRO 140 | *0.44 ± 0.06* | *<0.001* | *0.28 ± 0.11* | *<0.001* |
|  |  | SF162 | 0.87 | 13 | PRO 140 | *0.64 ± 0.07* | *<0.001* | *0.24 ± 0.11* | *<0.001* |
| UK-427,857 | CCR5 | JRFL | 7.4 | 46 | SCH-D | 0.71 ± 0.11 | 0.16 | 1.2 ± 0.15 | 0.32 |
|  |  | SF162 | 0.87 | 13 | SCH-D | 0.87 ± 0.06 | 0.19 | 0.86 ± 0.28 | 0.61 |
| 2D7 | CCR5 | JRFL | 8.8 | >200 | PRO 140 | 1.5 ± 0.25 | 0.024 | N/A | N/A |
|  |  | SF162 | 2.2 | 74 | PRO 140 | 1.1 ± 0.47 | 0.61 | 1.0 ± 0.16 | 0.65 |
| PRO 542 | gp120 | JRFL | 0.19 | 2.9 | PRO 140 | 1.2 ± 0.32 | 0.22 | 1.0 ± 0.18 | 0.92 |
|  |  | SF162 | 0.36 | 7.1 | PRO 140 | 0.98 ± 0.28 | 0.84 | 0.64 ± 0.26 | 0.010 |
| BMS-378806 | gp120 | JRFL | 1.2 | 11 | PRO 140 | 1.2 ± 0.38 | 0.43 | 0.74 ± 0.23 | 0.059 |
|  |  | SF162 | 0.03 | 0.42 | PRO 140 | 1.1 ± 0.28 | 0.36 | 0.82 ± 0.21 | 0.068 |
| nevirapine | RT | JRFL | 30 | 310 | PRO 140 | 1.2 ± 0.38 | 0.36 | 0.73 ± 0.28 | 0.068 |
|  |  | SF162 | 42 | 280 | PRO 140 | 1.2 ± 0.34 | 0.30 | 0.63 ± 0.19 | 0.033 |
| zidovudine | RT | JRFL | 140 | 1900 | PRO 140 | 1.1 ± 0.38 | 0.37 | 0.85 ± 0.26 | 0.21 |
|  |  | SF162 | 86 | 2100 | PRO 140 | 0.99 ± 0.27 | 0.91 | 1.0 ± 0.38 | 1.0 |

[a] Statistically significant results (P < 0.0016 after application of the Bonferroni correction for multiple comparisons) are indicated in italicized bold text.
IC50 and IC90 refer to values for the 1st inhibitor.
N/A = not applicable;
2D7 did not consistently achieve 90% inhibition in the assay.
CI values represent the means and standard deviations of 4 or more independent assays Additive effects were observed for both the UK-427,857/SCH-D and PRO 140/2D7 combinations (Table 14). Similarly, additivity was observed for PRO 140 used in combination with the gp120 inhibitors PRO 542 and BMS-378806. No antagonism was observed for the PRO 140/BMS-378806 combination against either virus. Overall, these findings are consistent with those seen for cell-cell fusion. Lastly, additive effects were observed for PRO 140 in combination with either zidovudine (NRTI) or nevirapine (NNRTI).

Competition Binding Studies

As described above, additive antiviral effects were observed for inhibitors known (PRO 140 and 2D7) or inferred (UK-427,857 and SCH-D) to compete for CCR5 binding; however, little is known regarding the competitive binding of synergistic compounds (e.g., PRO 140/UK-427,857 and PRO 140/SCH-D). Since non-competitive binding provides a possible mechanism for synergy between CCR5 inhibitors, this issue was explored using labeled forms of UK-427,857 and PRO 140.

Flow cytometry was used to examine inhibition of PRO 140-PE binding to CEM.NRK.CCR5 cells by unlabeled PRO 140, UK-427,857 and SCH-D. PRO 140-PE binding was efficiently inhibited by unlabeled PRO 140, as expected. Complete inhibition was observed in terms of both MFI values (FIG. 16A) and the percent of cells gated for positive binding (FIG. 16B). The EC50 based on MFI data was 2.5 nM (FIG. 16A), and this value compares favorably with the antiviral IC50 of PRO 140 (Tables 13 and 14). Since percent cells gated is a readout for essentially complete inhibition of binding, an EC90 value was calculated as 17 nM, and this value is similar to the antiviral IC90 values observed for PRO 140 (Tables 13 and 14). 2D7 also completely inhibited binding of PRO 140-PE to CEM.NKR-CCR5. The CCR5 specificity of PRO 140-PE was also demonstrated by its inability to bind parental CEM.NKR cells.

Figure 16:
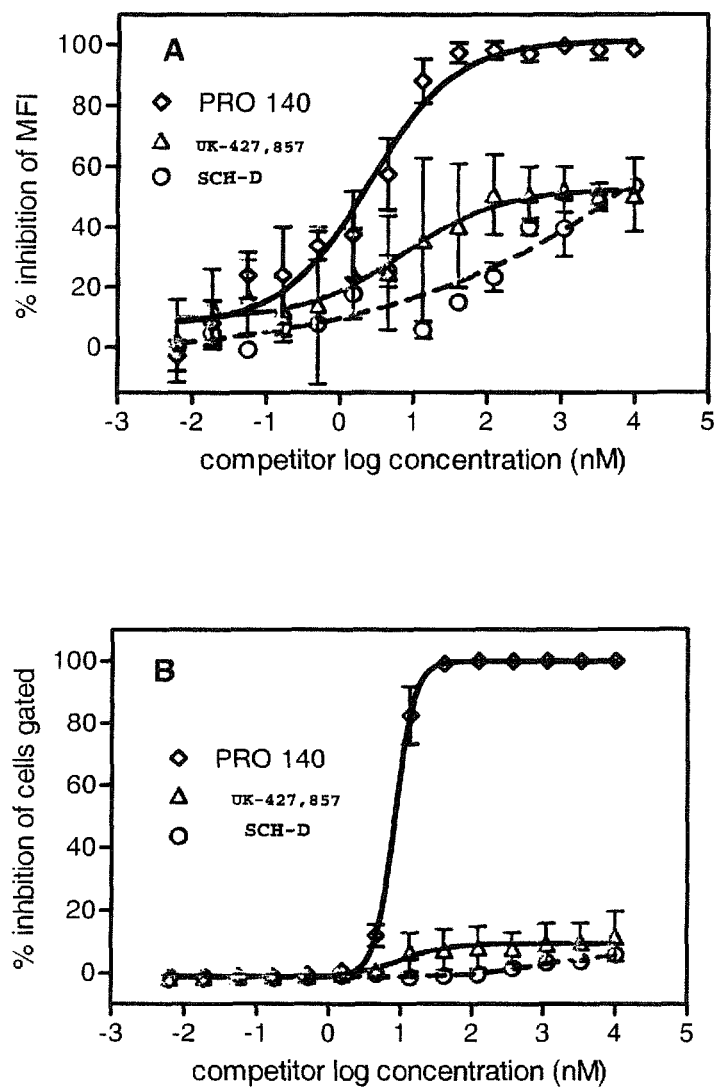

In sharp contrast, modest levels of inhibition were observed for UK-427,857 and SCH-D (FIG. 16). Micromolar concentrations of UK-427,857 and SCH-D reduced PRO 140-PE MFI values by 50% or less (FIG. 16A). More dramatically, UK-427,857 and SCH-D had little impact on the percent of cells gated for positive binding of PRO 140-PE (FIG. 16B). The findings suggest that UK-427,857 and SCH-D partially reduce the number of PRO 140-PE molecules bound per cell; however, these compounds do not reduce the number of cells that bind measurable amounts of PRO 140-PE. Therefore, UK-427,857 and SCH-D represent partial antagonists of PRO 140 binding, and this finding provides a mechanism for the antiviral synergy observed between PRO 140 and these small-molecule CCR5 antagonists.

Figure 17:
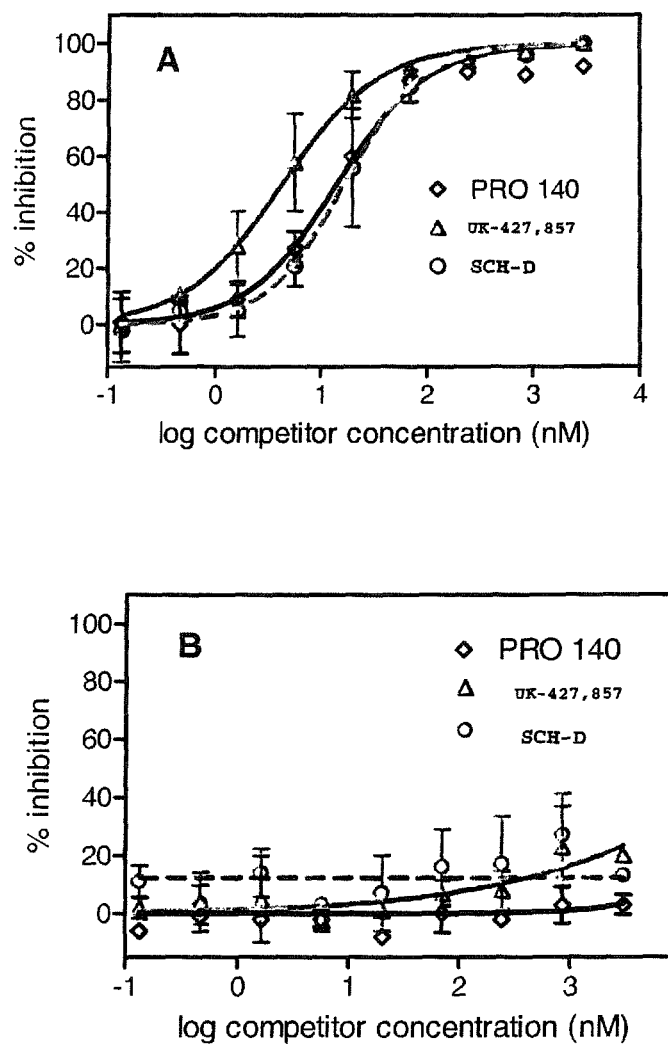

Inhibition of $^3$H-UK-427,857 binding by unlabeled UK-427,857, SCH-D and PRO 140 was next examined. Binding of $^3$H-UK-427,857 to CEM.NKR-CCR5 cells was efficiently inhibited by unlabeled UK-427,857 (FIG. 17A). The EC50 for binding was 4.3 nM and is similar to the antiviral IC50 values observed for UK-427,857 (Tables 13 and 14).

SCH-D also blocked $^3$H-UK-427,857 binding to background levels (FIG. 17A). However, there was no correlation between the compounds' antiviral potency and their potency in blocking $^3$H-UK-427,857 binding. For example, whereas SCH-D demonstrated equal or slightly greater antiviral potency than UK-427,857 (Tables 13 and 14), SCH-D was less potent in blocking $^3$H-UK-427,857 binding (EC50=17 nM, FIG. 17A). This result is consistent with minor differences in the CCR5 binding sites of these compounds.

Surprisingly, PRO 140 also blocked $^3$H-UK-427,857 binding to background levels (FIG. 17A), and this result contrasts with the modest inhibition of PRO 140-PE binding by UK-427,857 (FIG. 16). PRO 140 inhibited $^3$H-UK-427,857 binding with an EC50 of 14 nM, which is 5-10 fold higher than the antiviral IC50 of PRO 140 (Tables 13 and 14).

A final experiment examined the stability of UK-427,857 binding to CEM.NKR-CCR5 cells under the conditions of the competition assay. For this, cells were pre-incubated with $^3$H-UK-427,857 and then the dissociation was examined in the presence of unlabeled UK-427,857, SCH-D and PRO 140. As indicated in FIG. 17B, there was minimal dissociation of $^3$H-UK-427,857 over 30 min at ambient temperature, and UK-427,857 wasn't displaced by either PRO 140 or SCH-D. Therefore, the inability of UK-427,857 to efficiently compete PRO 140 binding to CCR5 (FIG. 16) is not due to rapid dissociation of UK-427,857 from CCR5 during the course of the assay. Collectively, the data indicate that PRO 140 can bind CCR5 in the presence of pre-bound UK-427,857.

Discussion

This study explores interactions between mAb and small-molecule CCR5 inhibitors and examines combinations of CCR5 drugs that currently are in development for HIV-1 therapy. Surprisingly, potent antiviral synergy between the CCR5 mAb PRO 140 and each of three structurally distinct small-molecule CCR5 antagonists was observed. Consistent, high-level synergy was observed across varying assay systems, viral isolates, target cells and inhibition levels. PRO 140 and small-molecule CCR5 antagonists were more potently synergistic when used together rather than in combination with inhibitors that block other stages of HIV-1 entry. In contrast, additive effects were observed for combinations of two small-molecule CCR5 antagonists. Competition binding studies revealed complex and non-reciprocal patterns of CCR5 binding by mAb and small-molecule CCR5 inhibitors, and suggest that the synergistic interactions occur at the level of receptor binding.

Robust synergy between mAb and small-molecule CCR5 inhibitors was observed in this study. Potent synergy was observed for both cell-cell and virus-cell fusion, and there was a good concordance of findings in these two well-established assay systems. Comparable levels of synergy were observed for PRO 140 in combination with each of 3 small-molecule CCR5 antagonists from unrelated chemical series. In addition, consistent synergy was observed for each of two well-characterized HIV-1 envelopes and two CCR5 target cells. Synergy increased with increasing levels of viral inhibition and translated into in vitro dose reductions of up to 14-fold. Viewed alternatively, this degree of synergy provides a corresponding increase in antiviral pressure at a given concentration of drugs, thereby improving viral suppression and potentially delaying the emergence of drug-resistant virus. This is supported by preliminary studies indicating the mAb and small-molecule CCR5 inhibitors possess complementary patterns of viral resistance (Kuhmann et al. 2004 and Marozsan et al. 2005). The present findings provide a rationale for clinical exploration of regimens that combine mAb and small-molecule CCR5 inhibitors.

Potent synergy was also observed for RANTES used in combination with either UK-427,857 or PRO 140. Endogenous levels of RANTES may afford some protection against HIV-1 disease progression during natural infection (Garzino-Demo et al. 1999; Lui et al. 1999), and therefore this finding of synergy has important and positive implications for CCR5-targeted therapies of HIV-1. Antiviral synergy between RANTES and PRO 140 is not surprising based on a prior observation that RANTES signaling is not blocked by antiviral concentrations of murine PRO 140 (PA14) (Olson et al. 1999). Synergy between RANTES and UK-427,857 is less easily explained given that UK-427,857 is a potent CCR5 antagonist. However, these findings are consistent with prior observations of synergy between the small-molecule CCR5 antagonist SCH-C and aminooxypentane-RANTES (AOP-RANTES) (Tremblay et al. 2002), a RANTES derivative that has been evaluated as a potential topical microbicide (Kawamura et al. 2000).

In contrast to the robust synergy observed between mAb and small-molecule CCR5 antagonists, additive effects were observed for combinations of small-molecule CCR5 antagonists. Lack of cooperativity is consistent with the view that these molecules compete for binding to a common pocket on CCR5 (Dragic et al. 2000; Nishikawa et al. 2005; Tsamis et al. 2003; Watson et al. 2005). The in vitro studies do not provide a basis for combining small-molecule CCR5 antagonists in the clinic based solely on inhibition of wild-type virus.

Similarly, potent synergy was not observed between PRO 140 and inhibitors of HIV-1 attachment (PRO 542 and BMS-378806), fusion (enfuvirtide), or reverse transcriptase (zidovudine and nevirapine), and these findings underscore the significance of the synergy observed for PRO 140 and small-molecule CCR5 antagonists. A number of prior studies have examined interactions between various small-molecule CCR5 antagonists (UK-427,857, SCH-C, TAK-220, TAK-652 and E913) and drugs from each of the existing HIV-1 treatment classes. Most (Tremblay et al. 2005 Antivir. Ther.; Tremblay et al. 2005 Antimicrob. Agents Chemother; Tremblay et al. 2002) but not all (Dorr et al. 2005; Maeda et al. 2001) studies have reported broad synergy between CCR5 inhibitors and the other HIV-1 treatment classes, and the divergent results may reflect differences in the compounds and methods used for antiviral testing as well as differences in the methods used for data analysis. When UK-427,857 was tested against 20 licensed antiretroviral agents, additive effects were observed in all but three cases, where modest synergy was reported (Dorr et al. 2005). This result is consistent with the present findings for combinations of PRO 140 and HIV-1 inhibitors that do not target CCR5.

Without intending to be bound by theory, synergy between anti-HIV-1 drugs may stem from a variety of mechanisms. In mixed virus cultures, one compound may inhibit virus resistant to a second compound (Johnson et al. 1991), and NRTI/NNRTI combinations may overcome specific RT-mediated resistance mechanisms (Basavapathruni et al. 2004; Borkow et al. 1999). Metabolic interactions between inhibitors may increase their effective intracellular drug concentrations (Molla et al. 2002), and synergistic entry inhibitors may disrupt interdependent steps in the entry cascade (Nagashima et al. 2001; Tremblay et al. 2000). The present study examined clonal viral envelopes rather than mixed populations, and the extracellular nature of the target argues against metabolic interactions. Multiple domains of gp120 contribute to CCR5 binding (Cormier et al. 2002), but it is unclear at present whether these interactions represent separate or discrete events during infection.

The present findings indicate that antiviral synergy between mAb and small-molecule CCR5 inhibitors may occur at the level of the receptor. As discussed above, mAbs and small molecules bind distinct loci on CCR5 (Dragic et al. 2000; Nishikawa et al. 2005; Tsamis et al. 2003; Olson et al. 1999; Watson et al. 2005). When pre-incubated with CCR5 cells in the present study, PRO 140 completely blocked subsequent binding of UK-427,857 to the receptor; although the PRO 140 concentrations were higher than those needed to block HIV-1 entry into the same cells. In contrast, pre-incubation of CCR5 cells with super-saturating concentrations of UK-427,857 or SCH-D reduced PRO 140 binding by 50% or less. As one possible explanation, PRO 140 could recognize CCR5 conformers that are not bound by UK-427,857 or SCH-D. Although cell-surface CCR5 exists in multiple conformations (Lee et al. 1999), it seems unlikely that the small-molecule antagonists could demonstrate potent antiviral activity while failing to bind a significant fraction of cell-surface CCR5. In this regard, it is important to note that a common cellular background (CEM.NKR-CCR5 cells) was used for competition binding and antiviral studies, and therefore the findings are not related to cell-specific differences in CCR5 expression.

Without intending to be bound by theory, another plausible explanation for the present findings is that PRO 140 is capable of forming a ternary complex with UK-427,857-bound CCR5, and this ternary complex provides an increased barrier to HIV-1 entry. Within the context of this model, PRO 140 may bind UK-427,857-bound CCR5 somewhat less efficiently than free CCR5, as evidenced by the modest reduction in PRO 140 binding in the presence of UK-427,857.

The combination index method is widely used to assess drug-drug interactions. In this method, cooperativity often is defined on the basis of empirical CI values (e.g., <0.9 for synergy and >1.1 for antagonism) irrespective of inter-assay variability. Statistical analyses are performed infrequently, and even more rarely are adjustments made for multiple comparisons. In the absence of such analyses, there is increased potential to overestimate the number of synergistic combinations.

A rigorous and conservative approach to identifying synergistic effects was employed. CI values were tested for statistical significance against the null hypothesis of additivity (CI=1). In addition, these studies determined 20-30 different CI values per experiment (Tables 13 and 14), as is common in synergy studies. In order to reduce the potential for spurious positive results, the significance level was reduced using the Bonferroni correction. A mock combination was also evaluated as a test of these methods for antiviral testing and data analysis. It was therefore concluded that numerous apparent synergies (CI<0.9) could not be distinguished from inter-assay variation based on the available data. However, despite the rigorous nature of these methods, PRO 140 and small-molecule inhibitors demonstrated significant synergy under every test condition, lending credence to this finding. Combinations with CI values that trended towards significance in the present survey could be explored in future studies. For example, data for the PRO 140/enfuvirtide combination suggested modest synergy that trended towards significance; thus this combination may also be useful for treating HIV-1 infection.

A growing body of data indicates that mAb and small-molecule CCR5 antagonists represent distinct subclasses of CCR5 inhibitors, and a number of important parallels can be drawn between NRTI and NNRTI on the one hand and between mAb and small-molecule CCR5 antagonists on the other. In each instance, there are distinct binding loci for the inhibitors on the target protein (reverse transcriptase or CCR5). One set of inhibitors (NNRTI or small-molecule CCR5 antagonists) acts via allosteric mechanisms, while the other set (NRTI or CCR5 mAbs) acts as a competitive inhibitor. Like NRTI and NNRTI, mAb and small-molecule CCR5 inhibitors are synergistic and possess complementary patterns of viral resistance in vitro in preliminary testing (Kuhmann et al. 2004; Marozsan et al. 2005). NRTI and NNRTI represent important and distinct treatment classes even though they target the same protein, and mAb and small-molecule CCR5 inhibitors similarly may offer distinct HIV-1 treatment modalities.

Part IV

Materials And Methods

PRO 140 and small-molecule CCR5 antagonists were prepared and/or obtained as described herein above. The primary R5 HIV-1 isolates JR-FL and Case C 1/85 (CC1/85) were passaged weekly in vitro on peripheral blood mononuclear cells (PBMCC) in the presence or absence of progressively increasing concentrations of PRO 140 or SCH-D, and viral cultures were examined for susceptibility to these and other CCR5 inhibitors. For susceptibility testing, viruses were cultured in vitro on stimulated PBMC. In the presence and absence of serially diluted drug, and the extent of viral replication was determined by p24 ELISA.

Results

For both JR-FL and CC1/85, drug-resistant variants were generated in the presence of PRO 140 and SCH-D. At passage 12, the escape mutants were approximately 10- to 100-fold less susceptible to the drug used for selection. In each case, the escape mutants continued to require CCR5 for replication on PBMC. Complementary patterns of resistance were observed: SCH-D escape mutants were efficiently inhibited by PRO 140 and PRO 140 escape mutants were efficiently inhibited by SCH-D.

Discussion

PRO 140 escape mutants continue to require CCR5 for entry and remain susceptible to small-molecule CCR5 antagonists. In addition, PRO 140 is active against viruses resistant to small-molecule CCR5 antagonists. These findings indicate that PRO 140 and small-molecule CCR5 antagonists may represent distinct subclasses of CCR5 inhibitors.

REFERENCES

U.S. Pat. No. 4,816,567, issued Mar. 28, 1989 to Cabilly et al.
U.S. Pat. No. 5,225,539, issued Jul. 6, 1993 to Gregory Winter.
U.S. Pat. No. 5,229,275, issued Jul. 20, 1993 to Goroff.
U.S. Pat. No. 5,545,806, issued Aug. 13, 1996 to Lonberg et al.
U.S. Pat. No. 5,545,807, issued Aug. 13, 1996 to Surani et al.
U.S. Pat. No. 5,565,332, issued Oct. 15, 1996 to Hoogenboom et al.
U.S. Pat. No. 5,567,610, issued Oct. 22, 1996 to Borrebaeck et al.
U.S. Pat. No. 5,585,089, issued Dec. 17, 1996 to Queen et al.

U.S. Pat. No. 5,591,669, issued Jan. 7, 1997 to Krimpenfort et al.
U.S. Pat. No. 5,693,761, issued Dec. 2, 1997 to Queen et al.
U.S. Pat. No. 6,150,584, issued Nov. 21, 2000 to Kucherlapati et al.
U.S. Pat. No. 6,476,034 B2, issued Nov. 5, 2002 to Wang et al.
U.S. Pat. No. 6,759,519 B2, issued Jul. 6, 2004 to Li et al.
PCT International Publication No. WO 90/07861, published Jul. 26, 1990.
PCT International Publication No. WO 00/35409, published Jun. 22, 2000.
PCT International Publication No. WO 01/55439, published Aug. 2, 2001.
PCT International Publication No. WO 01/90106 A2, published Nov. 29, 2001.
PCT International Publication No. WO 02/22077, published Mar. 21, 2002.
PCT International Publication No. WO 01/62255 A1, published Aug. 30, 2001.
PCT International Publication No. WO 03/082289 A1, published Oct. 9, 2003.
Alkhatib, G., et al. (1996) Science 272:1955.
Allaway, G. P., et al. (1993) AIDS Res. Hum. Retrovir. 9: 581-587.
Allaway, G. P., et al. (1995) AIDS Research and Human Retroviruses. 11: 533-539.
Baba, M., et al. (2005) 12th Conference on Retroviruses and Opportunistic Infections. Boston, Mass., Feb. 22-25, 2005, Abstract 541.
Baba, M., et al. (1999) Proc. Nab. Acad. Sci. USA 96: 5698-5703.
Balotta, C, P. et al. (1997) AIDS 11: F67-F71.
Basavapathruni, A., et al. (2004) J Biol Chem. 279:6221-6224
Berger, E. A. (1997) AIDS 11 (Suppl A): S3-S16.
Bieniasz, P. D. and B. R. Cullen (1998) Frontiers in Bioscience 3: d44-58.
Biti, R., R. et al. (1997) Nature Med. 3: 252-253.
Borkow, G., et al, (1999) Antimicrob. Agents Chemother. 43:259-263
Burkly, L., et al. (1992) J. Immunol. 149: 1779-1787.
Burkly, L., et al. (1995) J. Virol. 69: 4267-4273.
Choe, H., et al. (1996) Cell 85: 1135-1148.
Chou, T. C. and D. C. Rideout (1991) Synergism and antagonism in chemotherapy. Academic Press, New York.
Chou, T. C. and P. Talalay (1984) Adv. Enzyme Regulation 22: 27-55.
Cocchi, F., et al. (1995) Science 270: 1811-1815.
Combadiere, C, et al. (1996) J. Leukocyte Biol. 60: 147-152.
Connor, R. I., et al. (1997) J. Exp. Med. 185: 621-628.
Cormier, E. G. and T. Dragic (2002) J Virol. 76:8953-8957.
Cudeck, R. and L. L. O'Dell (1994) Psychol. Bull. 115:475-487.
Dalgleish, A. G., et al. (1984) Nature 312: 763-766.
Demarest, J., et al. (2004) 11th Conference on Retroviruses and Opportunistic Infections, Abstract 139. San Francisco, Calif., Feb. 8-11, 2004.
Deng, H., et al. (1996) Nature 381: 661-666.
Dorr, P., et al. (2003) 10th Conference on Retroviruses and Opportunistic Infections, Boston, Mass., Feb. 10-14, 2003, Paper #12.
Dorr, T, P., et al. (2005) Antimicrobial Agents and Chemotherapy 49:4721-4732.
Dragic, T., et al. (1997) Advances in Research and Therapy 7: 2-13.
Dragic, T., et al. (1992) J. Virol. 66: 4794-4802.
Dragic, T., et al. (1996) Nature 381: 667-673.
Dragic, T., et al. (2000) Proc Nab Acad Sci USA 97:5639-44.
Este J A. (2002) Curr. Opin. Investig. Drugs. 3: 379-383.
Fatkenheuer, G., et al. (2005) Nat Med 11:1170-1172.
Feng, Y., et al. (1996) Science 272: 872-877.
Finke, P. E. et al. (2001) Bioorg. Med. Chem. Lett. 11: 2475-2479.
Garzino-Demo, A., et al. (1999) Proc Natl Acad Sci USA. 96:11986-11991.
Hale, J. J. et al. (2001) Bioorg. Med. Chem. Lett. 11: 2741-2745.
Hale, J. J. et al. (2002) Bioorg. Med. Chem. Lett. 12: 2997-3000.
Hegde, V. R. et al. (2004) Bioorg. Med. Chem. Lett. 12: 5339-5342.
HGS Press Release (2004) Human Genome Sciences characterizes panel of novel human monoclonal antibodies that specifically antagonize the CCR5 receptor and block HIV-1 entry. Nov. 2, 2004. HGS Press Release (2005) Human Genome Sciences begins dosing of patients in a phase 1 clinical trial of CCR5 mAb in patients infected with HIV-1. Mar. 30, 2005.
Huang, Y., et al. (1996) Nature Med. 2: 1240-1243.
Huffnagle, G. B., et al. (1999) Immunol. 163: 4642-4646.
Y. Iizawa, et al. (2003) 10th Conference on Retroviruses and Opportunistic Infections. Boston, Mass., Feb. 10-14, 2003
Imamura, S. et al. (2004a) Bioorg. Med. Chem. 12: 2295-2306.
Imamura, S. et al. (2004b) Chem. Pharm. Bull. (Tokyo) 52: 63-73.
Imamura, S. et al. (2005) Bioorg. Med. Chem. 13: 397-416.
Jayasuriya, H. et al. (2004) J. Nat. Prod. 67: 1036-1038.
Johnson, V. A., et al. (1991) Journal of Infectious Diseases 164:646-655.
Kawamura, T., et al. (2000) J Exp Med. 192:1491-1500.
Kuhmann, S. E., et al. (2004) J Virol 78:2790-2807.
Ketas, T. J., et al. (2003) J. Virol. 77: 2762-2767.
Kim D. et al. (2001a) Bioorg. Med. Chem. Lett. 11: 3099-3102.
Kim D. et al. (2001b) Bioorg. Med. Chem. Lett. 11: 3103-3106.
Kim D. et al. (2005) Bioorg. Med. Chem. Lett. 15: 2129-2134.
Klatzmann, D., et al. (1984) Nature 312: 382-385.
Koyanagi, Y., et al. (1987) Science 236: 819-822.
Kuhmann, S. E. et al. (2004) J. Virol. 78: 2790-2807.
Kumar, S et al. (2003) J. Pharmacol. Exp. Ther. 304: 1161-1171.
Laal, S., et al. (1994) J. Virol. 68: 4001-4008.
Lalezari, J. P., et al. (2003) New Engl. J. of Med. 348: 2175-2185.
Lalezari, J., et al. (2004) 44th Annual Interscience Conference on Antimicrobial Agents and Chemotherapy, Abstract 2871, Washington, D.C., Oct. 30-Nov. 2, 2004.
Lalezari, J., et al. (2005) AIDS 19:1443-1448.
Lapidot, T. (2001) Ann. N.Y. Acad. Sci. 938: 83-95.
Lazzarin, A., et al. (2003) New Engl. J. Med. 348: 2186.
Lee, B., et al. (1999) Journal of Biological Chemistry 274: 9617-9626.
Li, A., et al. (1997) AIDS Res. Hum. Retrovir. 13: 647-656.
Li, A., et al. (1998) J. Virol. 72: 3235-3240.
Lin, P. F., et al. (2003) Proc. Natl. Acad. Sci. USA 100: 11013-11018.
Lin, P. F., et al. (2002) 9th Conference on Retroviruses and Opportunistic Infections. Seattle, Wash., Feb. 24-28, 2002
Littman, D. R. (1998) Cell 93: 677-680.
Litwin, V., et al. (1996) J. Virol. 70: 6437-6441.
Liu, R., et al. (1996) Cell 86: 367-377.
Liu, H., at al. (1999) Proceedings of the National Academy of Sciences of the United States of America 96:4581-4585
Lynch, C. L. et al. (2003a) Bioorg. Med. Chem. Lett. 12: 3001-3004.
Lynch, C. L. et al. (2003b) Bioorg. Med. Chem. Lett. 13: 119-123.

Lynch, C. L. et al. (2002) Bioorg. Med. Chem. Lett. 12: 677-679.
Lynch, C. L. et al. (2003c Org. Lett. 5: 2473-2475.
Maddon, P. J., et al. (1986) Cell 47: 333-348.
Maeda, K. et al. (2004) J. Virol. 78: 8654-8662.
Maeda, K. et al. (2001) J. Biol. Chem. 276: 35194-35200.
Marozsan, A. J. et al. (2005) Virology 338: 182-199.
McCombie, S. W. et al. (2001) Bioorg. Med. Chem. Lett. 13: 567-571.
McDougal, J. S., et al. (1986) Science 231: 382-385.
Merluzzi, V. J., et al. (1990) Science 250: 1411-1413.
Michael, N. L., et al. (1997) Nature Med. 3: 338-340.
Molla, A., et al. (2002) Antimicrob. Agents Chemother. 46:2249-2253.
Moore, J. P., Q. J. Sattentau, P. J. Klasse and L. C. Burkly (1992) J. Virol. 66: 4784-4793.
Nagashima, K. A., at al. (2001) J. Infect. Dis. 183: 1121-1125.
Nakata, H. et al. (2005) J. Virol. 79: 2087-2096.
Nishikawa, M., et al. (2005) Antimicrob. Agents Chemother. 49:4708-4715.
O'Brien, T. R., et al. (1997) Lancet 349: 1219.
Olson, W. C, et al. (1999) J. Virol. 73: 4145-4155.
Olson, W. C. and P. J. Maddon (2003) Current Drug Targets-Infectious Disorders 3:283-294.
Palani, A, et al. (2002) J. Med. Chem. 45: 3143-3160.
Palani, A, et al. (2001) J. Med. Chem. 44: 3339-3342.
Palani, A, et al. (2003a) Bioorg. Med. Chem. Lett. 13: 705-708.
Palani, A, et al. (2003b) Bioorg. Med. Chem. Lett. 13: 709-712.
Palella, F. J., et al. (1998) The New England Journal of Medicine 338:853.
Raport, C. J., et al. (1996) J. Leukocyte Biol. 59: 18-23.
Ray, N. and R. W. Doms (2006) Curr. Top. Microbiol Immunol. 303:97-120.
Reyes, G. (2001) Development of CCR5 antagonists as a new class of anti-HTV therapeutic. 8th Conference on Retroviruses and Opportunistic Infections. Chicago, Ill., Feb. 5, 2001.
Reynes, J., et al. (2002) SCH C: Safety and antiviral effects of a CCR5 receptor antagonist in HIV-1 infected subjects. 9th Conference on Retroviruses and Opportunistic Infections. Seattle, Wash., Feb. 25, 2002
Robinson, B. S., et al. (2000) Antimicrob. Agents Chemother. 44: 2093-2099.
Roschke, V., et al. (2004) 44th Annual Interscience Conference on Antimicrobial Agents and Chemotherapy, Abstract 2871, Washington, D.C., Oct. 30-Nov. 2, 2004, Abstract #2871.
Samson, M., at al. (1997) J. Biol. Chem. 272: 24934-24941.
Schecter, A. D., et al. (2000) J. Biol. Chem. 275: 5466-5471.
Schols, D., et al. (1997) J. Ex. Med. 186: 1383-1388.
Schuh, J. M., et al. (2002) FASEB J, 16: 228-230.
Schurmann, D., et al. (2004) Abstract 140LB, San Francisco, Calif., Feb. 8-11, 2004.
Seibert, C., et al. (2006) Virology 349(1):41-54.
Seto, M. et al. (2005) Bioorg. Med. Chem. Left. 13: 363-386.
Seto, M. et al. (2004a) Chem. Pharm. Bull. (Tokyo). 52: 818-829.
Seto, M. et al. (2004b) Chem. Pharm. Bull. (Tokyo). 52: 577-590.
Shah, S. K. et al. (2005) Bioorg. Med. Chem. Lett. 15: 977-982.
Shankaran, K. et al. (2004a) Bioorg. Med. Chem. Lett. 14: 3589-3593.
Shankaran, K. et al. (2004b) Bioorg. Med. Chem. Lett. 14: 3419-3424.
Shen, D. M. et al. (2004a) Bioorg. Med. Chem. Lett. 14: 935-939.
Shen, D. M. et al. (2004b) Bioorg. Med. Chem. Lett. 14: 941-945.
Shiraishi, M., et al. (2000) J. Med. Chem. 43: 2049-2063.
Shu, M. et al. (2004) Bioorg. Med. Chem. Lett. 14: 947-52.
Si, Z., et al. (2004) Proc. Natl. Acad. Sci. USA 101: 5036-5041.
Simmons, G., et al. (1996) J. Virol. 70: 8355-8360.
Spenlehauer, C., et al. (2001) Virology 280:292-300.
Strizki, J. M. et al. (2001) Proc. Natl. Acad. Sci. USA. 98: 12718-12723.
Tagat, J. R. et al. (2001a) J. Med. Chem. 44: 3343-3346.
Tagat, J. R. et al. (2001b) Bioorg. Med. Chem. Lett. 11: 2143-2146.
Tagat, J. R., et al. (2004) J. Med. Chem. 47: 2405-2408.
Takashima, K., et al. (2005) Antimicrob. Agents Chemother. 49:374-3482.
Thali, M., et al. (1992) J. Acquir. Immune Defic. Syndr. 5: 591-599.
Thoma, G. et al. (2004) J. Med. Chem. 47: 1939-1955.
Tilley, S. A., et al. (1992) AIDS Res. Hum. Retrovir. 8: 461-467.
Tran, E. H., et al. (2000) Eur. J. Immunol. 30: 1410-1415.
Tremblay, C., et al. (2000) Journal of Acquired Immune Deficiency Syndromes and Human Retrovirology 25:99-102
Tremblay, C. L., et al. (2002) Antimicrobal Agents and Chemotherapy 46:1336-1339.
Tremblay, C. L., et al. (2005) 12th Conference on Retroviruses and Opportunistic Infections. Boston, Mass., Feb. 22-25, 2005, Abstract 542.
Tremblay, C. L., et al. (2005) Antivir. Ther. 10:967-968.
Tremblay, C. L., et al. (2005) Antimicrob. Agents Chemother. 49:3483-3485.
Trkola, A., et al. (2001) J. Virol. 75: 579-588.
Trkola, A., et al. (1999) Journal of Virology 73:8966-8974.
Trkola, A., et al. (1998) J. Virol. 72: 1876-1885.
Tsamis, F., et al. (2003) Journal of Virology 77:5201-5208.
Vijh-Warrier, S., et al. (1996) J. Virol. 70: 4466-4473.
Watson, C., et al. (2005) Mol Pharmacol. 67:1268-1282.
Wild, C., et al. (1992) PNAS 89:10537-10541.
Willoughby, C. A. et al. (2001) Bioorg. Med. Chem. Lett. 11: 3137-41.
Willoughby, C. A. et al. (2003) Bioorg. Med. Chem. Lett. 13: 427-431.
Wu, L., et al, (1997) J. Exp. Med. 186: 1373-1381.
Zhou, Y., et al. (1998) J. Immunol. 160: 4018-4025.
Zhu, P., et al. (2001) J. Virol. 75: 6682-6686.

What is claimed is:

1. A method of potentiating HIV-1 inhibitory activity of a small molecule CCR5 receptor antagonist in an HIV-1-infected subject who has been administered, or will be administered, the small molecule CCR5 receptor antagonist in the treatment of the subject's HIV-1 infection, comprising administering to the subject an HIV-1 inhibitory amount of an anti-CCR5 receptor monoclonal antibody, wherein the amounts of the anti-CCR5 receptor monoclonal antibody and the small molecule CCR5 receptor antagonist combined, produces a synergistic antiviral effect on treating the HIV-1 infection, thereby potentiating the HIV-1 inhibitory activity of the small molecule CCR5 receptor antagonist, wherein the anti-CCR5 receptor monoclonal antibody is PRO 140, said PRO 140 comprising (i) two light chains, each light chain comprising the expression product of the plasmid designated pVK:HuPRO140-VK (ATCC Deposit Designation PTA-4097), and (ii) two heavy chains, each heavy chain comprising the expression product of either the plasmid designated pVg4:HuPRO140 HG2-VH (ATCC Deposit Designation PTA-4098) or the plasmid designated pVg4:HuPRO140 (mut B+D+I)-VH (ATCC Deposit Designation PTA-4099) and wherein the small molecule CCR5 receptor antagonist is (1-[(4,6-dimethyl-5-pyrimidinyl) carbonyl]-4-[4-[2-methoxy-1

(R)-4-(trifluoromethyl)phenyl]ethyl-3(S)-methyl-1-piperazinyli-4-methylpiperidine) (UK-427,857) having the structure:

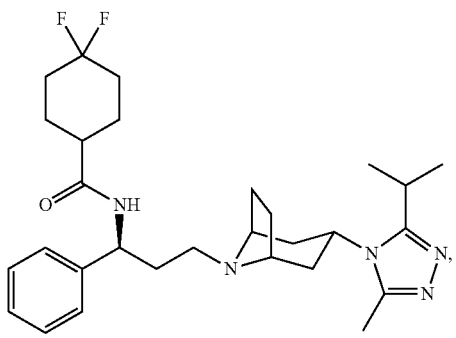 [SMILES: Cc1nnc(C(C)C)n1C1CC2CCC(C1)N2CC[C@H](NC(=O)C1CCC(F)(F)CC1)c1ccccc1]

TAK-779 having the structure:

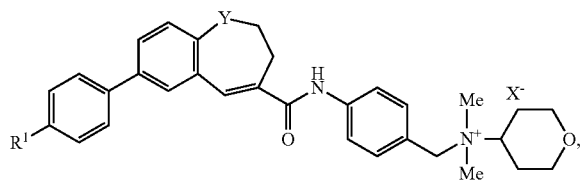

where Y=-CH$_2$, X=-Cl, R1=-CH$_3$
TAK-652 having the structure:

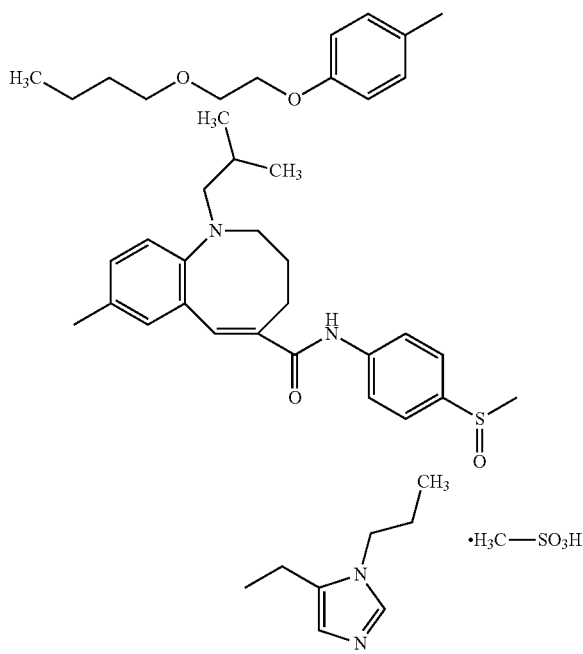

or GW873140.

2. The method of claim 1, wherein the anti-CCR5 receptor monoclonal antibody is a humanized, human, or chimeric antibody.

3. The method of claim 1, wherein each heavy chain comprises the expression product of the plasmid designated pVg4:HuPRO140 HG2-VH (ATCC Deposit Designation PTA-4098).

4. The method of claim 1, wherein the PRO 140 is administered via intravenous infusion.

5. The method of claim 1, wherein the PRO 140 is administered via subcutaneous injection.

6. The method of claim 1, wherein the small molecule CCR5 receptor antagonist is orally administered.

7. The method of claim 1, wherein the anti-CCR5 receptor monoclonal antibody is administered concurrently with administration of the small molecule CCR5 receptor antagonist.

8. The method of claim 1, wherein the anti-CCR5 receptor monoclonal antibody is administered prior to administration of the small molecule CCR5 receptor antagonist.

9. The method of claim 1, wherein the anti-CCR5 receptor monoclonal antibody is administered subsequent to administration of the small molecule CCR5 receptor antagonist.

10. The method of claim 1, wherein the anti-CCR5 receptor monoclonal antibody is administered in a dose of 0.01 mg per kg body weight to 50 mg per kg body weight of the subject.

11. The method of claim 10, wherein the anti-CCR5 receptor monoclonal antibody is administered in a dose of 0.05 mg per kg body weight to 25 mg per kg body weight of the subject.

12. The method of claim 10, wherein the anti-CCR5 receptor monoclonal antibody is administered in a dose of 0.1 mg per kg body weight to 10 mg per kg body weight of the subject.

13. The method of claim 10, wherein the anti-CCR5 receptor monoclonal antibody is administered in a dose of 0.5 mg per kg body weight to 5 mg per kg body weight of the subject.

14. The method of claim 1, wherein the synergistic antiviral effect comprises a reduction in HIV-1 viral load in the HIV-1-infected subject by at least 90% following administration of the antibody, and wherein the reduction is maintained for at least two weeks.

15. The method of claim 1, wherein the anti-CCR5 receptor monoclonal antibody is to be administered at a predefined interval, and the predefined interval is at least once weekly, every two to four weeks, every two weeks, every four weeks, or at least once monthly.

16. The method of claim 1, wherein the small molecule CCR5 receptor antagonist is (1-[(4,6-dimethyl-5-pyrimidinyl) carbonyl]-4-[4-[2-methoxy-1(R)-4-(trifluoromethyl) phenyl]ethyl-3(S)-methyl-1-piperazinyli-4-methylpiperidine) (UK-427,857) having the structure:

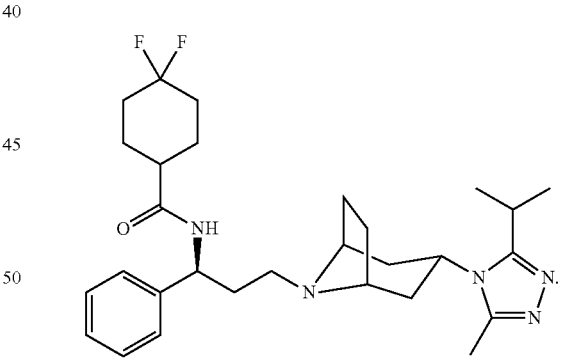

17. The method of claim 1, wherein the small molecule CCR5 receptor antagonist is TAK-779 having the structure:

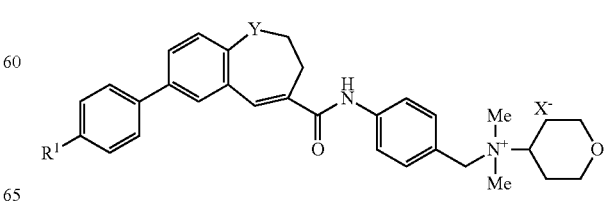

where Y=—CH$_2$, X=—Cl, R1=—CH$_3$

18. The method of claim 1, wherein the small molecule CCR5 receptor antagonist is TAK-652 having the structure:
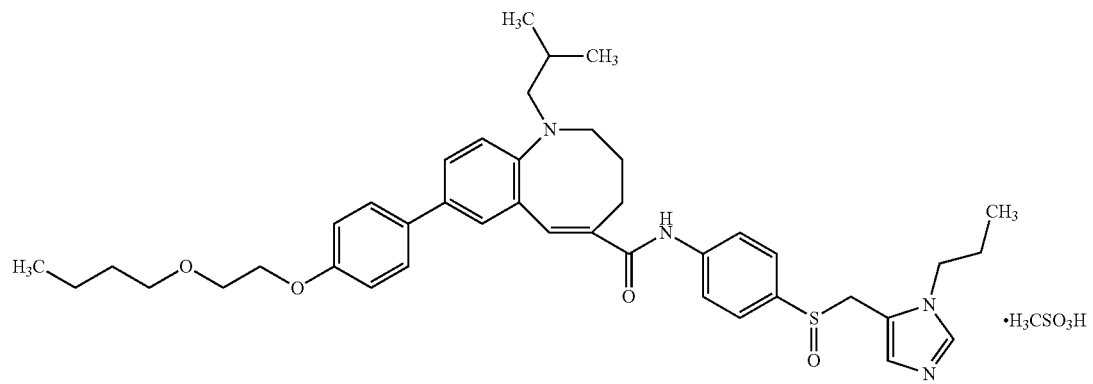
19. The method of claim 1, wherein the small molecule CCR5 receptor antagonist is GW873140.
* * * * *